United States Patent [19]

Narula et al.

[11] Patent Number: 5,276,211
[45] Date of Patent: Jan. 4, 1994

[54] MIXTURES OF ARYL OXABICYCLOOCTANE DERIVATIVES, MIXTURES OF PHENYL NORBORNANE DERIVATIVES, PROCESSES FOR PREPARING SAME, PERFUMERY USES THEREOF AND INTERMEDIATES USED IN SAID PROCESSES

[75] Inventors: Anubhav P. S. Narula, Hazlet; John J. De Virgilio, Red Bank, both of N.J.

[73] Assignee: International Flavors & Fragrances Inc., New York, N.Y.

[21] Appl. No.: 29,580

[22] Filed: Mar. 11, 1993

Related U.S. Application Data

[62] Division of Ser. No. 982,380, Nov. 25, 1992.

[51] Int. Cl.$^5$ .................................................. C07C 33/34
[52] U.S. Cl. ..................................... 568/807; 549/397; 549/465; 585/407
[58] Field of Search ................ 568/807; 549/397, 465; 585/407

[56] References Cited

U.S. PATENT DOCUMENTS 5,087,707  2/1992  Narula et al. ..................... 549/396

OTHER PUBLICATIONS

Beilstein, H 6, 591 (E III Jun. 27, 1971).

*Primary Examiner*—James H. Reamer
*Attorney, Agent, or Firm*—Arthur L. Liberman

[57] ABSTRACT

Described are aryl oxabicyclooctane derivatives and phenyl norbornane derivatives defined according to the structures:

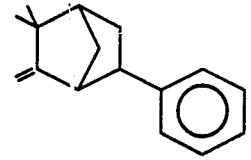

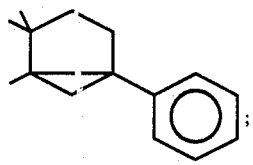

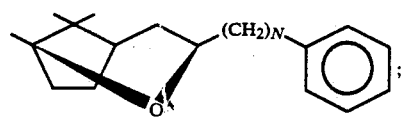

and

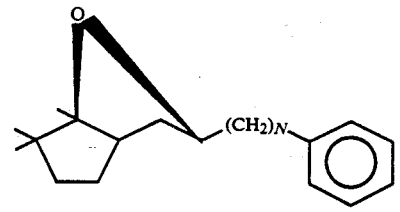

wherein N is an integer selected from the group consisting of 1 and 2, processes for preparing same, perfumery uses thereof and intermediates used in said processes which intermediates are defined according to the structures:

and (Abstract continued on next page.)

-continued
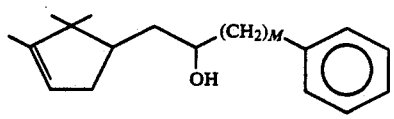
wherein M is 0, 1 or 2 and X is chloro or bromo.
Also described are the by-products having the structure:
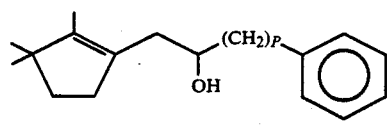
wherein P is 1 or 2 and uses thereof in perfumery.
7 Claims, 45 Drawing Sheets

GC PROFILE FOR EXAMPLE I.

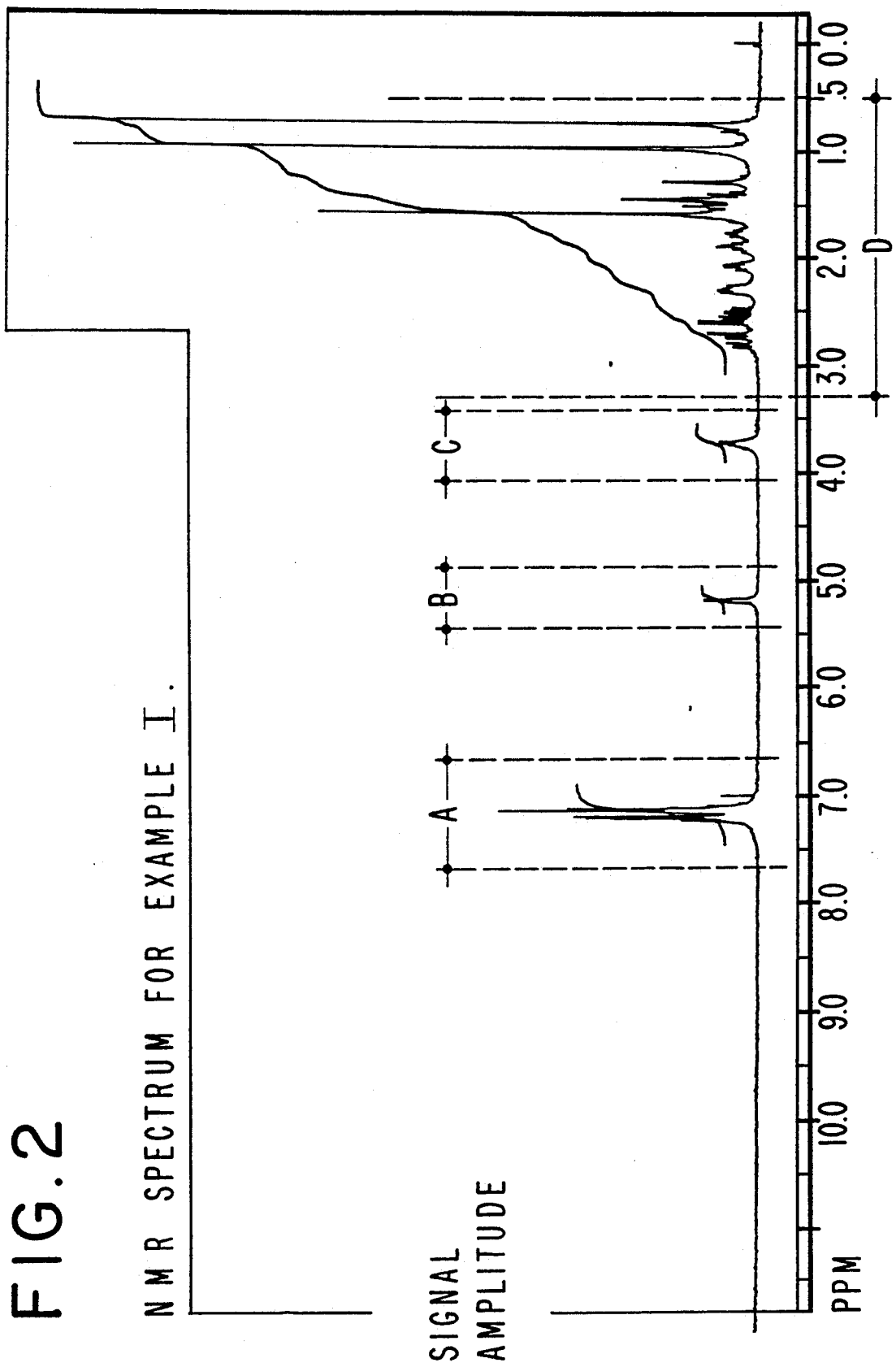

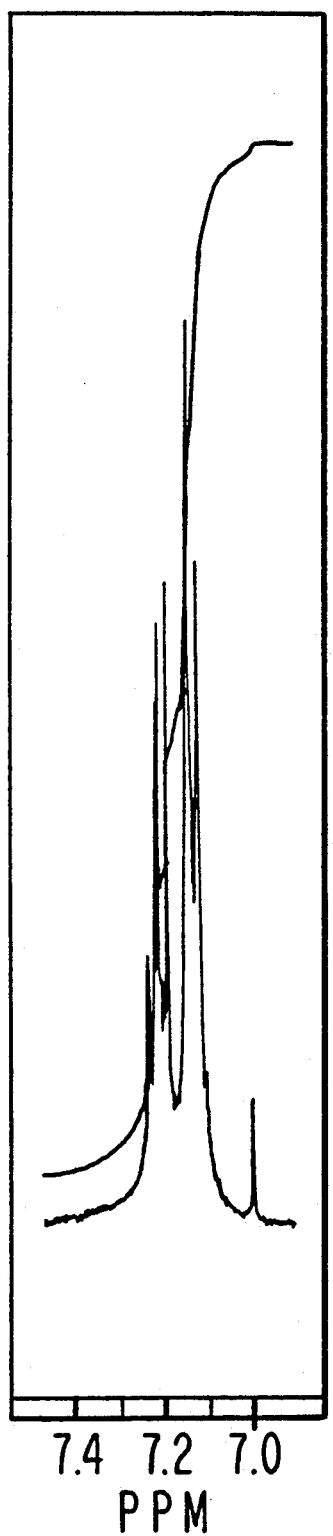# FIG.2-A
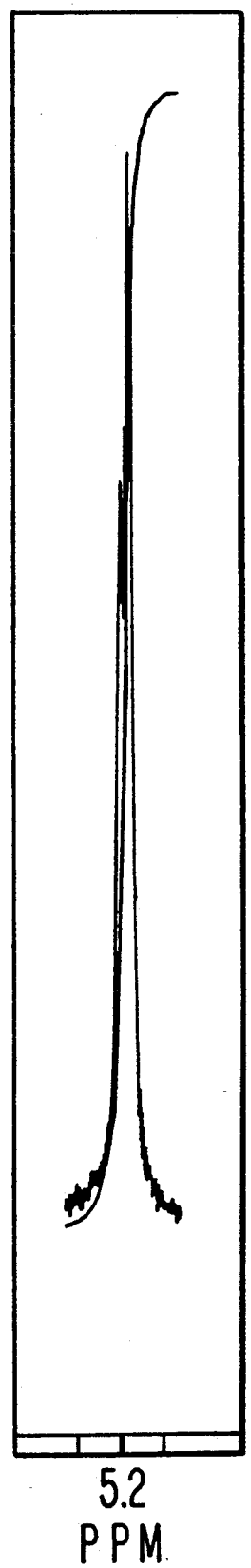# FIG.2-B

FIG. 2-C
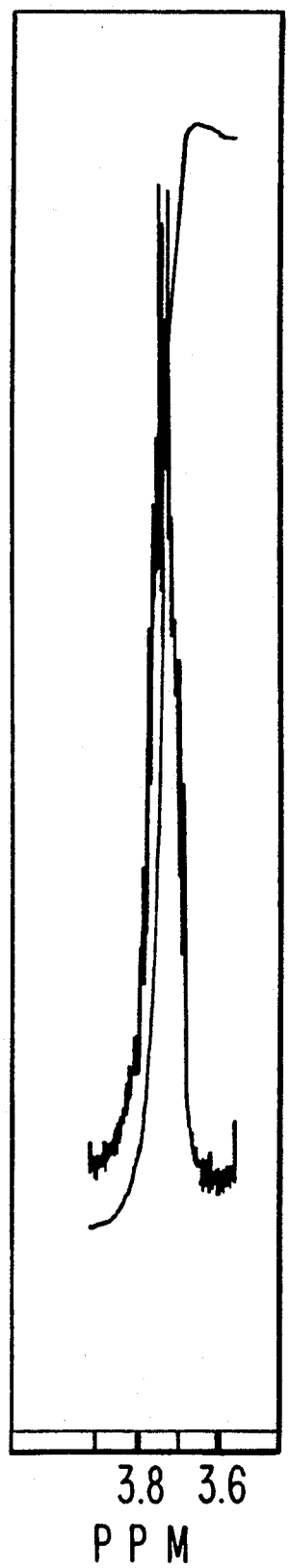

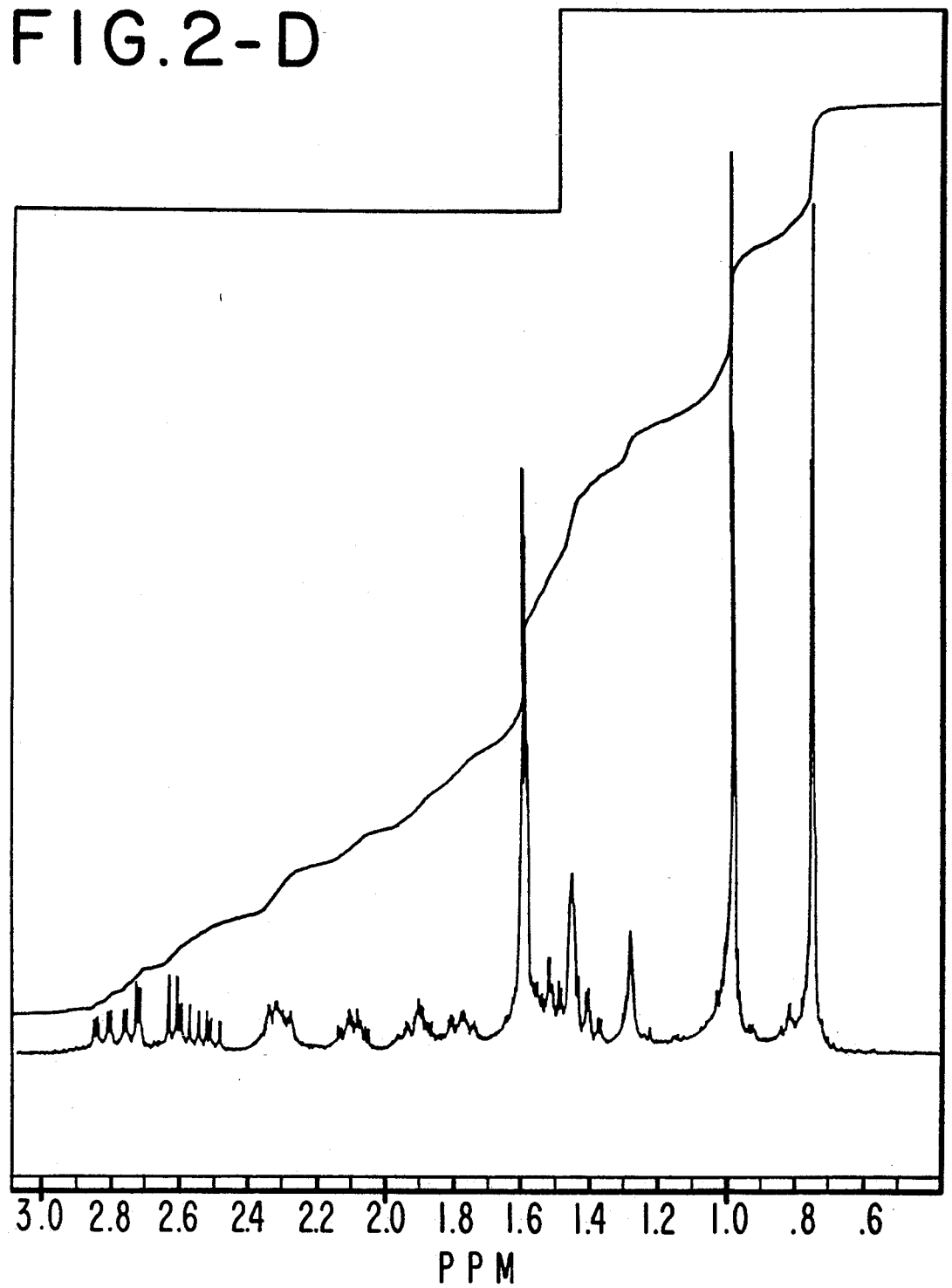
FIG.2-D

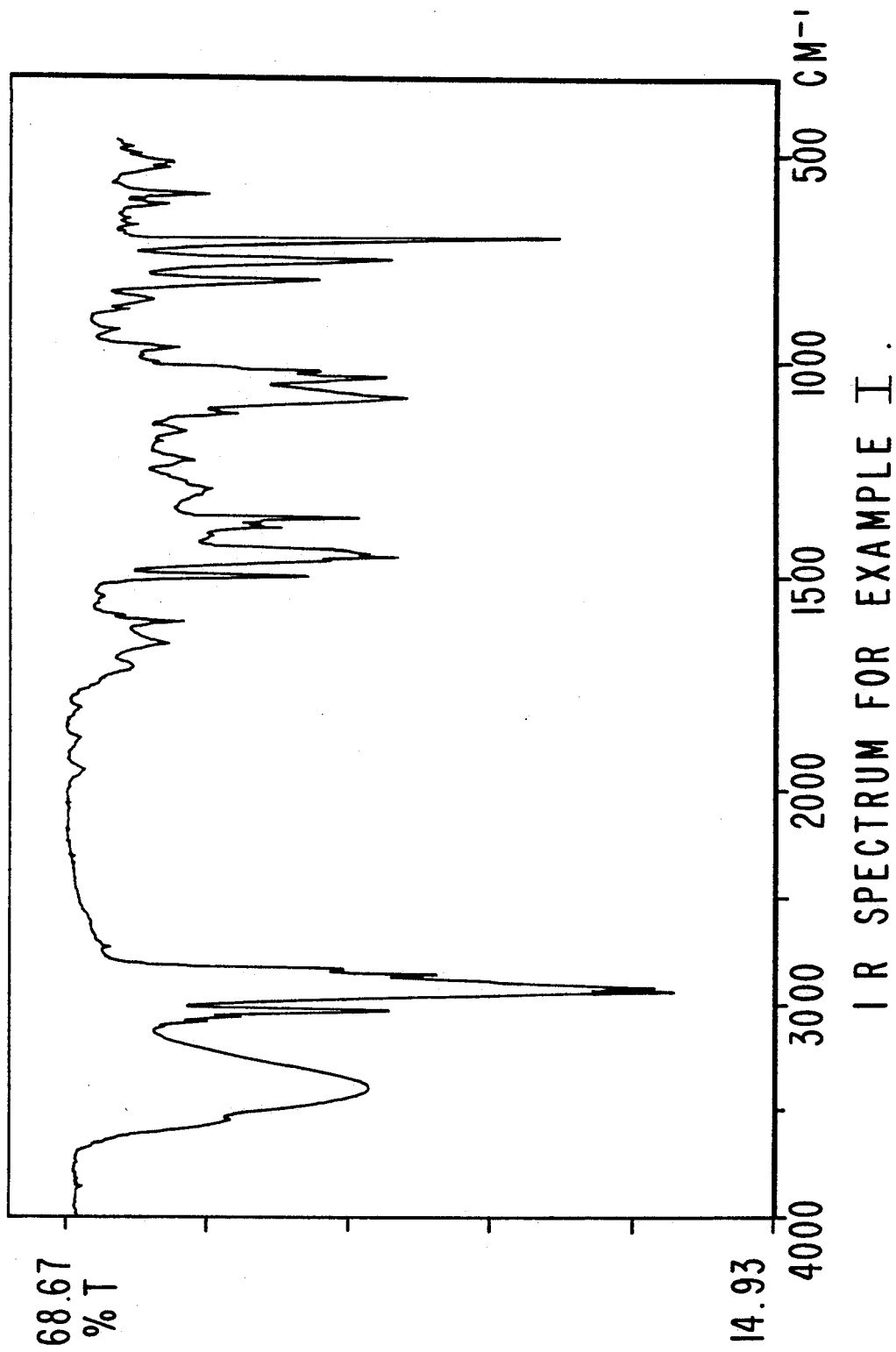

GC PROFILE FOR EXAMPLE II.

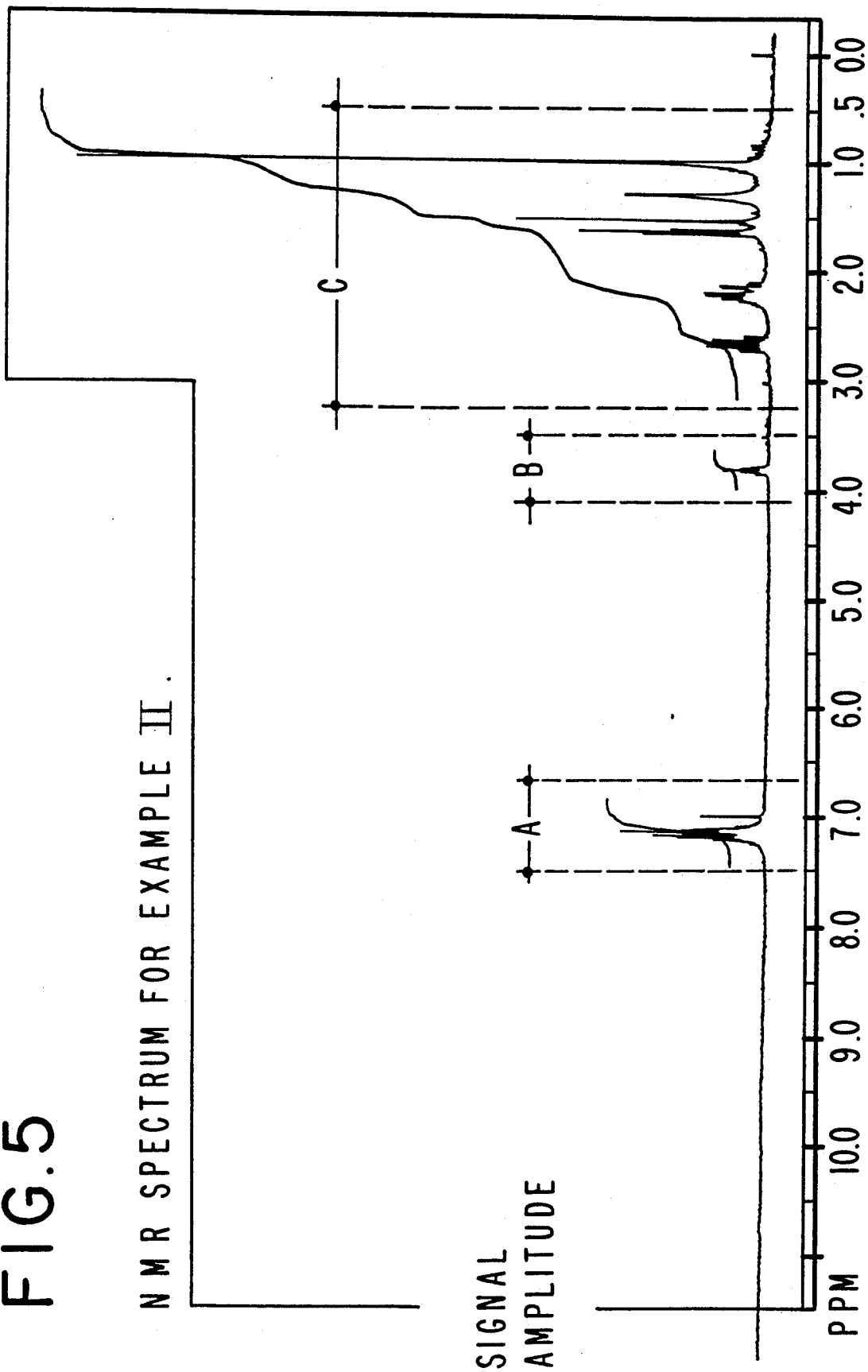

FIG.5-A
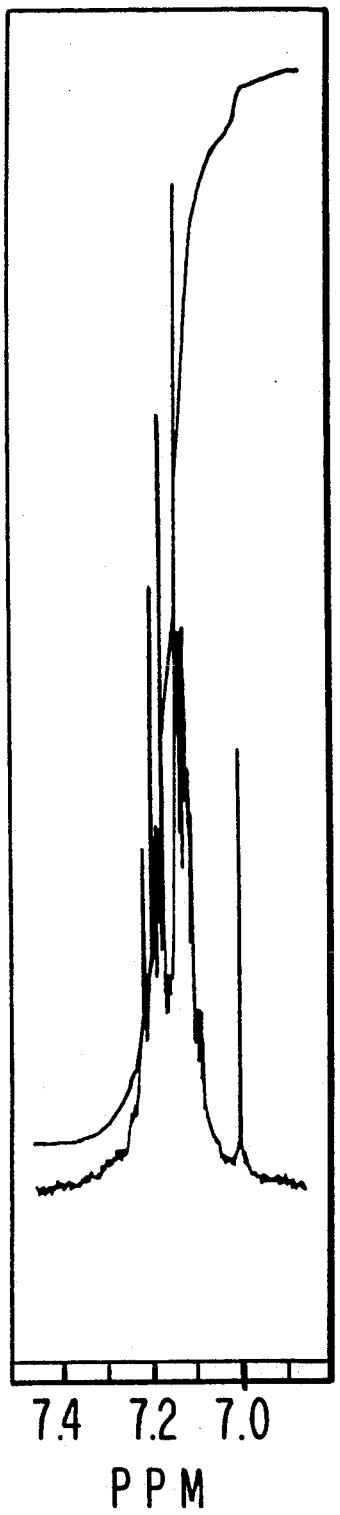
7.4  7.2  7.0
PPM
FIG.5-B
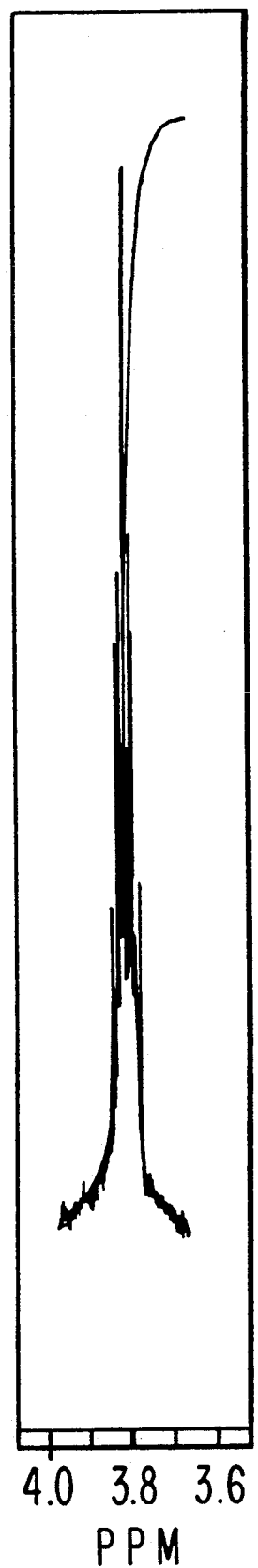
4.0  3.8  3.6
PPM

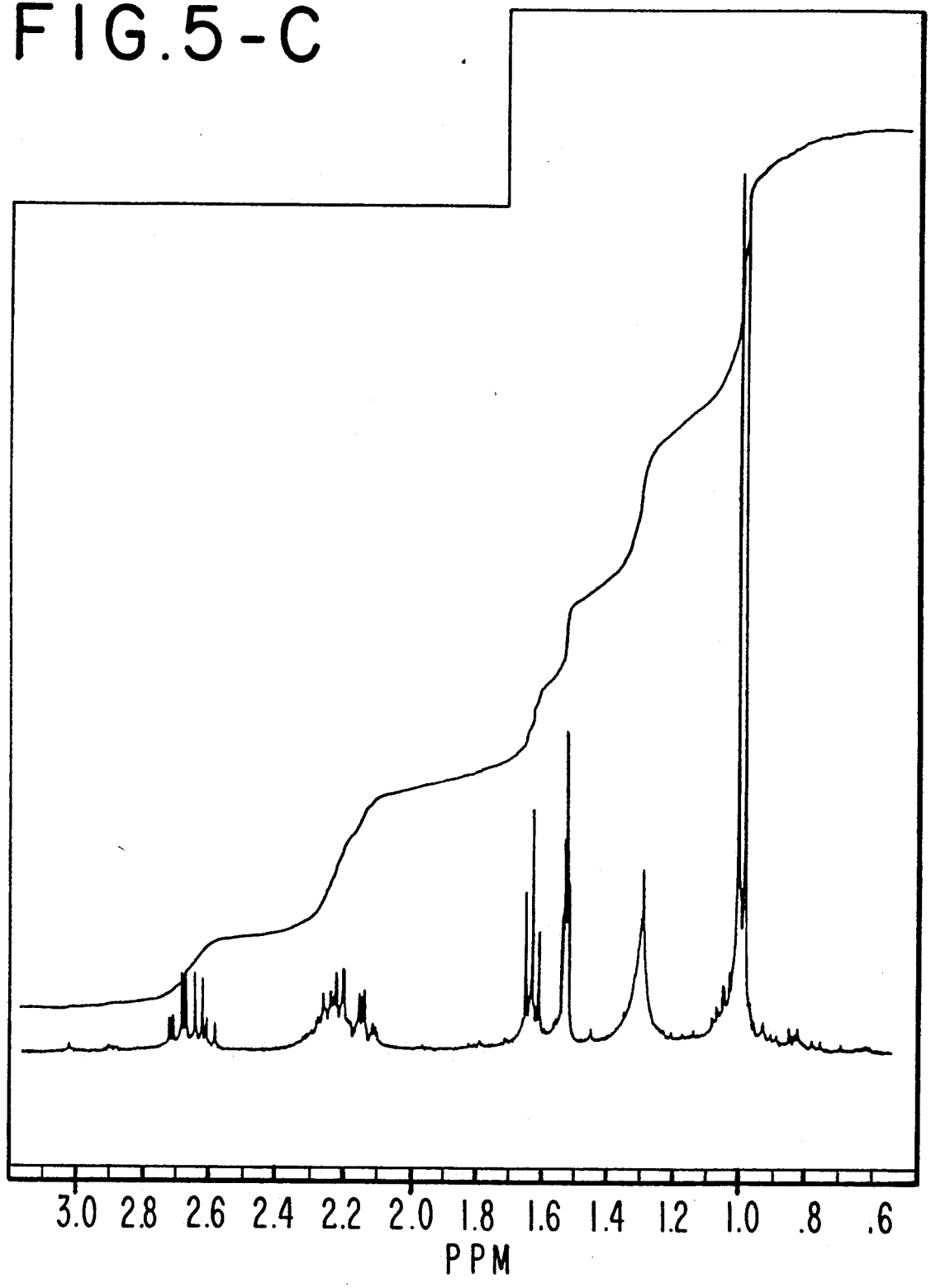
FIG.5-C

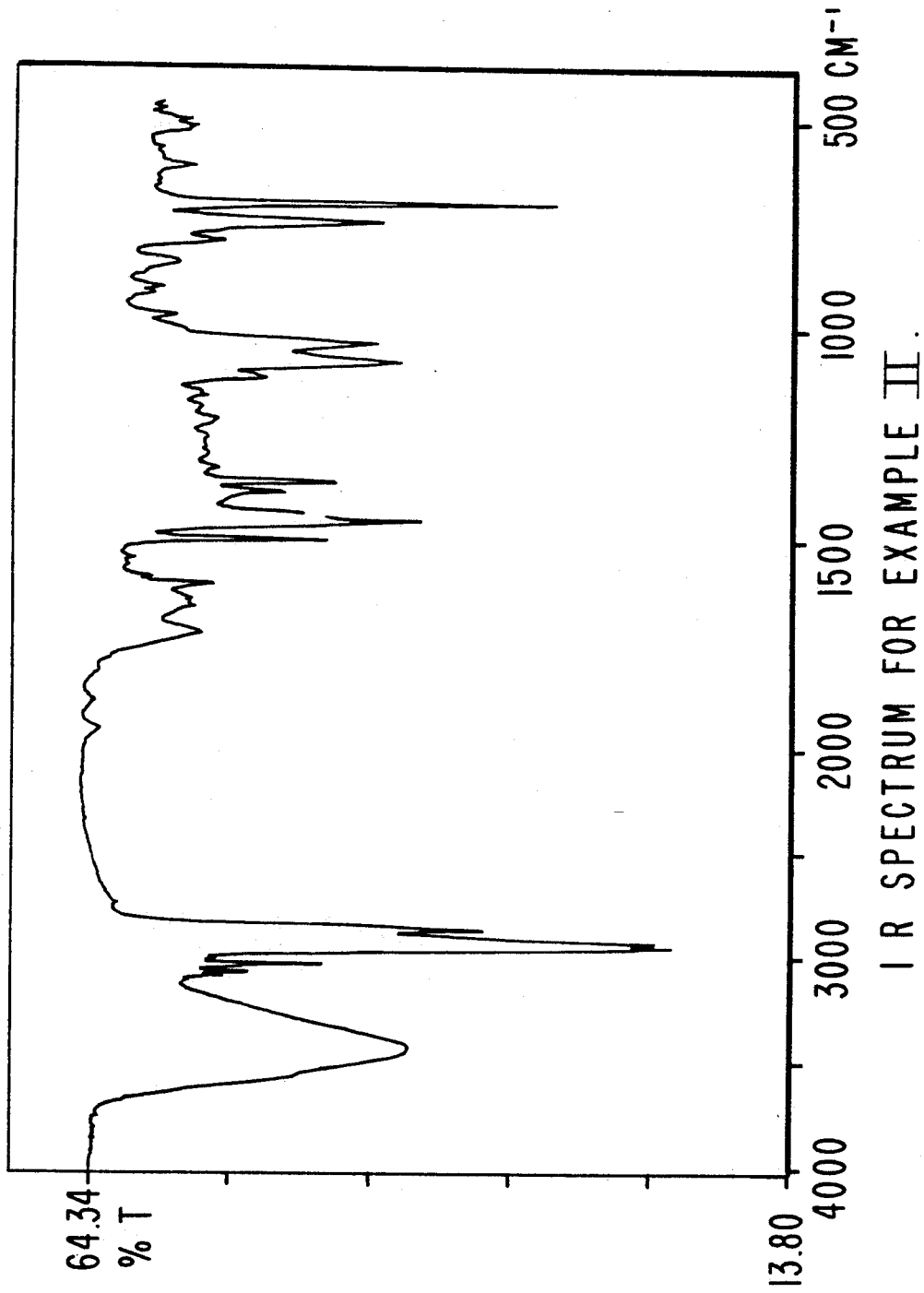
FIG.6 IR SPECTRUM FOR EXAMPLE II.

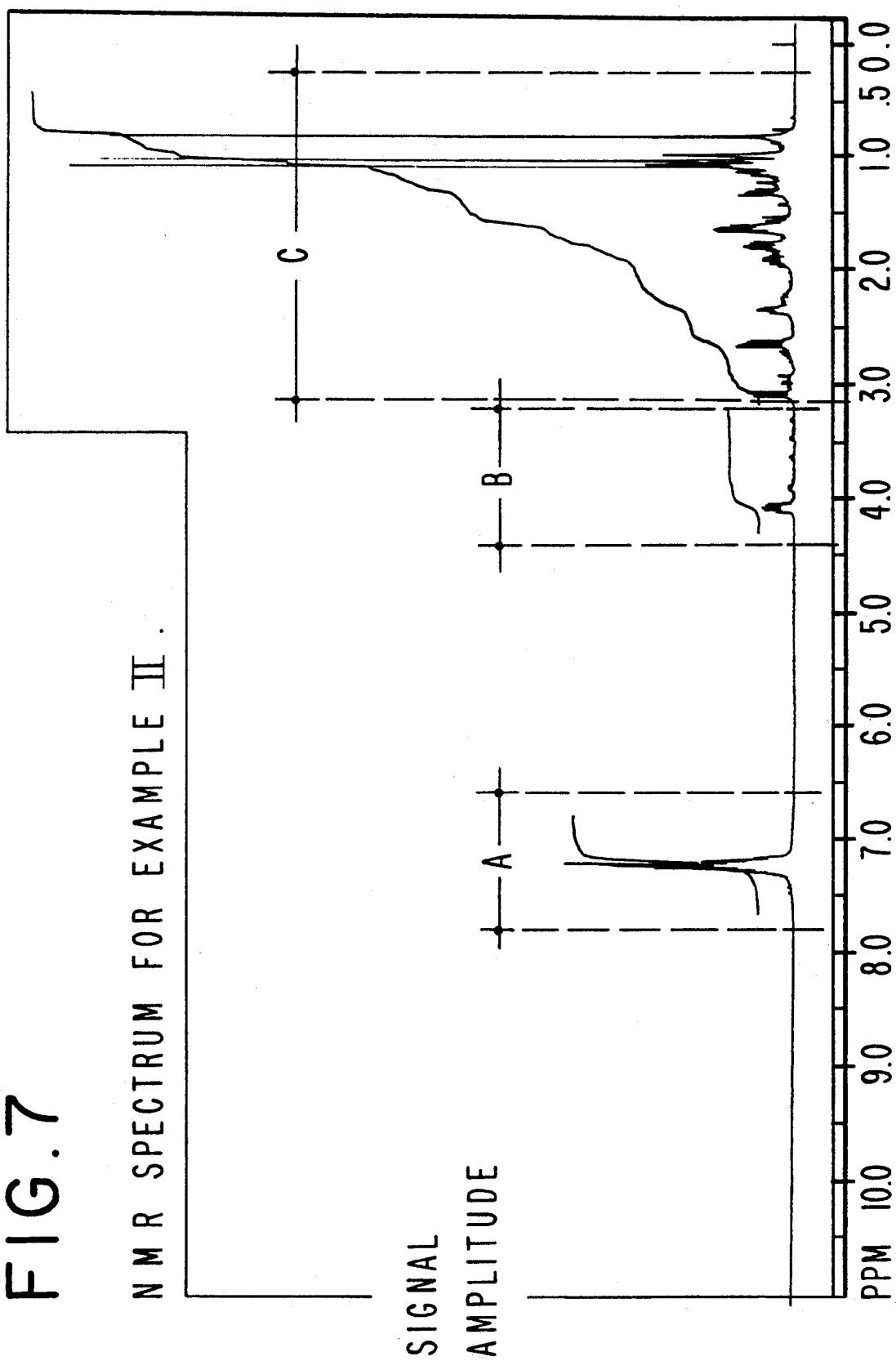
FIG. 7 NMR SPECTRUM FOR EXAMPLE II.

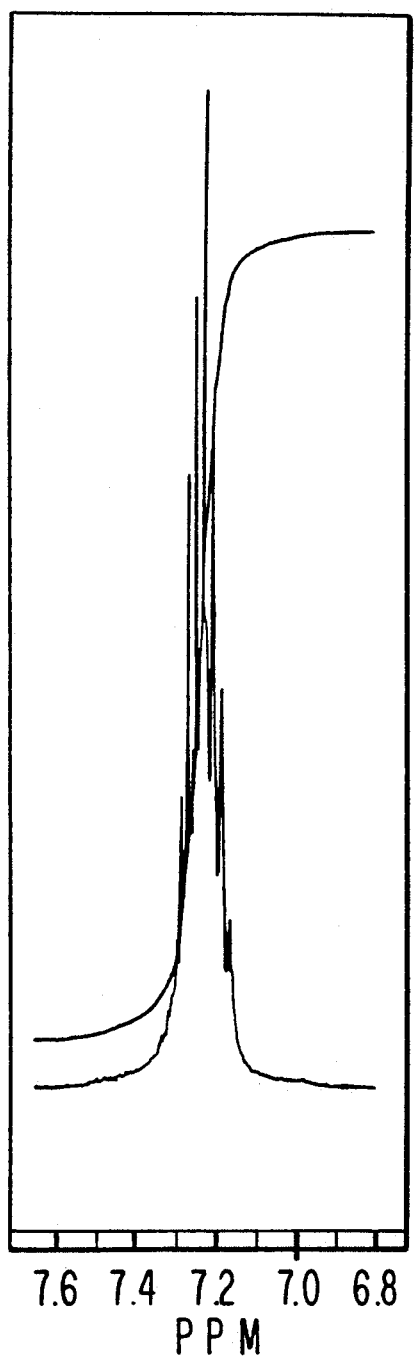
FIG.7-A
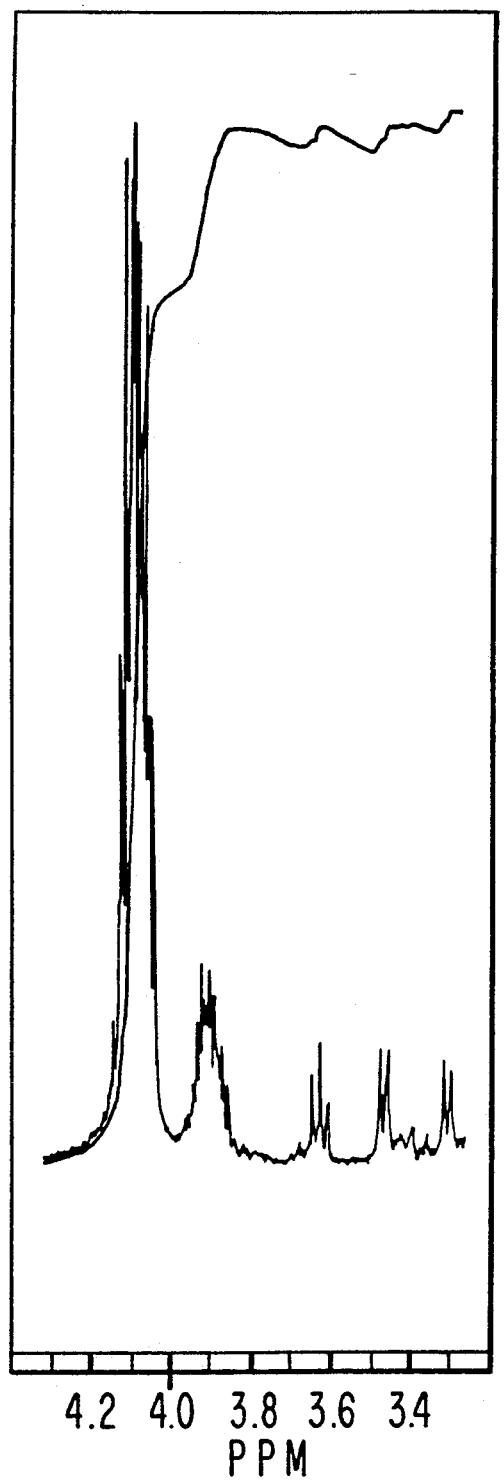
FIG.7-B

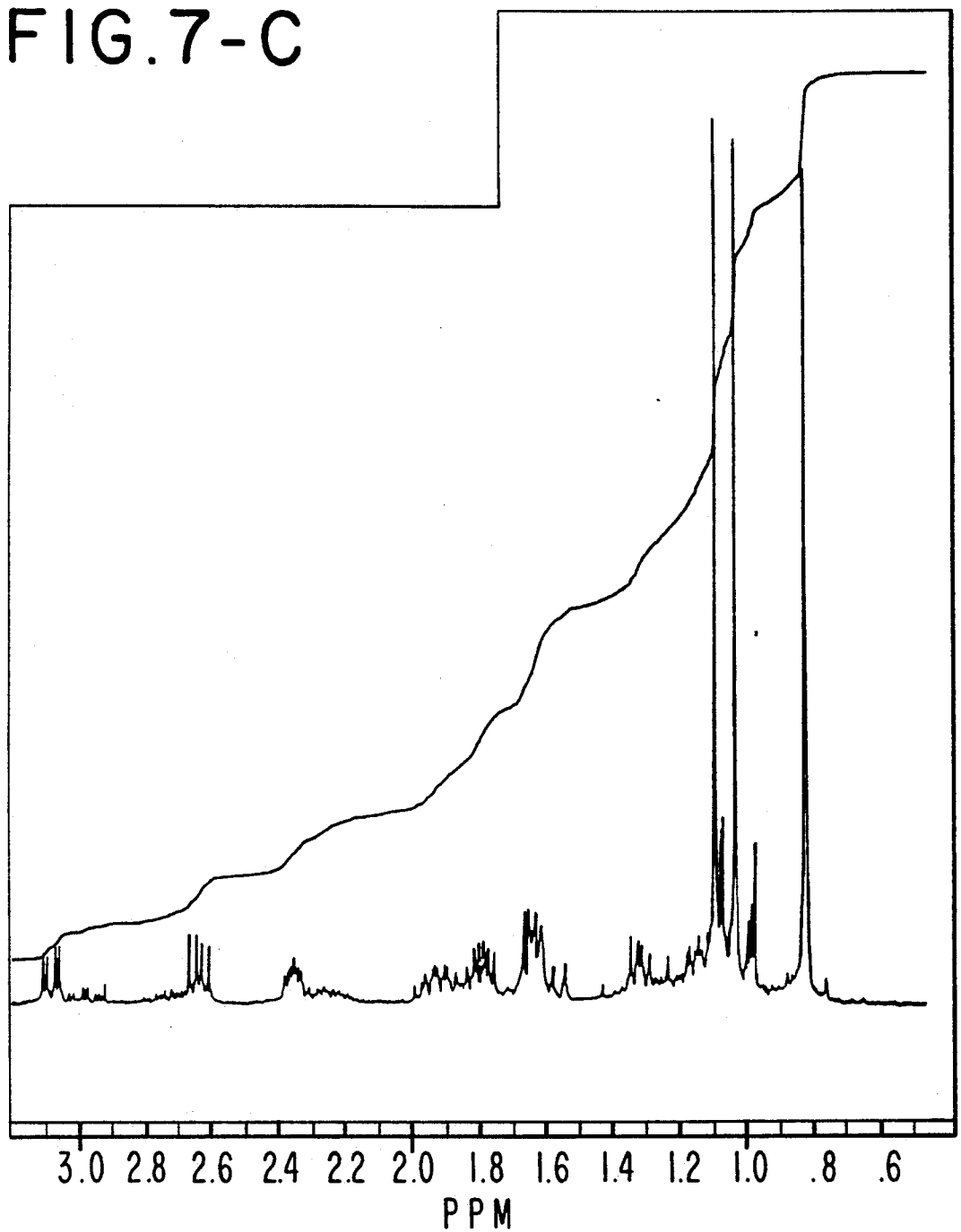
FIG.7-C

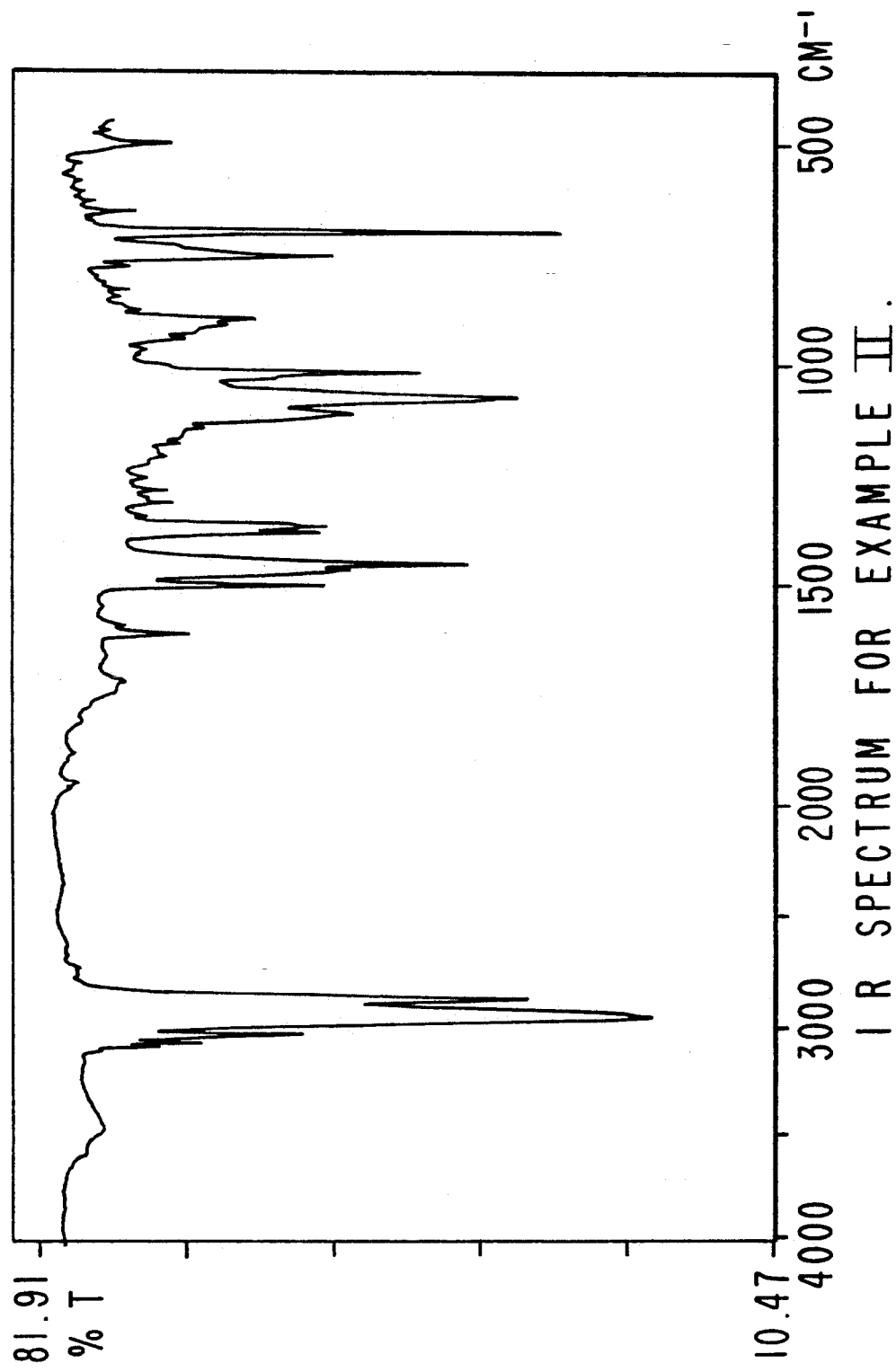

GC PROFILE FOR EXAMPLE III.

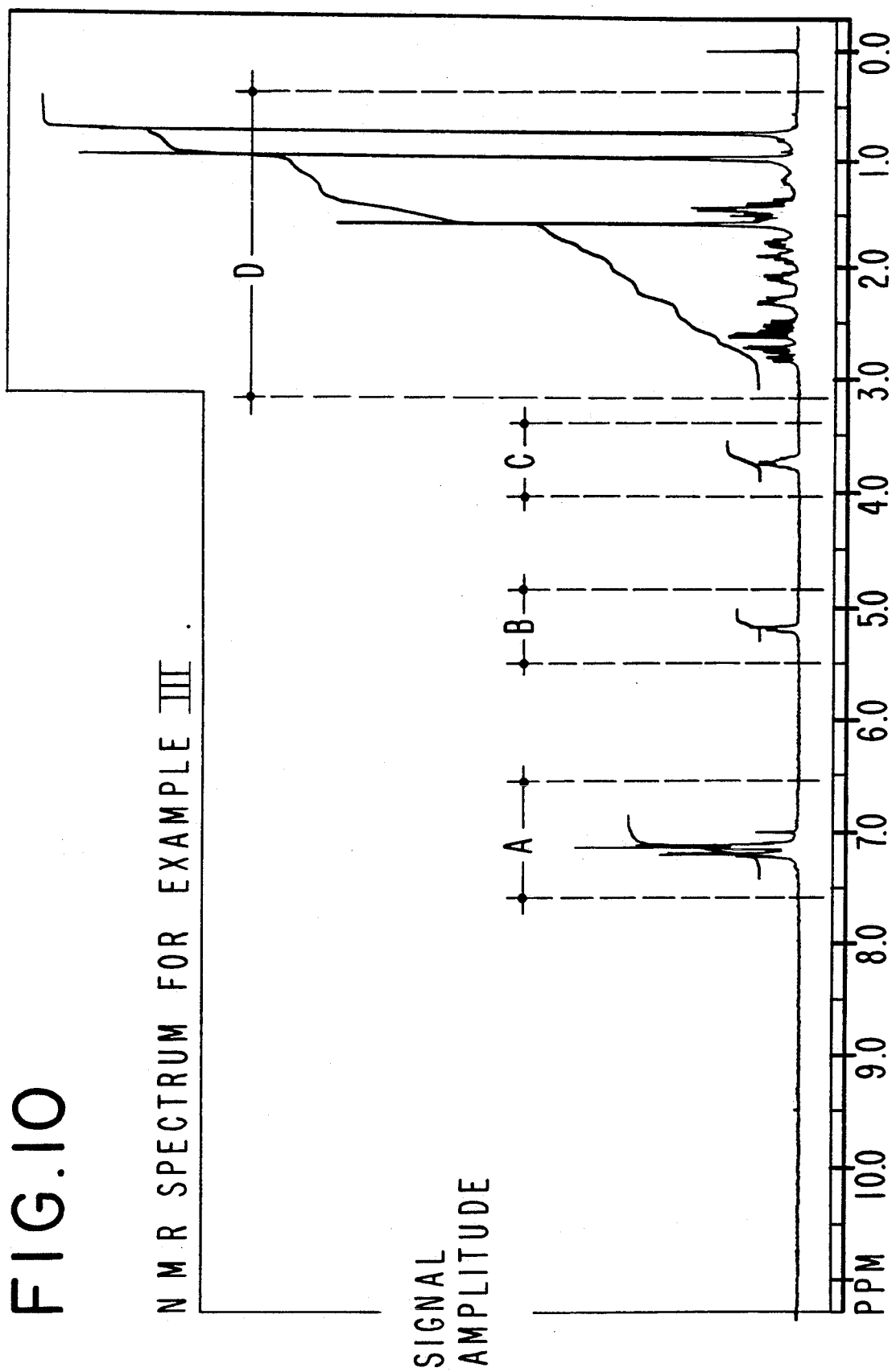
FIG. 10 NMR SPECTRUM FOR EXAMPLE III

FIG.10-A
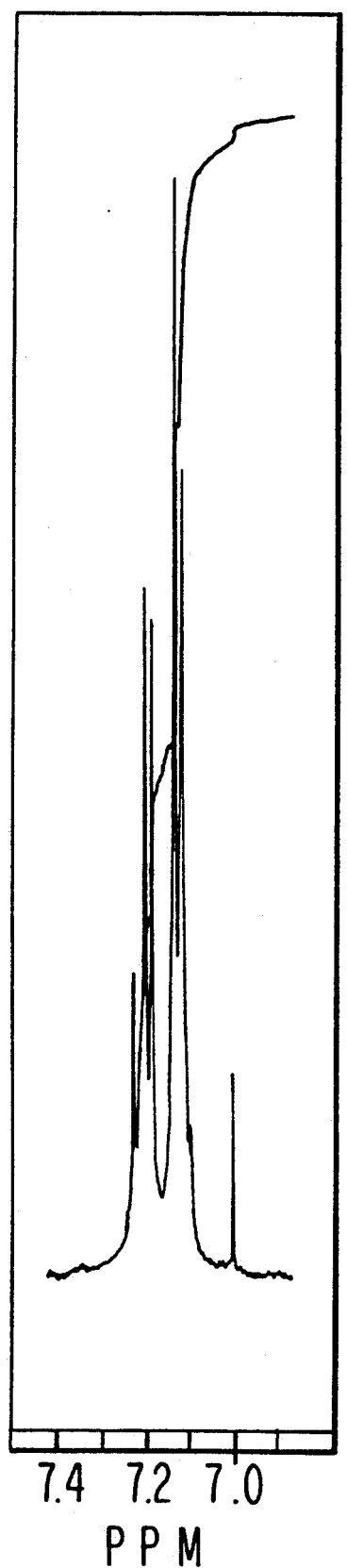
PPM

FIG.10-B
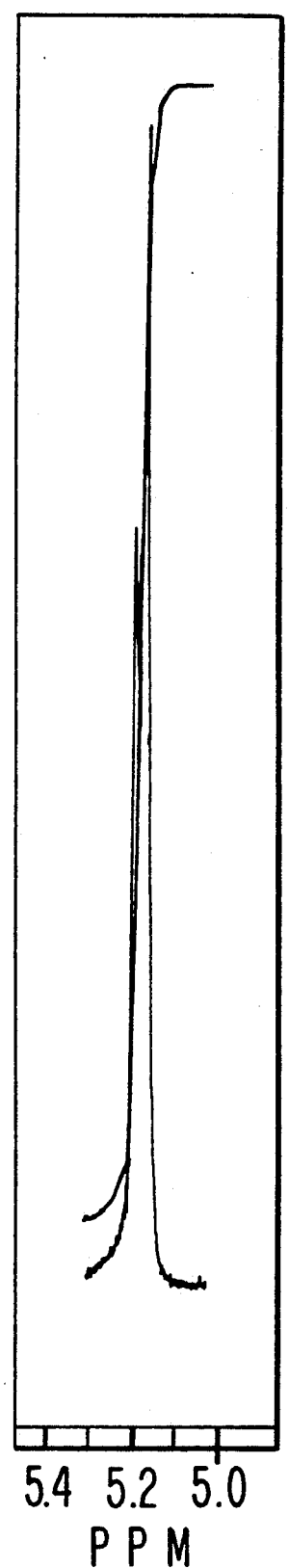
FIG.10-C
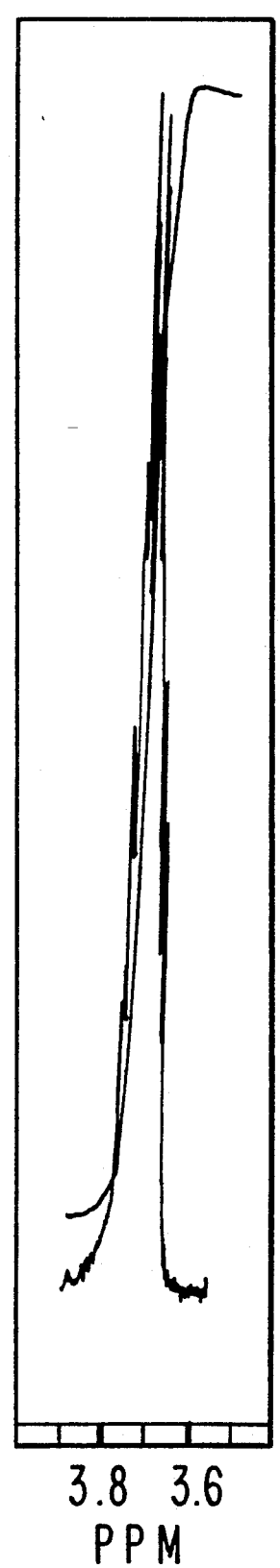

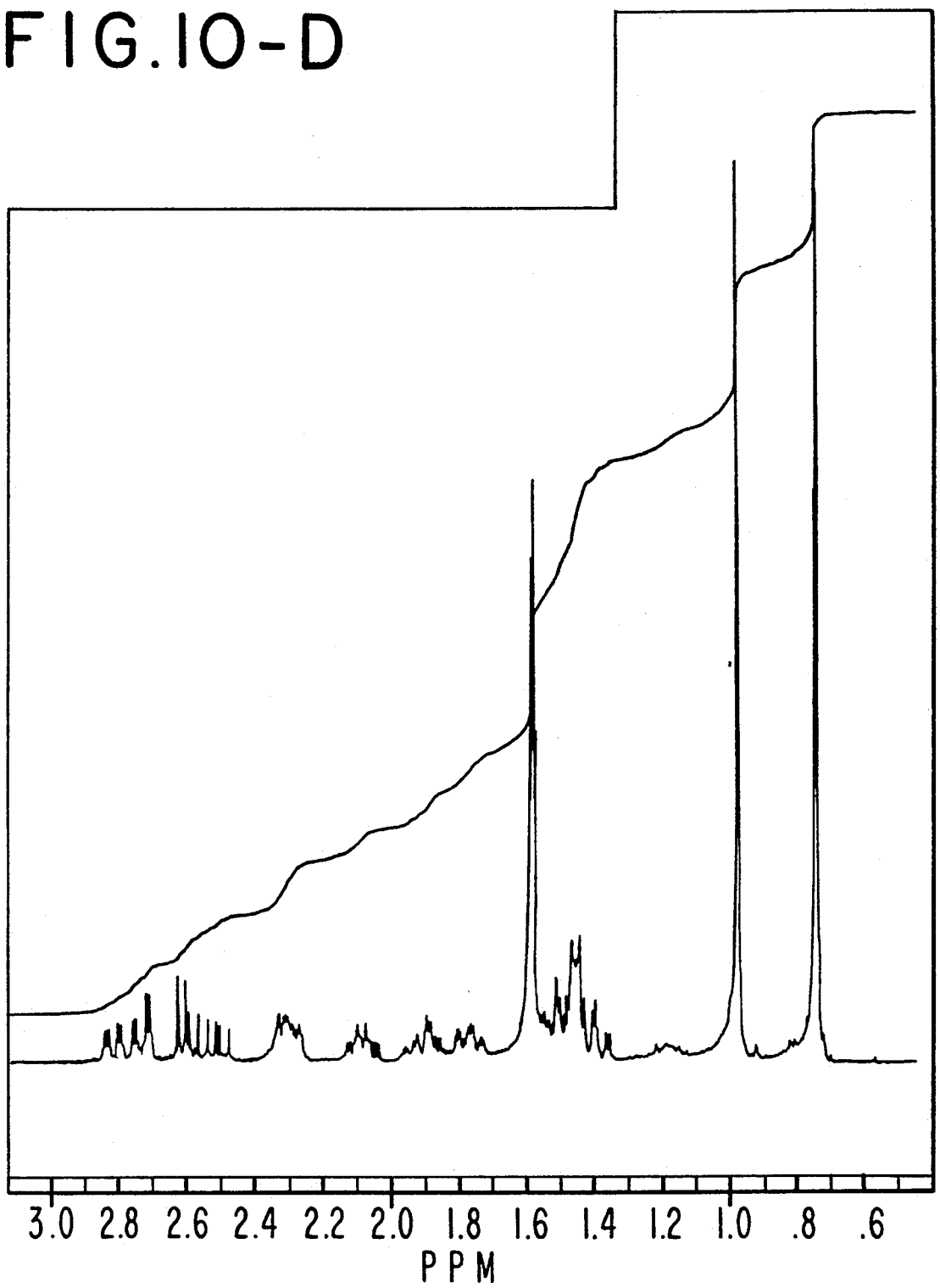
FIG.10-D

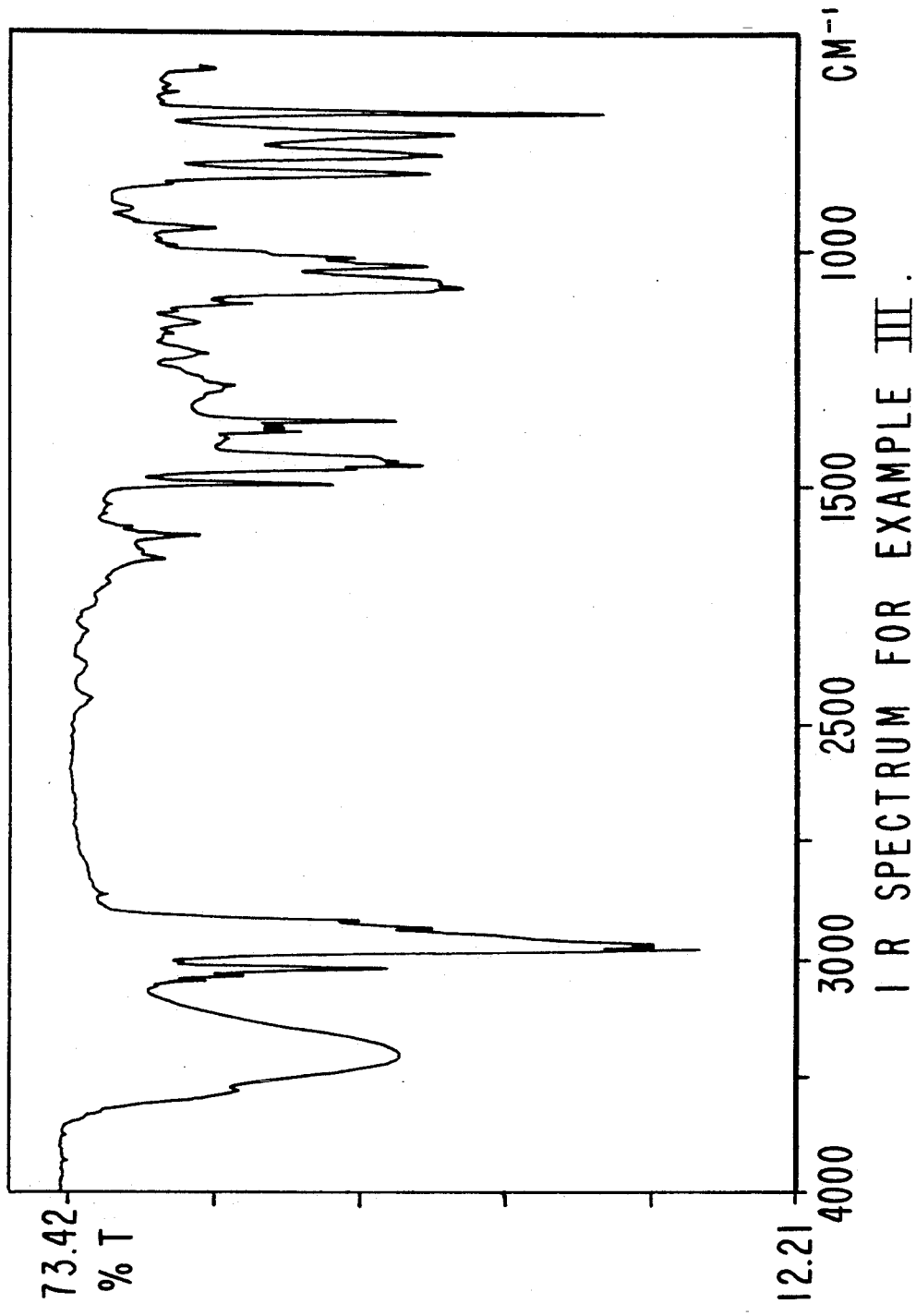

GC PROFILE FOR EXAMPLE IV.

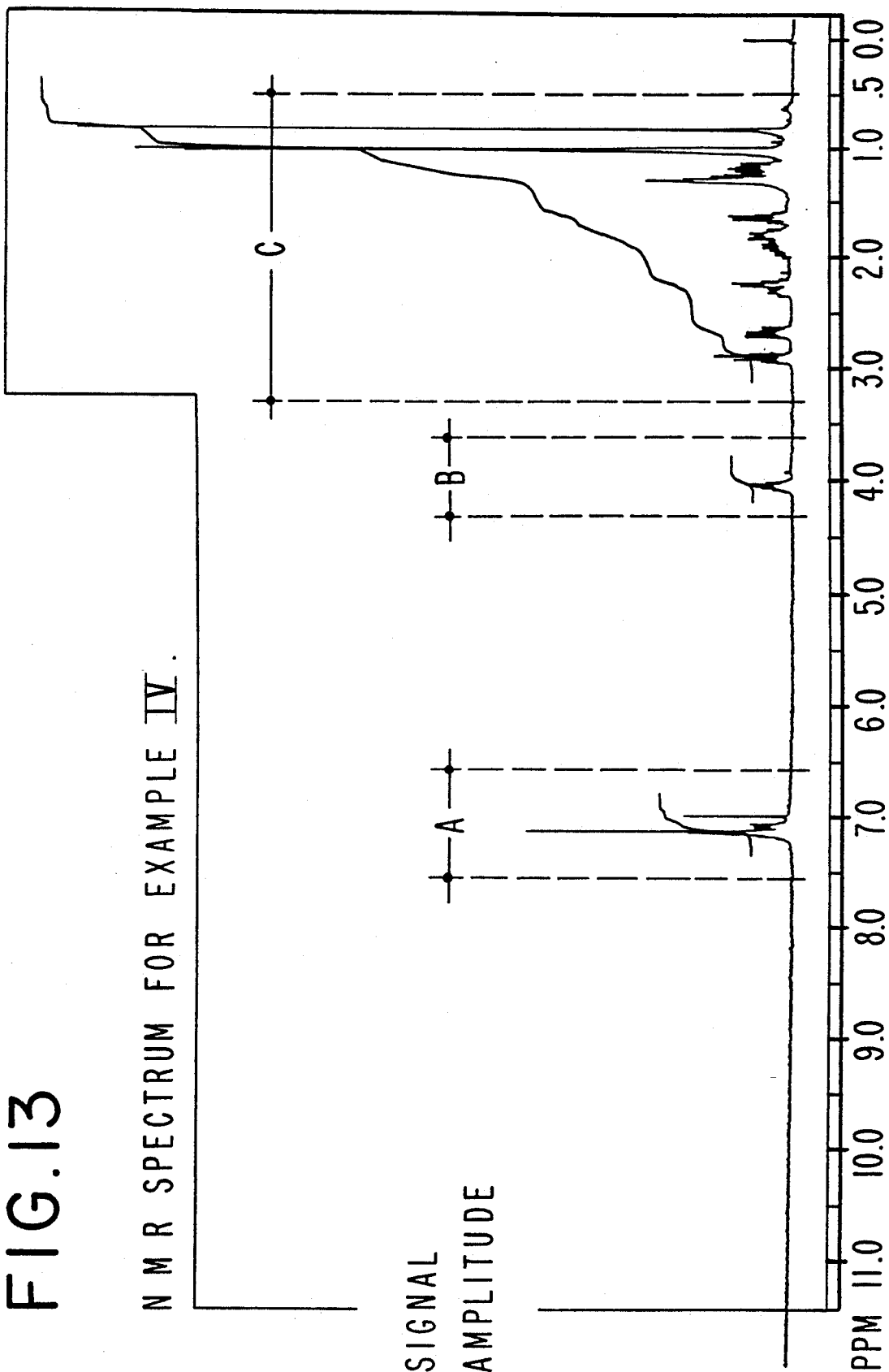

FIG.13-A
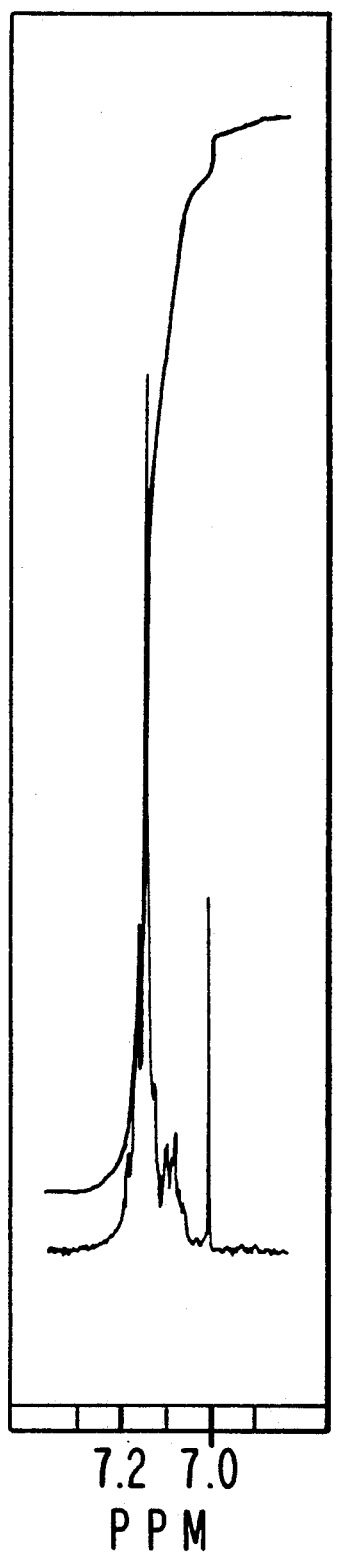
7.2  7.0
PPM
FIG.13-B
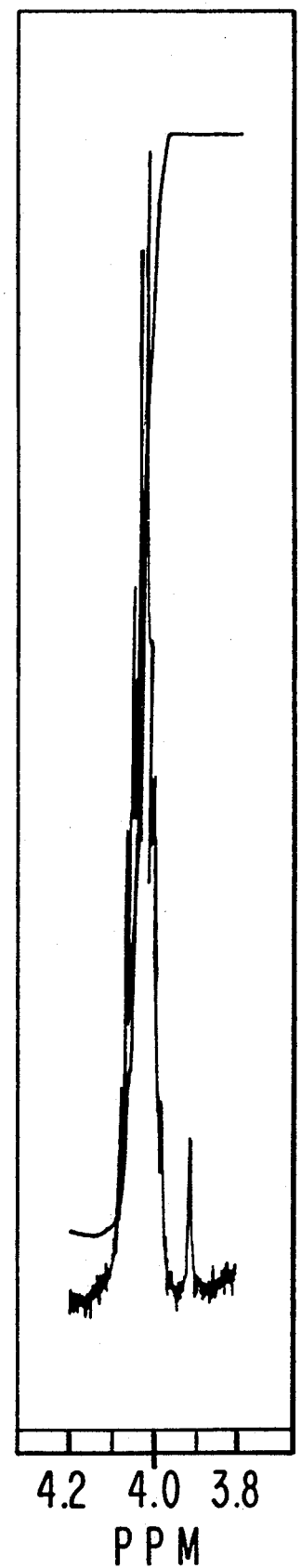
4.2  4.0  3.8
PPM

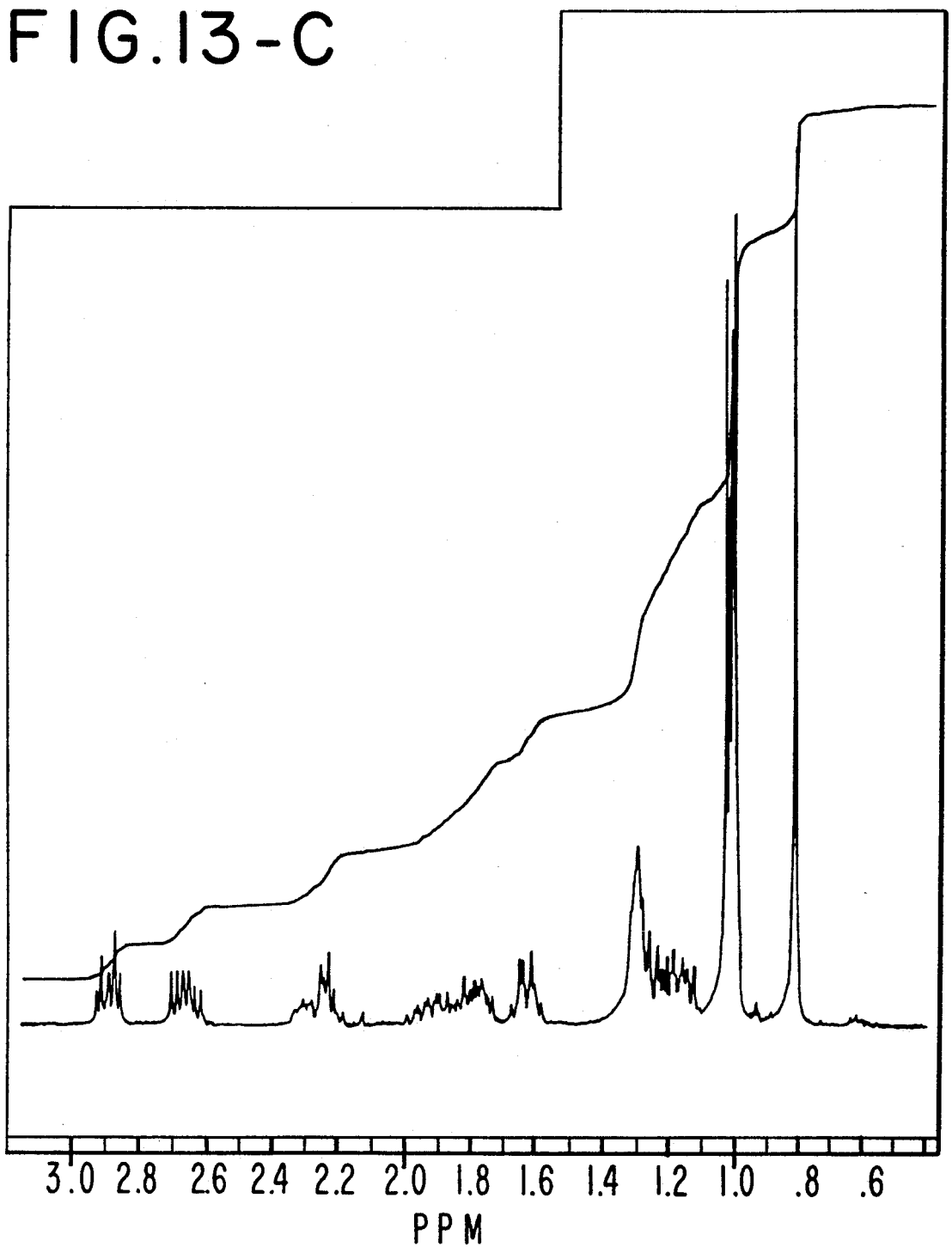
FIG.13-C

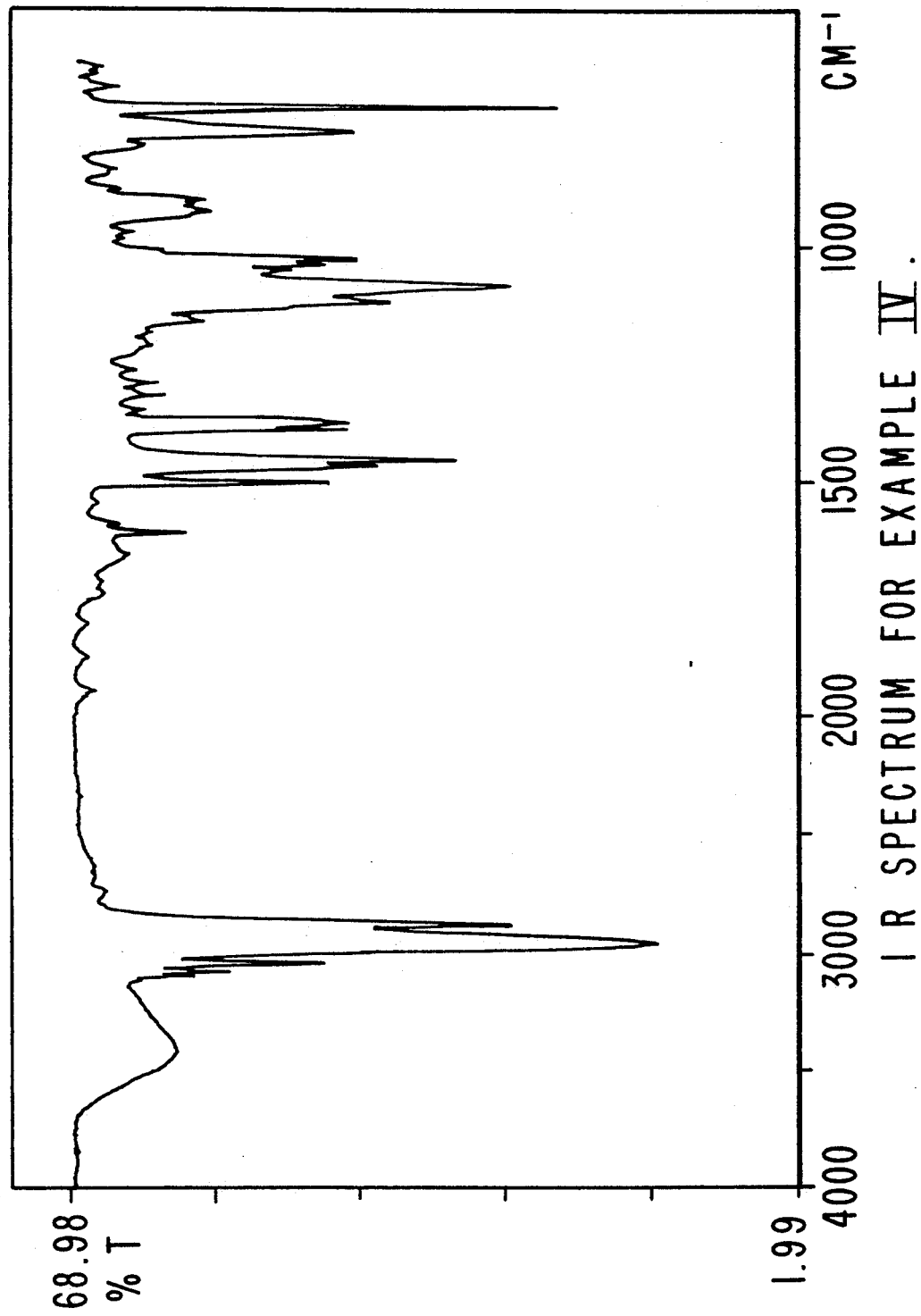
FIG.14 IR SPECTRUM FOR EXAMPLE IV.

GC PROFILE FOR EXAMPLE V.

NMR SPECTRUM FOR EXAMPLE V.

FIG.17 IR SPECTRUM FOR EXAMPLE V.

G.C. PROFILE FOR EXAMPLE VI.

IR SPECTRUM FOR EXAMPLE VI, PEAK 182 OF FIG. 18

FIG. 21 NMR SPECTRUM FOR EXAMPLE VI, PEAK 183 OF FIG. 18

GC SPECTRUM FOR EXAMPLE VII.

FIG. 26 NMR SPECTRUM FOR EXAMPLE VII.

FIG. 27 IR SPECTRUM FOR EXAMPLE VII.

GC PROFILE FOR EXAMPLE VIII.

FIG. 29 NMR SPECTRUM FOR EXAMPLE VIII, PEAK 2806 OF FIG. 28

FIG. 30 NMR SPECTRUM FOR EXAMPLE VIII, PEAK 2802 OF FIG. 28

FIG. 31 NMR SPECTRUM FOR EXAMPLE VIII, PEAK 2800 OF FIG. 28

MIXTURES OF ARYL OXABICYCLOOCTANE DERIVATIVES, MIXTURES OF PHENYL NORBORNANE DERIVATIVES, PROCESSES FOR PREPARING SAME, PERFUMERY USES THEREOF AND INTERMEDIATES USED IN SAID PROCESSES

This is a divisional of U.S. patent application Ser. No. 982,380, filed Nov. 25, 1992.

BACKGROUND OF THE INVENTION

Our invention relates to aryl oxabicyclooctane derivatives and phenyl norbornane derivatives defined according to the structures:

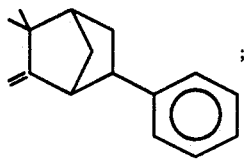
;

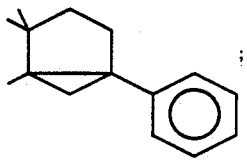
;

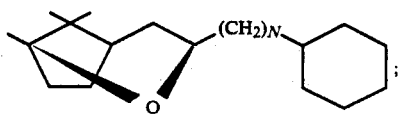
;

and

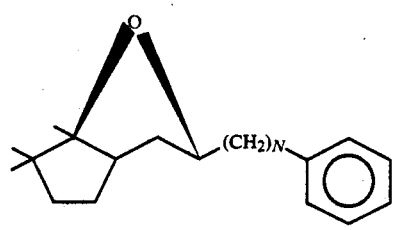

wherein N is 1 or 2, processes for preparing same, perfumery uses thereof and intermediates used in said processes which intermediates are defined according to the structures:

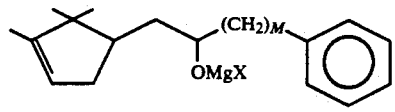

and

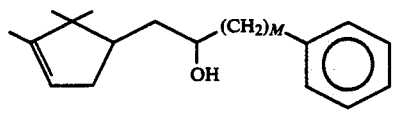

wherein M is 0, 1 or 2 and X is chloro or bromo.

Sweaty, animalic, amber, musky, dry camphoraceous and woody-peppery aromas, with green, herbaceous, sweaty, animalic, cigar box-like and woody topnotes are particularly desirable in augmenting or enhancing the aroma of perfume compositions, colognes and perfumed articles (e.g., solid or liquid, anionic, cationic, nonionic or zwitterionic detergents, fabric softener compositions, fabric softener articles, hair preparations, cosmetic powders and perfumed polymers).

Compounds having the oxabicyclooctane nucleus have been known for use in augmenting or enhancing the aroma of perfume compositions, perfumed articles and colognes for a number of years. Such compounds are disclosed in U.S. Pat. No. 4,269,862 and U.S. Pat. No. 5,087,707. Furthermore, Cineole is disclosed by Arctander "Perfume and Flavor Chemicals" (Aroma Chemicals) at Monograph 616 to have a eucalyptus aroma (its common name is "eucalyptol").

Nothing in the prior art however discloses the aryl oxabicyclooctane derivatives and phenyl norbornane derivatives of our invention for their organoleptic utilities.

However, Beilstein H6,591 (EIII6/2771) discloses the compound having the structure:

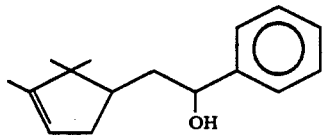

prepared from Alpha-pinen oxide and alpha-campholenaldehyde. The Beilstein reference does not show that the compound can be further cyclized, however.

2-Phenyl-2-norbornene having the structure:

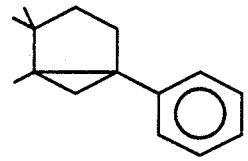

(CAS 42114-13-6) is disclosed by Kropp, J.Amer.-Chem.Soc., 1973, Vol. 95(14), pages 4611–19 [title: "Photochemistry of CycloAlkenes.VIII] 2-Phenyl-2-norbornene and 2-phenyl-2-bornene".

No disclosure of the use of the compound having the structure:

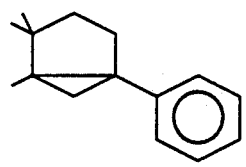

in perfumery is disclosed. No disclosure of the mixture of the compounds having the structures:

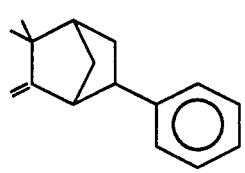

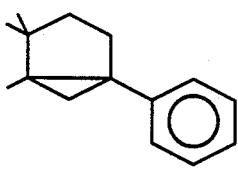

is disclosed in the prior art.

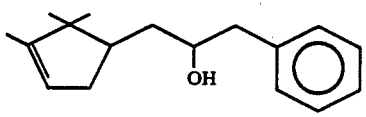

(conditions: SE-30 column programmed at 150°–220° C. at 8° C. per minute).

FIG. 2 is the NMR spectrum for the compound having the structure:

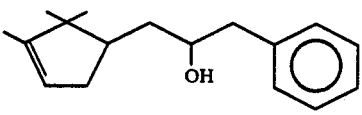

prepared according to Example I.

FIGS. 2A, 2B, 2C and 2D are enlargements of sections "A", "B", "C" and "D" of the NMR spectrum of FIG. 2, respectively.

FIG. 3 is the infra-red spectrum for the compound having the structure:

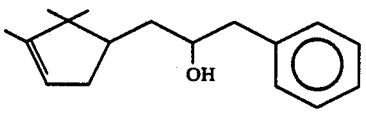

produced according to Example I.

Figure 4:
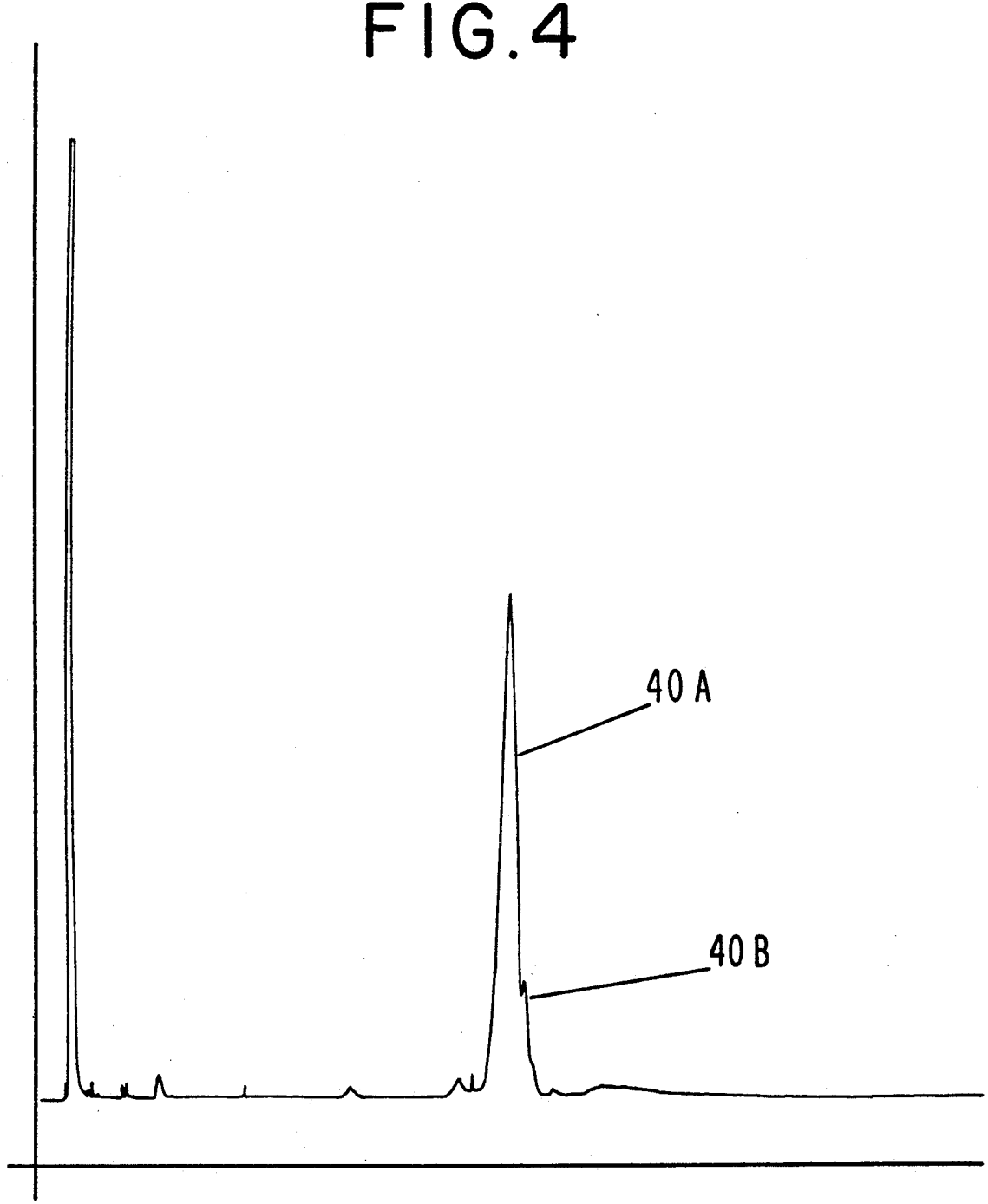

FIG. 4 is the GC profile of the reaction product of Example II containing the compounds having the structures:

and

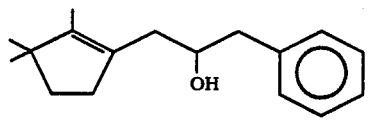

(Conditions: SE-30 column programmed at 150°–220° C. at 8° C. per minute).

FIG. 5 is the NMR spectrum for the compound having the structure:

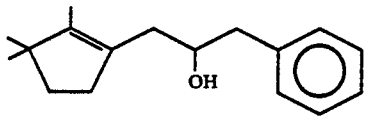

produced according to Example II.

FIGS. 5A, 5B and 5C are enlargements of sections "A", "B" and "C", respectively, of the NMR spectrum of FIG. 5.

FIG. 6 is the infra-red spectrum for the compound having the structure:

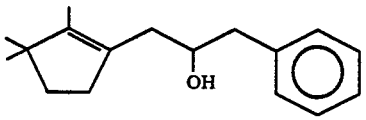

prepared according to Example II.

FIG. 7 is the NMR spectrum for the mixture of compounds having the structures:

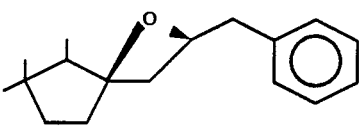

and

produced according to Example II.

FIGS. 7A, 7B and 7C are enlargements of sections "A", "B" and "C" of the NMR spectrum of FIG. 7.

FIG. 8 is the infra-red spectrum for the mixture of compounds having the structures:

and

prepared according to Example II.

Figure 9:
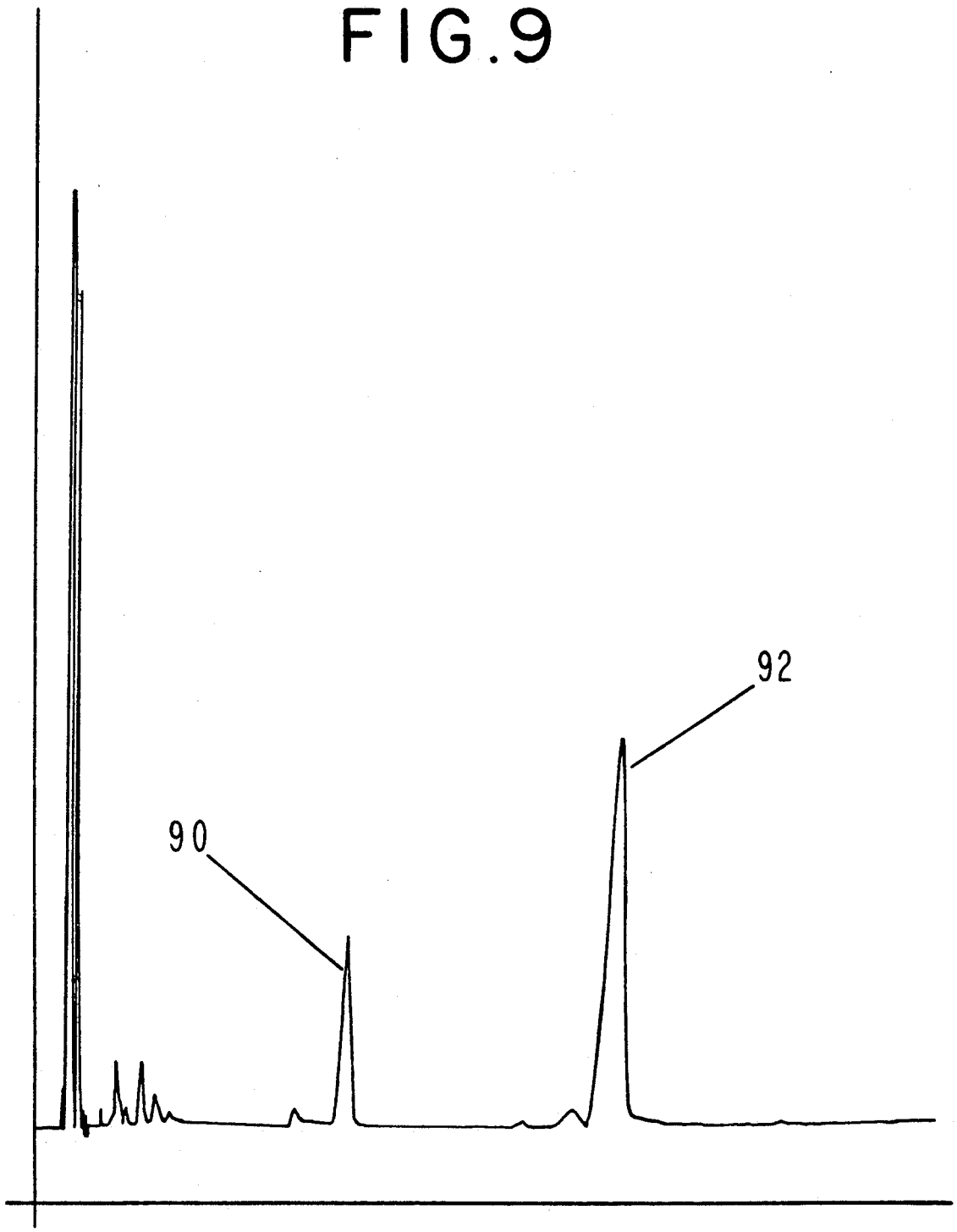

FIG. 9 is the GC profile for the reaction product of Example III containing the compound having the structure:

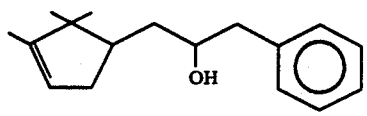

(Conditions: SE-30 column programmed at 150°–220° C. at 8° C. per minute).

FIG. 10 is the NMR spectrum for the compound having the structure:

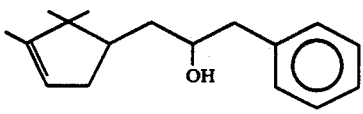

prepared according to Example III

FIGS. 10A, 10B, 10C and 10D are enlargements of sections "A", "B", "C" and "D", respectively, of the NMR spectrum of FIG. 10.

FIG. 11 is the infra-red spectrum for the compound having the structure:

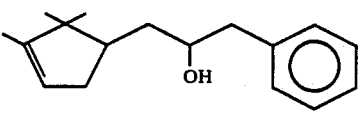

prepared according to Example III.

Figure 12:
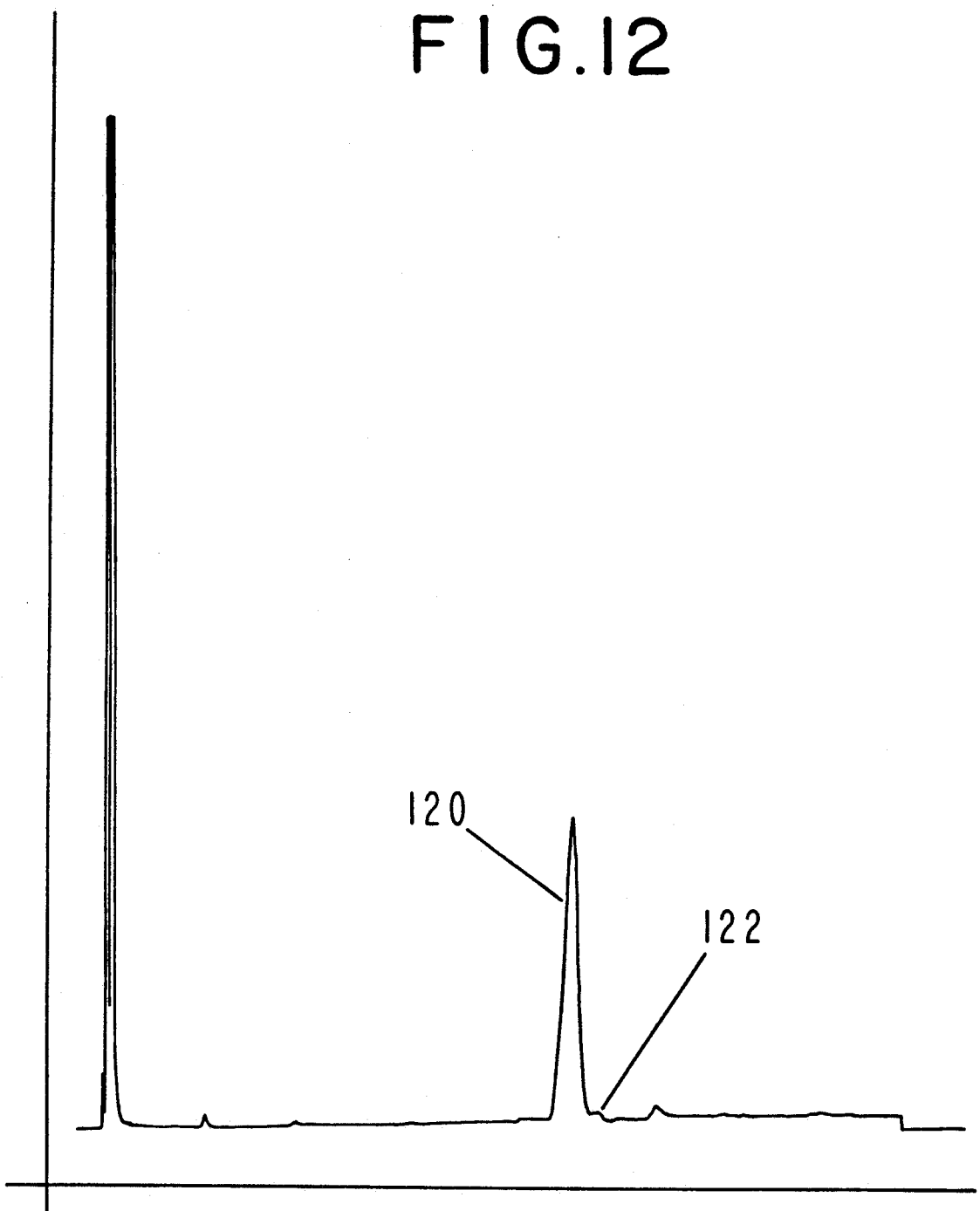

FIG. 12 is the GC profile for the reaction product of Example IV containing the compounds having the structures:

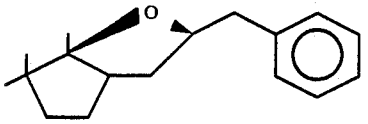

and

FIG. 13 is the NMR spectrum for the mixture of compounds having the structures:

and

prepared according to Example IV.

FIGS. 13A, 13B and 13C are enlargements of sections "A", "B" and "C" of the NMR spectrum of FIG. 13.

FIG. 14 is the infra-red spectrum for the mixture of compounds having the structures:

and

produced according to Example IV.

Figure 15:
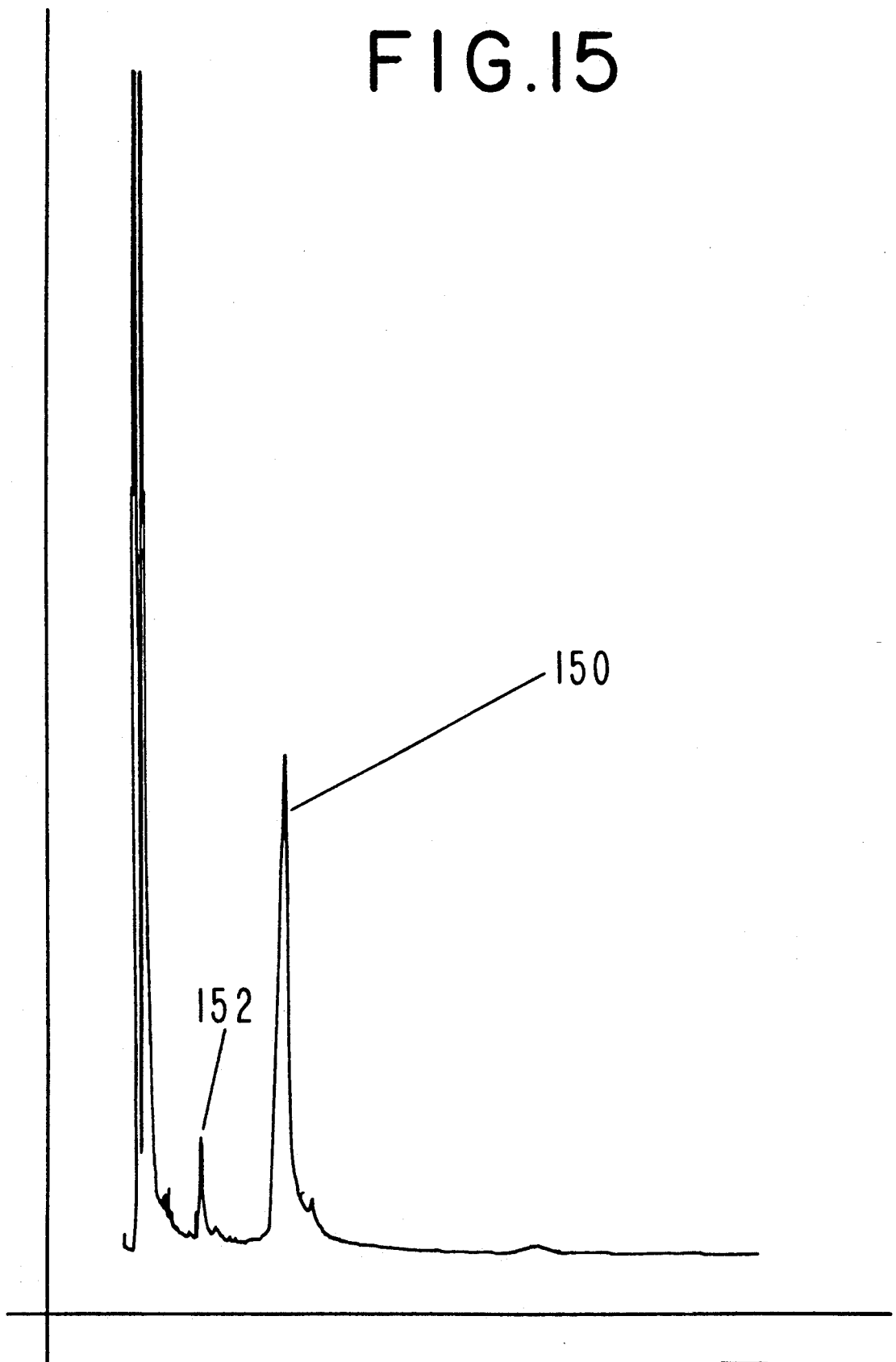

FIG. 15 is the GC spectrum for the reaction product of Example V containing the compounds having the structures:

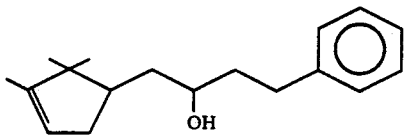

and

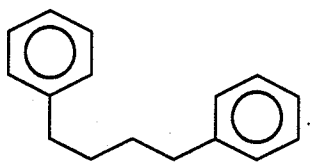

Figure 16:
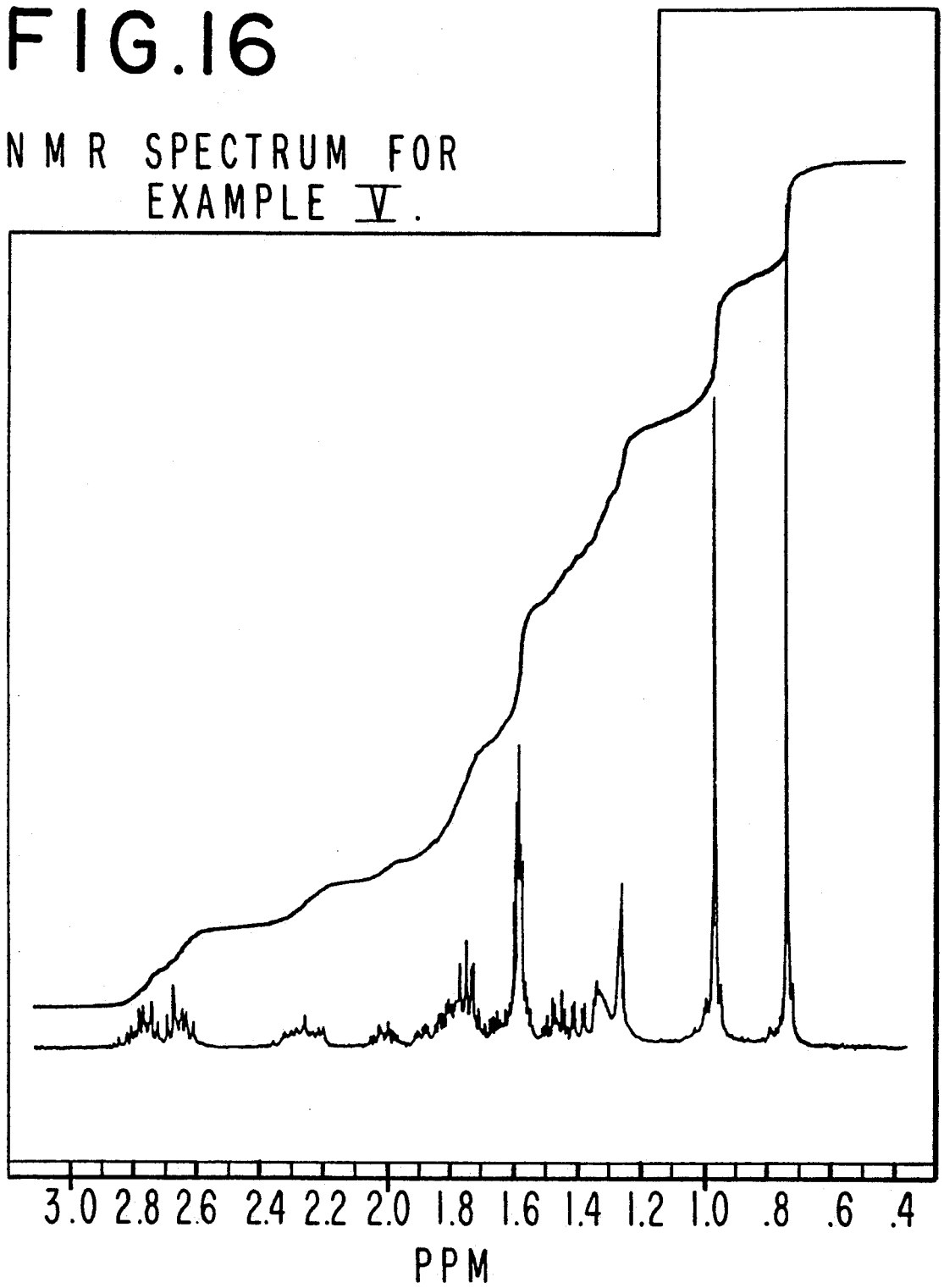

FIG. 16 is the NMR spectrum for the compound having the structure:

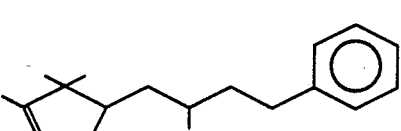

produced according to Example V.

Figure 17:
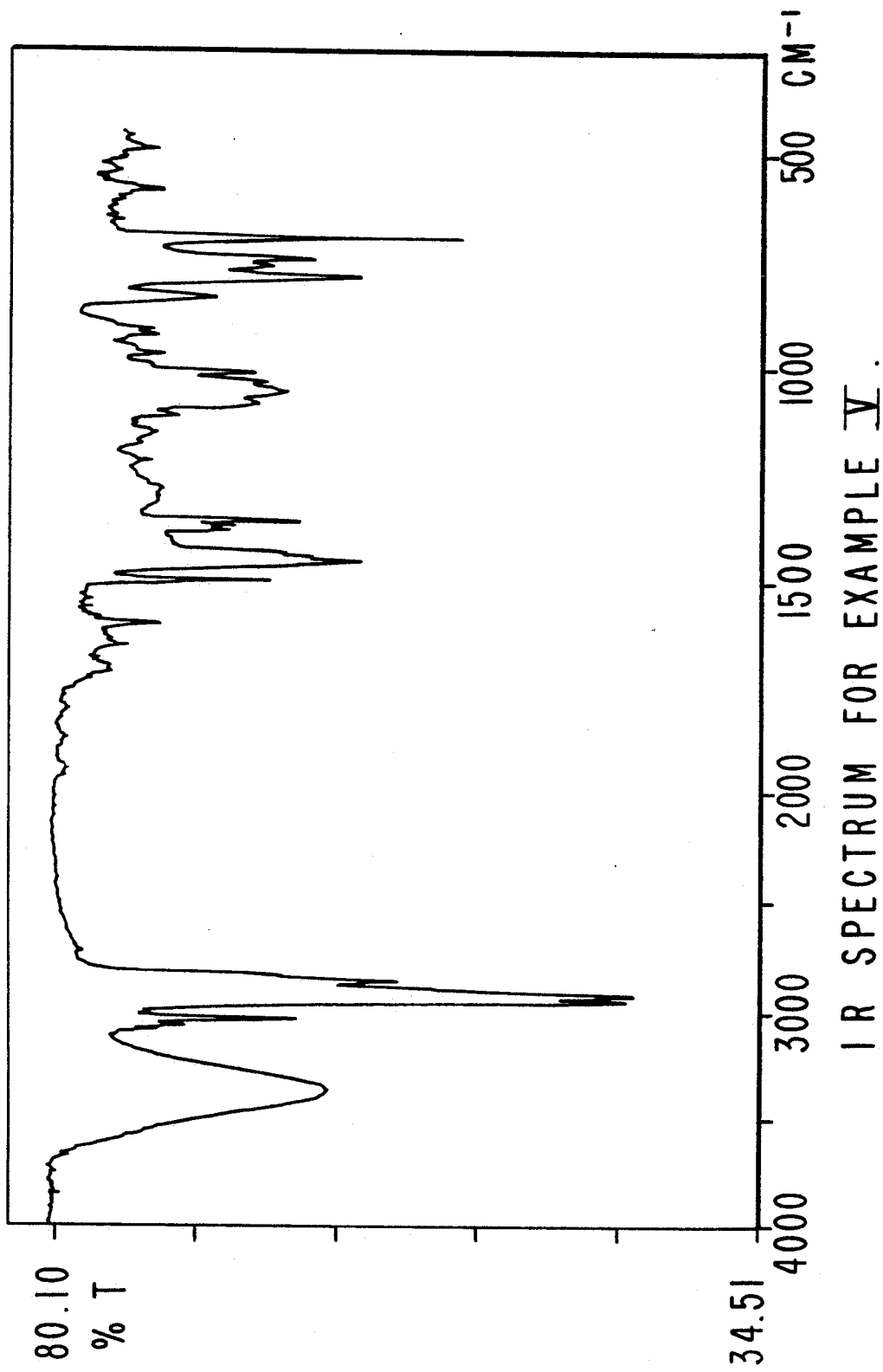

FIG. 17 is the infra-red spectrum for the compound having the structure:

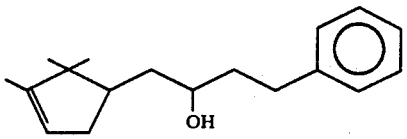

produced according to Example V.

Figure 18:
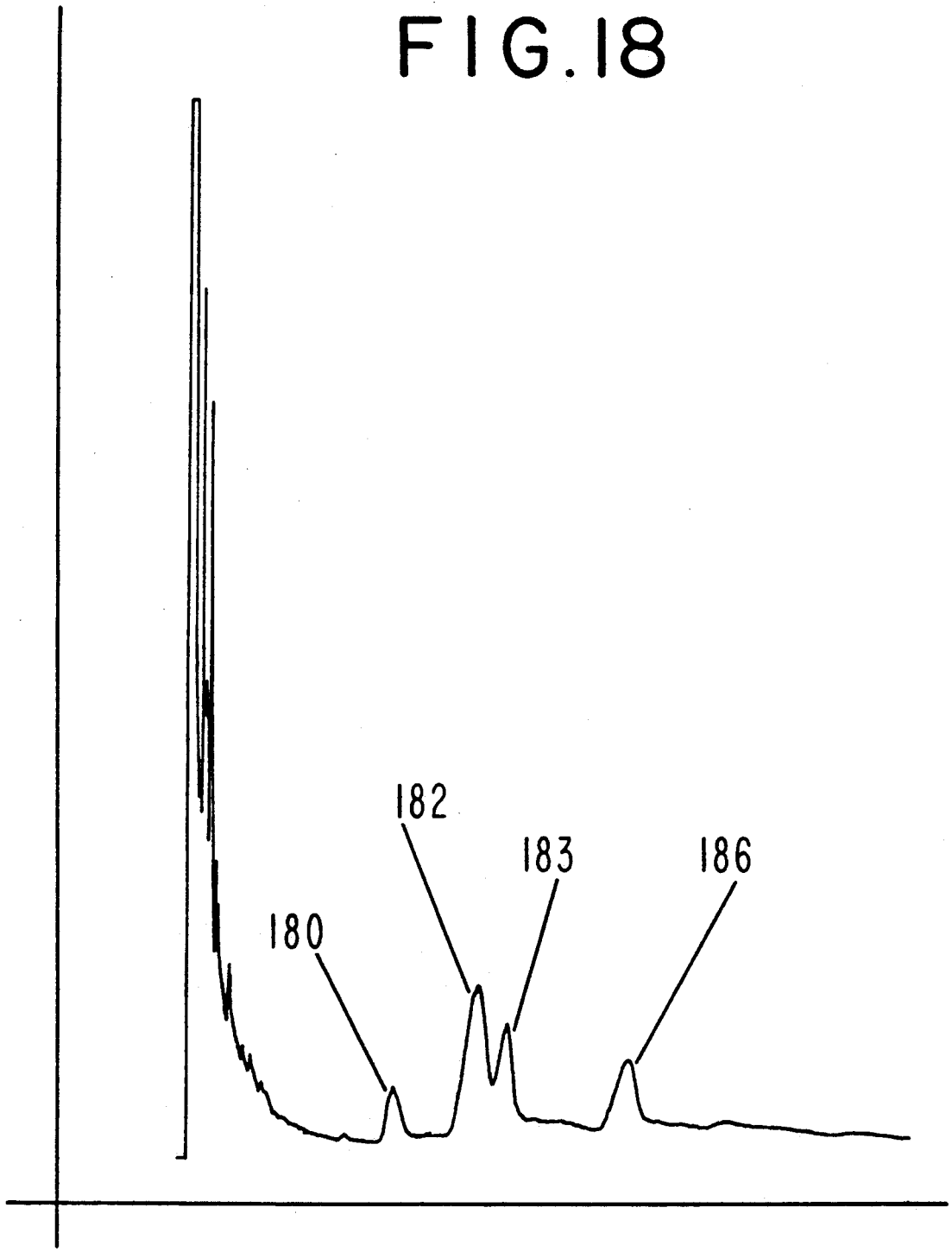

FIG. 18 is the GC spectrum for the reaction product of Example VI containing the compounds having the structures:

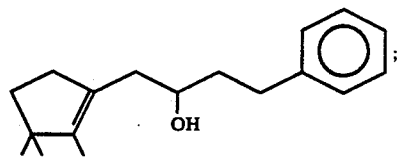

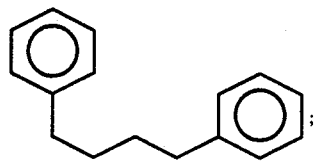

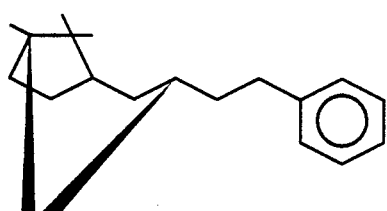

and

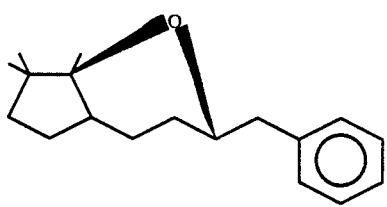

(Conditions: SE-30 column programmed at 180° C. isothermal).

Figure 19:
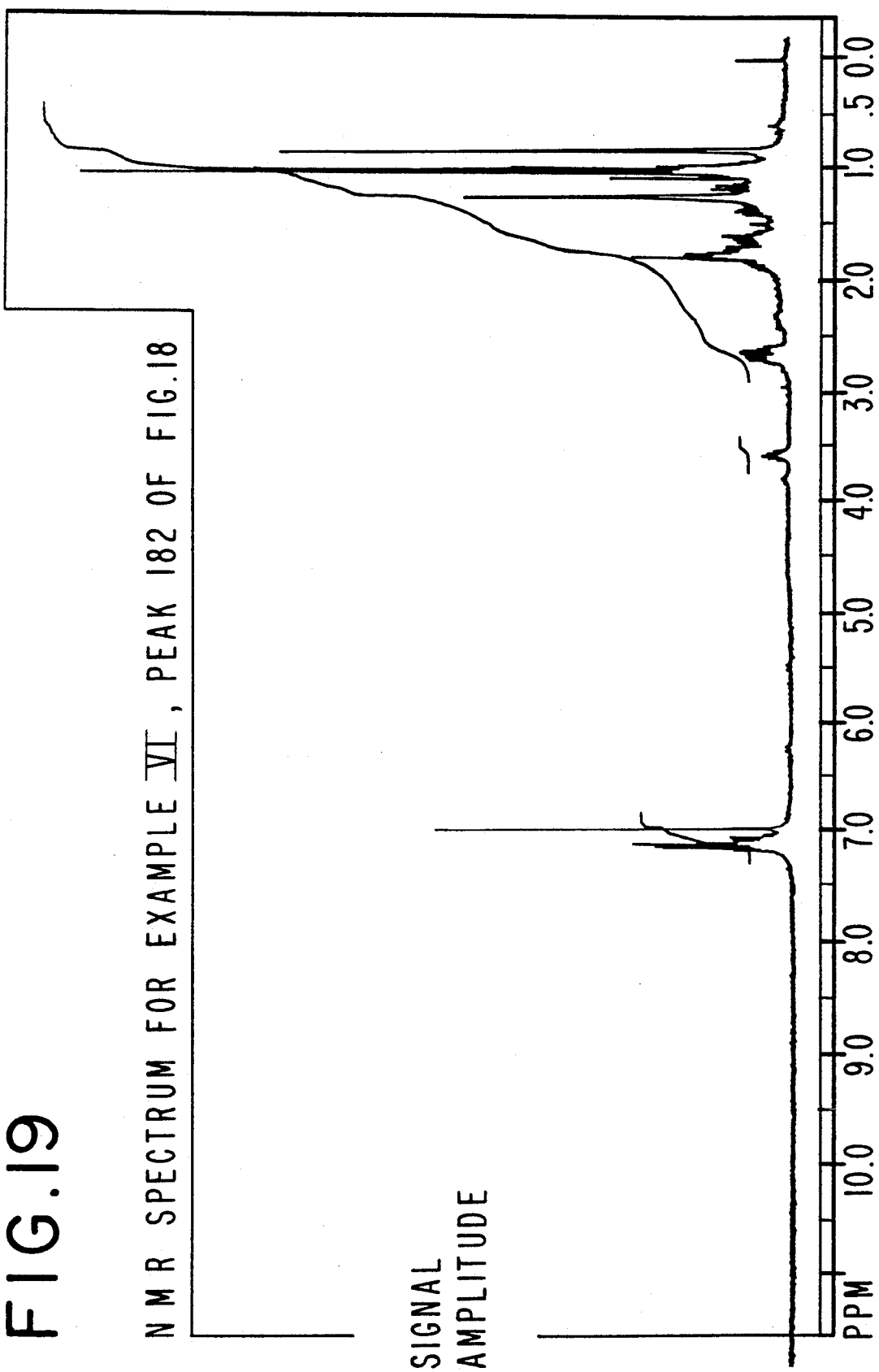

FIG. 19 is the NMR spectrum for the peak indicated by reference numeral 182 of the GC profile of FIG. 18 for the compound having the structure:

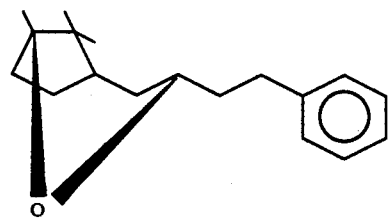

or the compound having the structure:

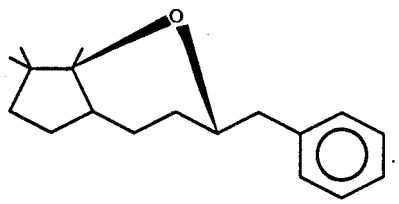

Figure 20:
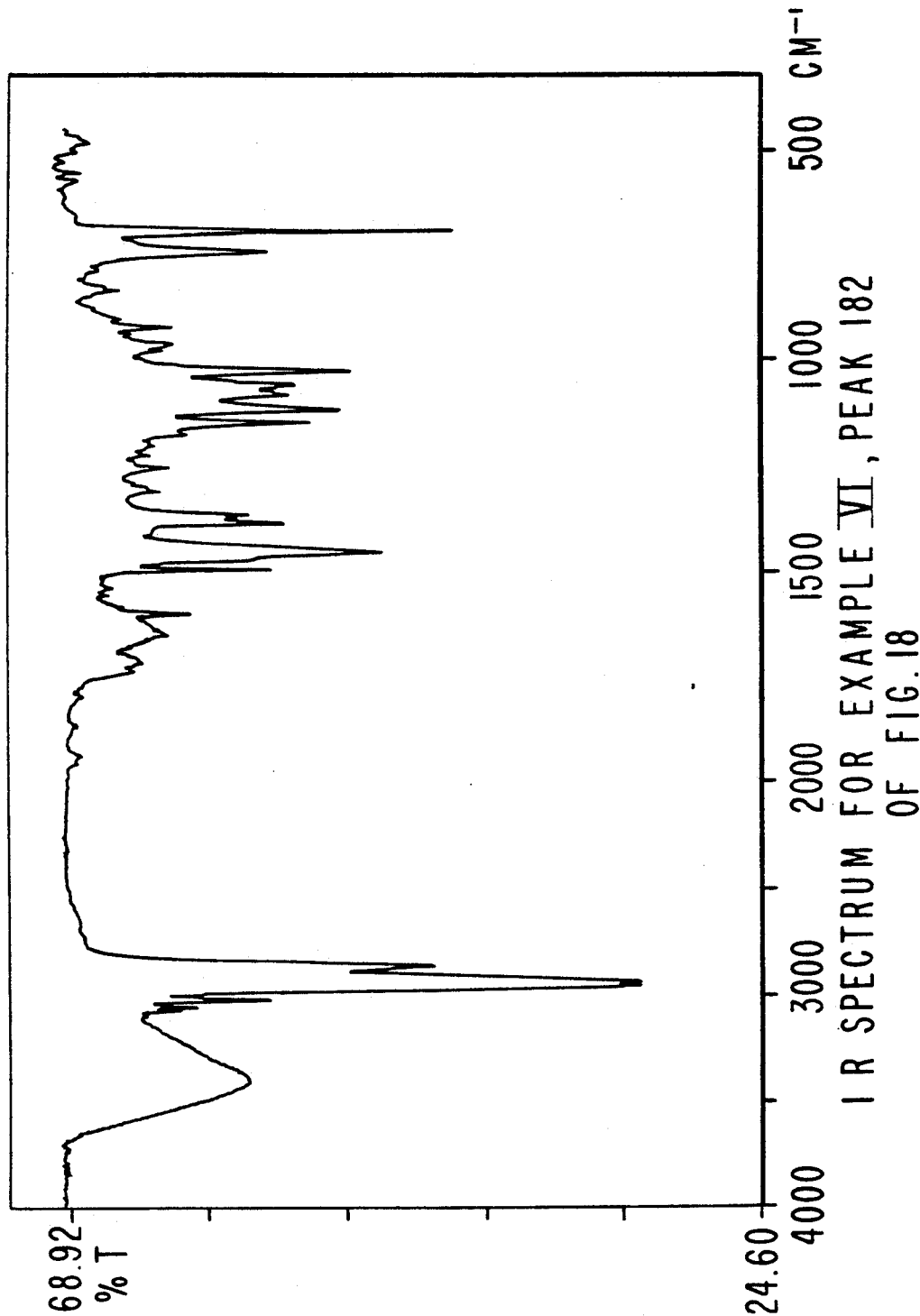

FIG. 20 is the infra-red spectrum for the peak indicated by reference numeral 182 of the GC profile of FIG. 18 for the compound having the structure:

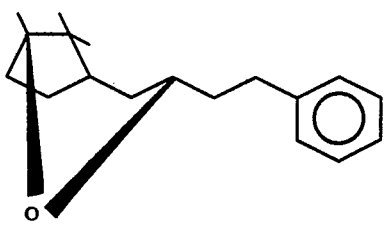

or the compound having the structure:

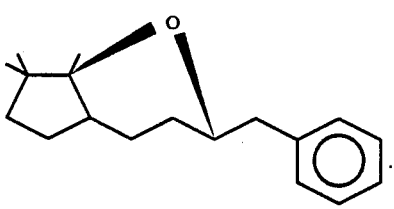

Figure 21:
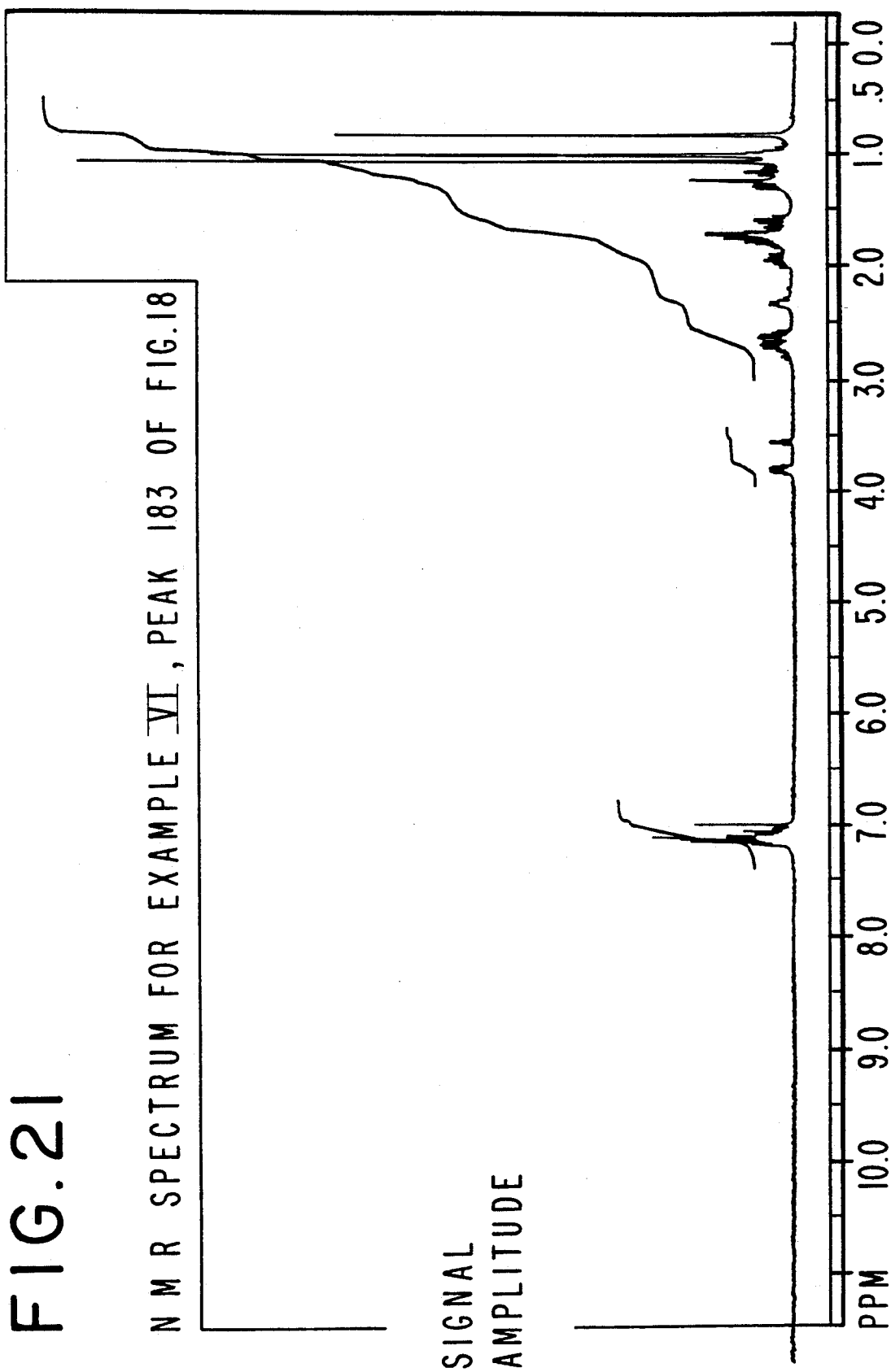

FIG. 21 is the NMR spectrum for the peak indicated by reference numeral 183 of the GC spectrum of FIG. 18 for the compound having the structure:

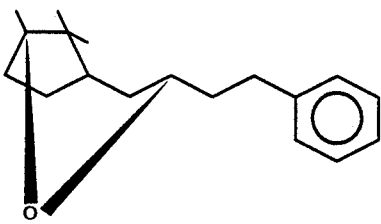

or the compound having the structure:

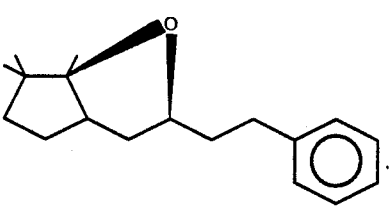

Figure 22:
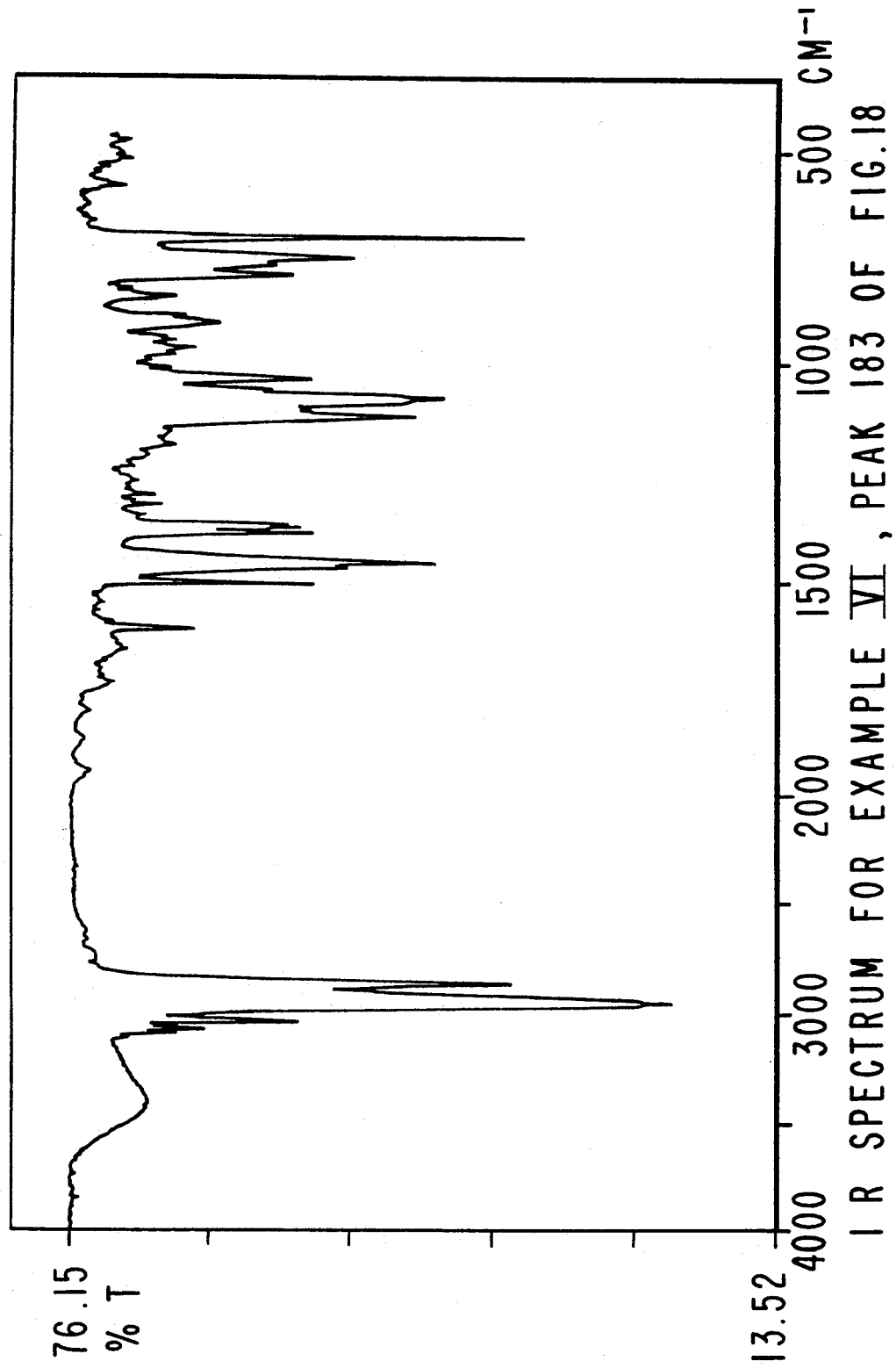

FIG. 22 is the infra-red spectrum for the peak indicated by reference numeral 183 of the GC spectrum of FIG. 18 for the compound having the structure:

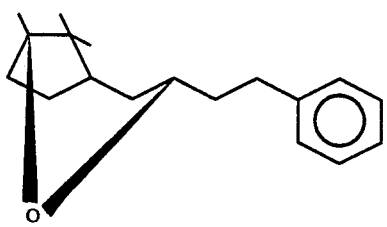

or the compound having the structure:

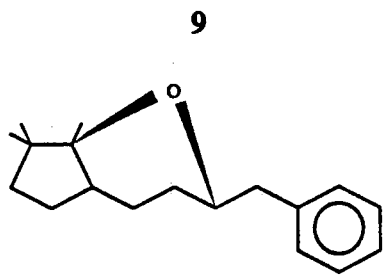

Figure 23:
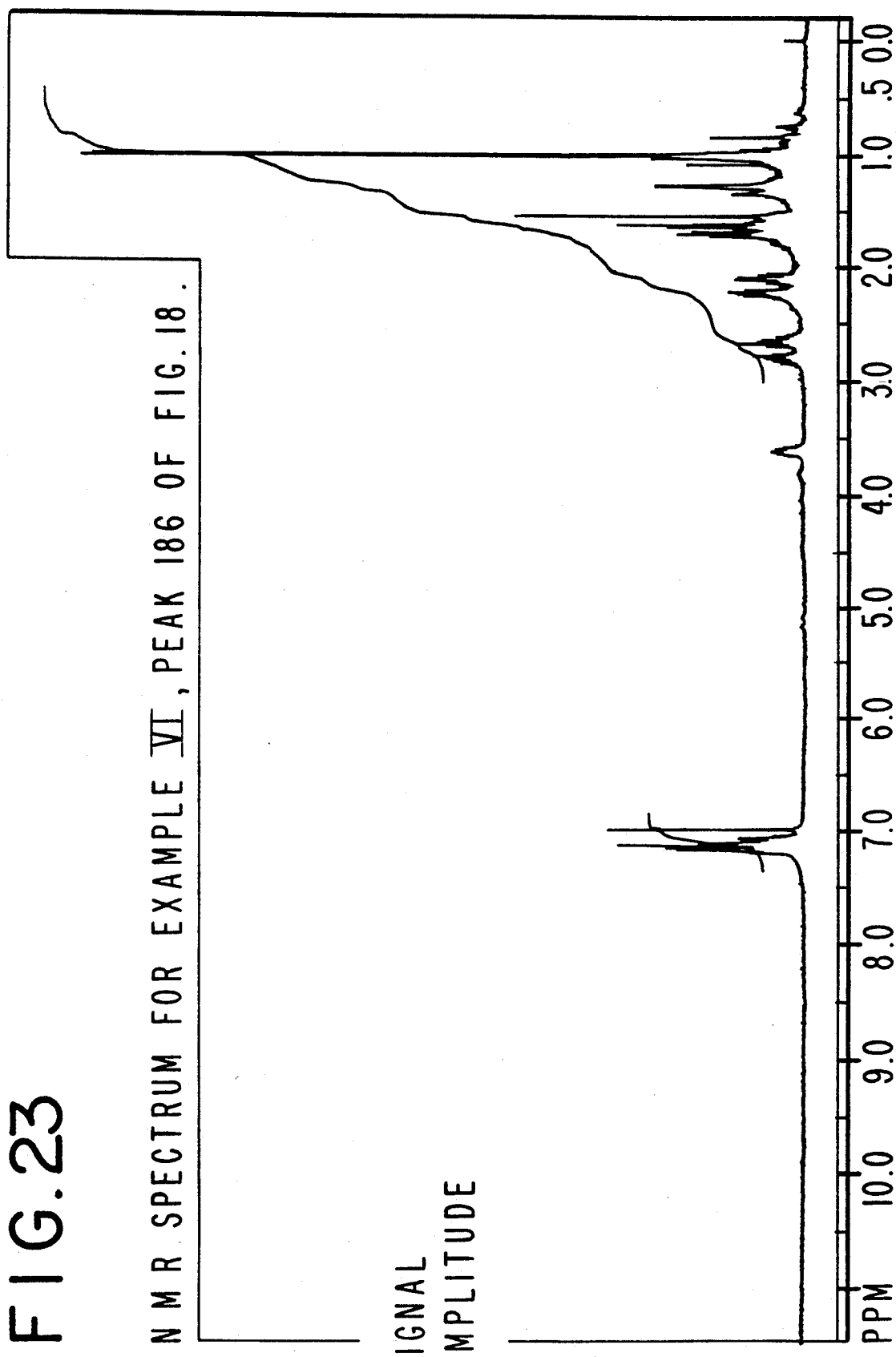

FIG. 23 is the NMR spectrum for the peak indicated by reference numeral 186 of the GC profile of FIG. 18 for the compound having the structure:

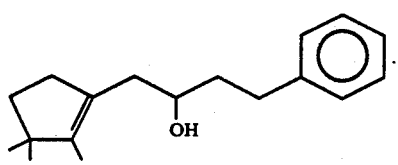

Figure 24:
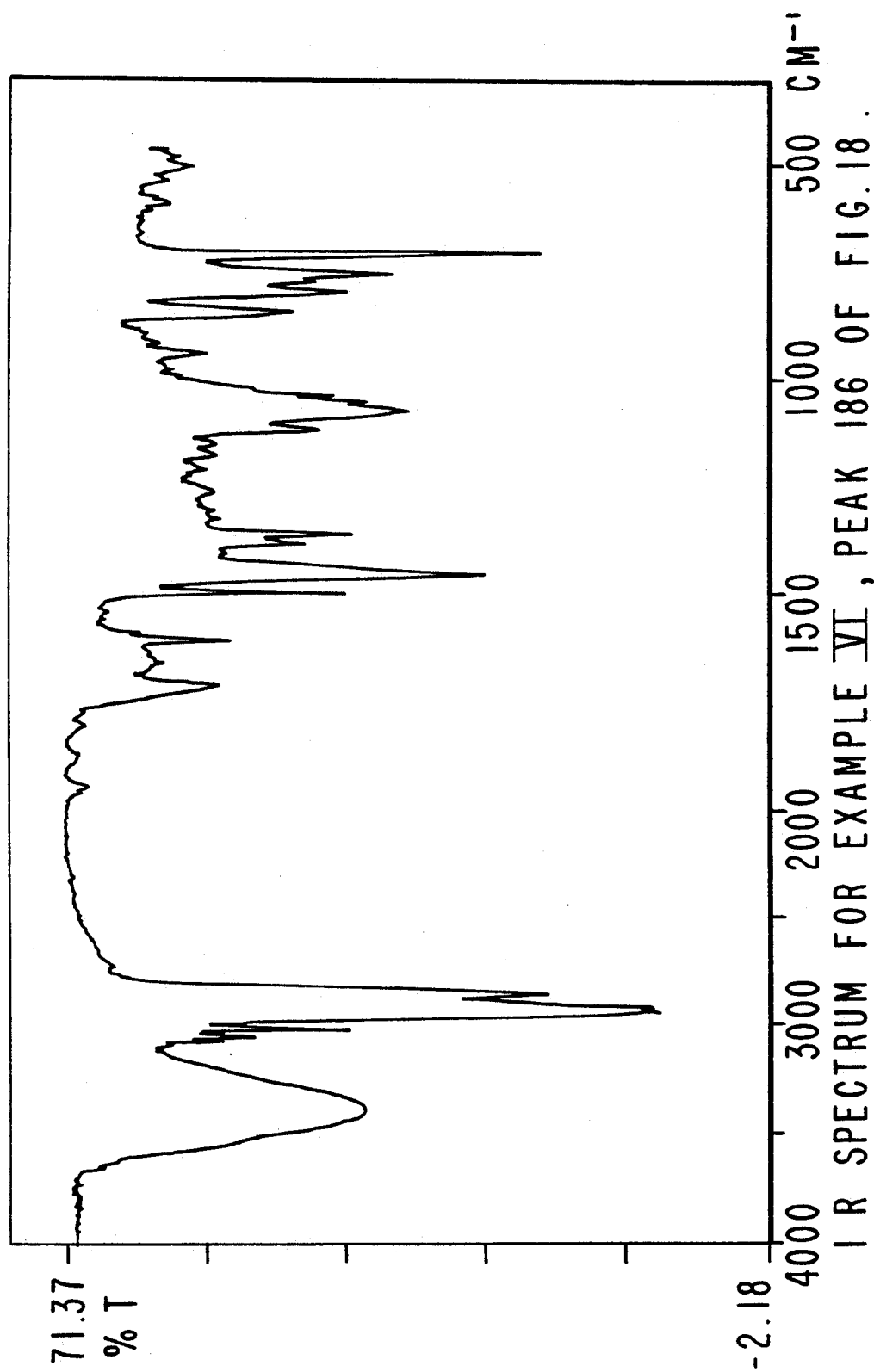

FIG. 24 is the infra-red spectrum for the peak indicated by reference numeral 186 of the GC spectrum of FIG. 18 for the compound having the structure:

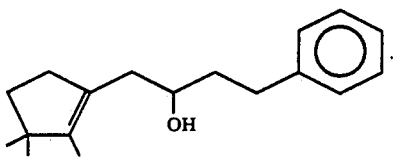

Figure 25:
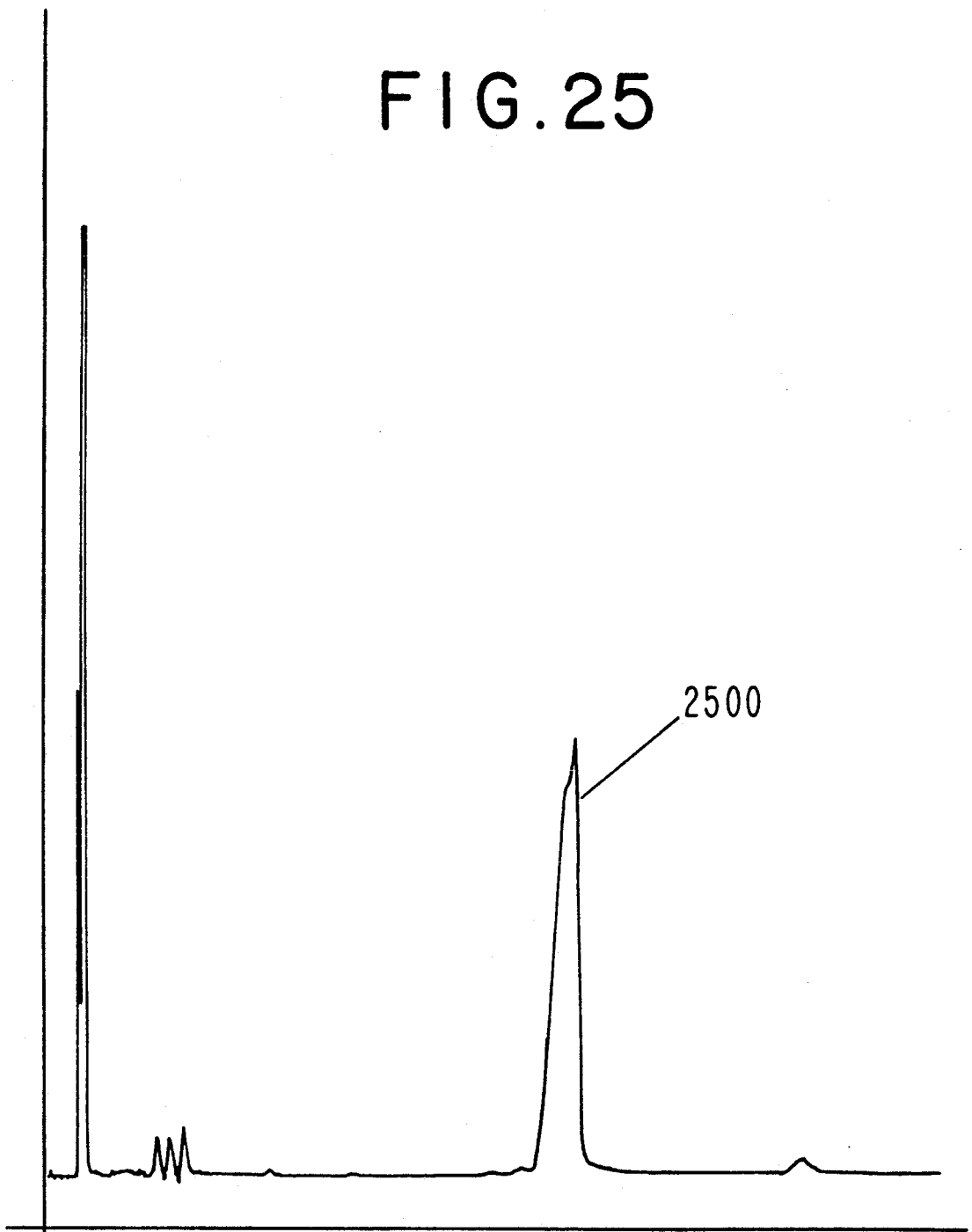

FIG. 25 is the GC spectrum for the reaction product of Example VII containing the compound having the structure:

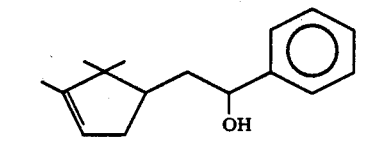

(Conditions: SE-30 column programmed at 150°–220° C. at 8° C. per minute).

Figure 26:
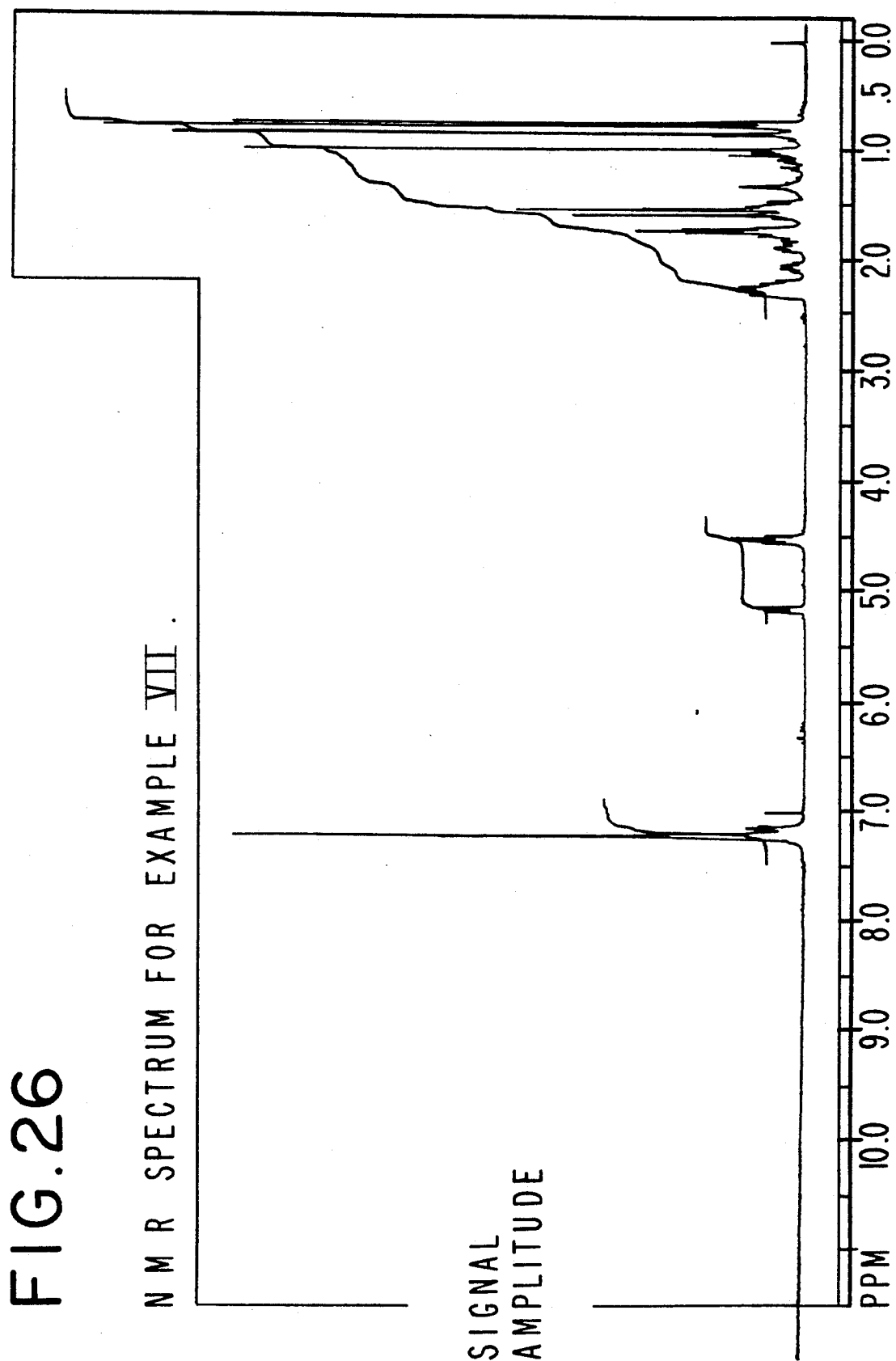

FIG. 26 is the NMR spectrum for the compound having the structure:

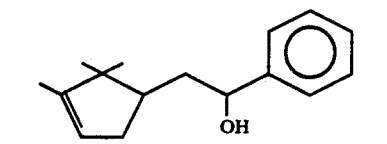

produced according to Example VII.

Figure 27:
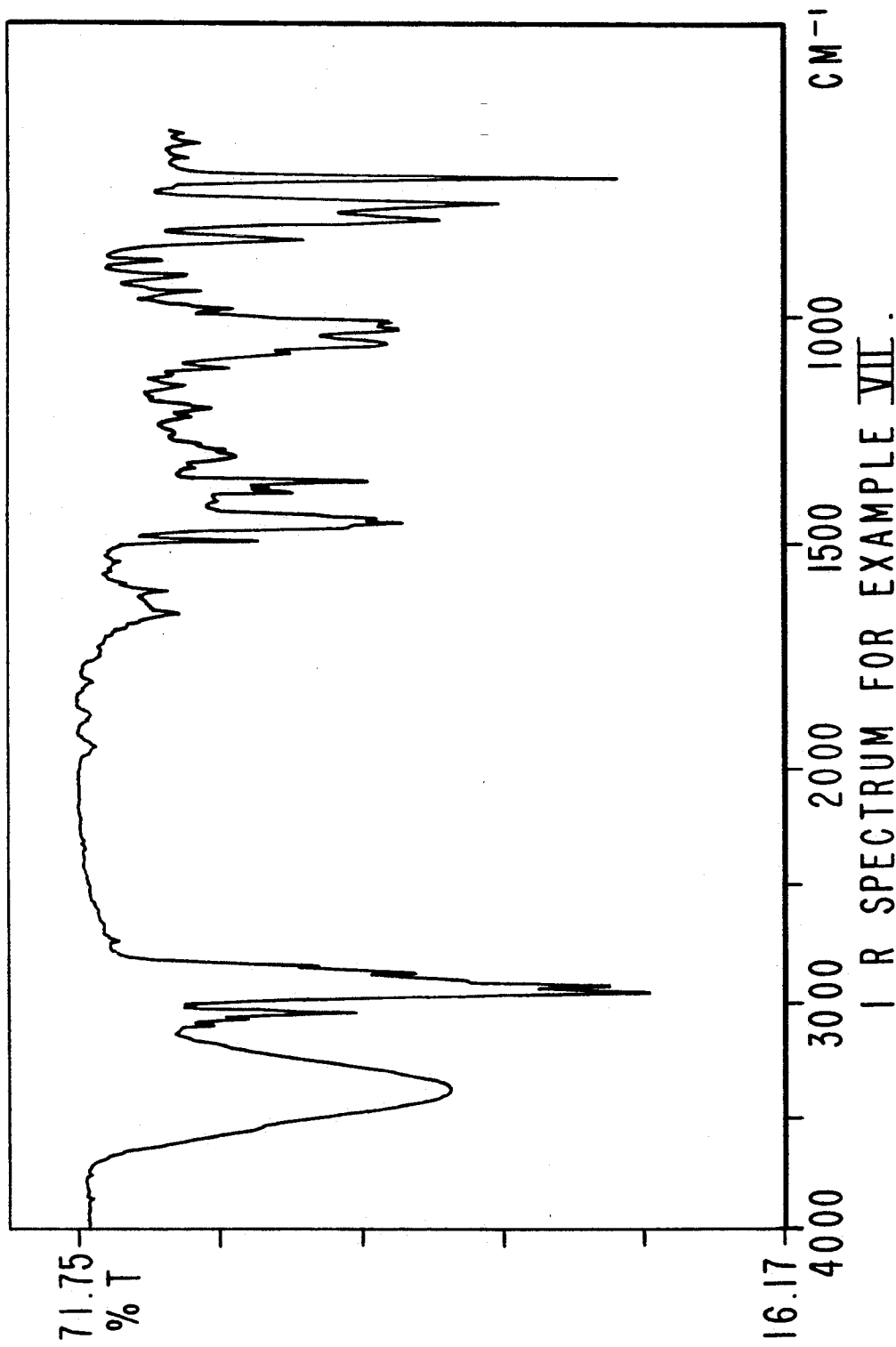

FIG. 27 is the infra-red spectrum for the compound having the structure:

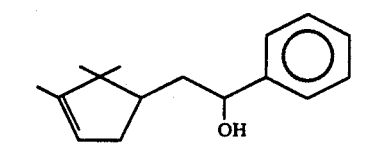

prepared according to Example VII.

Figure 28:
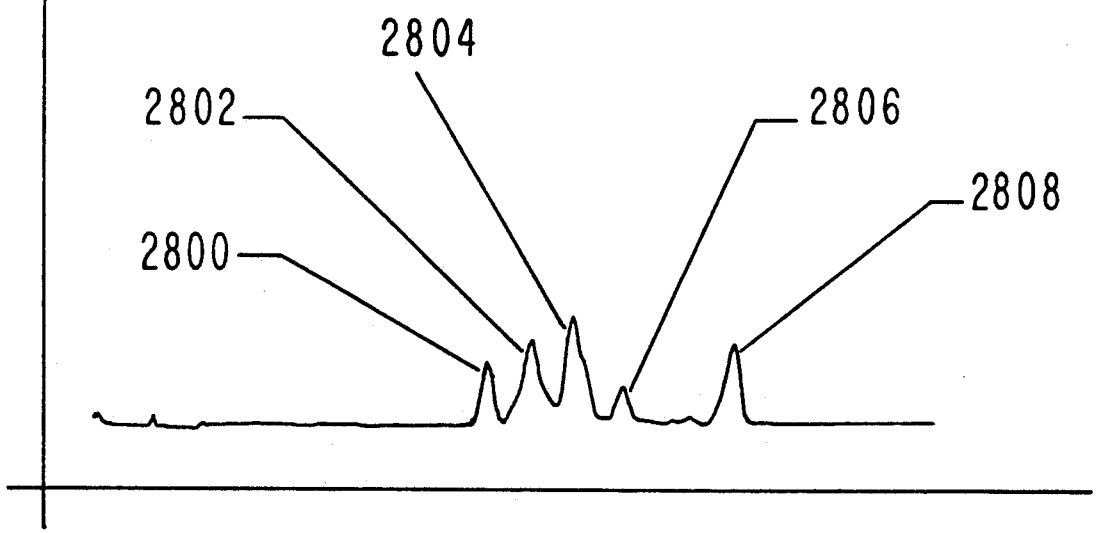

FIG. 28 is the GC spectrum for the reaction product of Example VIII containing the compounds having the structures:

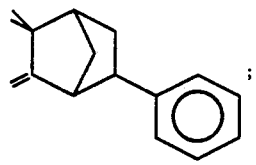

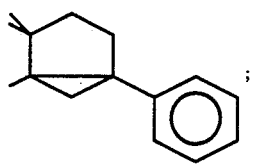

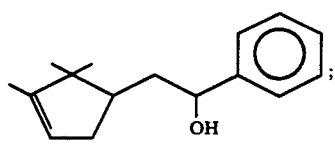

and

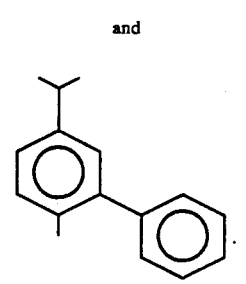

Figure 29:
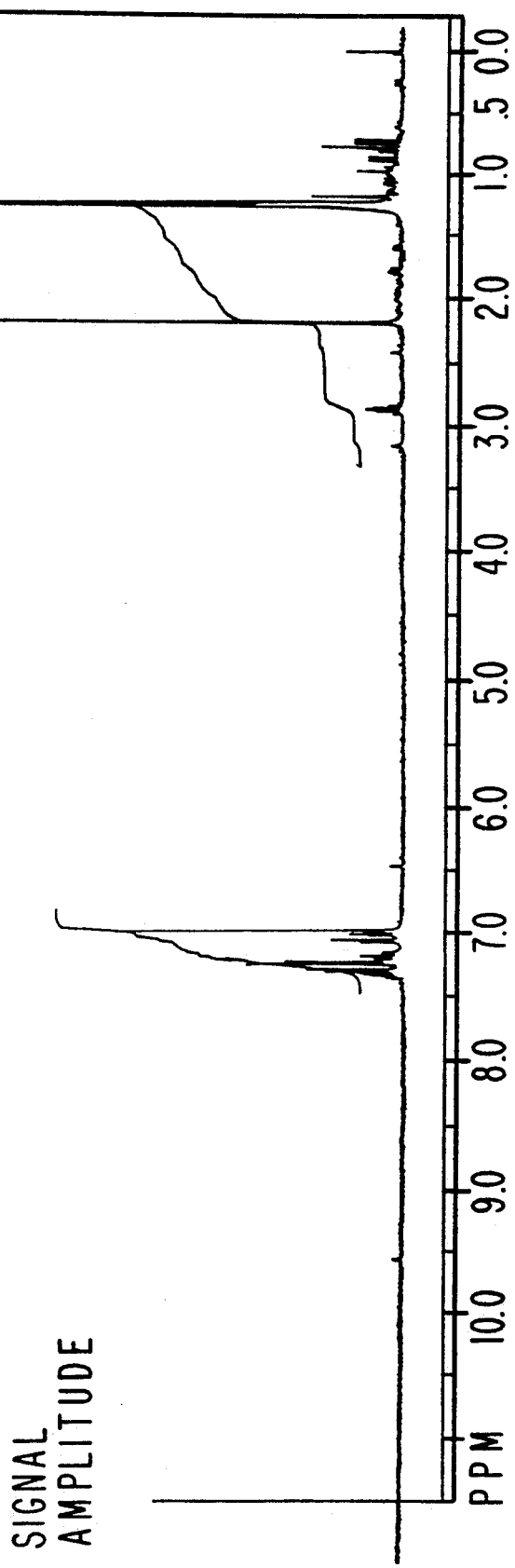

FIG. 29 is the NMR spectrum for the peak indicated by reference numeral 2806 of the GC spectrum of FIG. 28 for the compound having the structure:

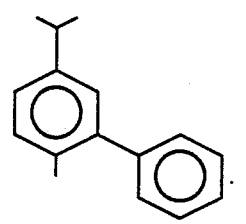

Figure 30:
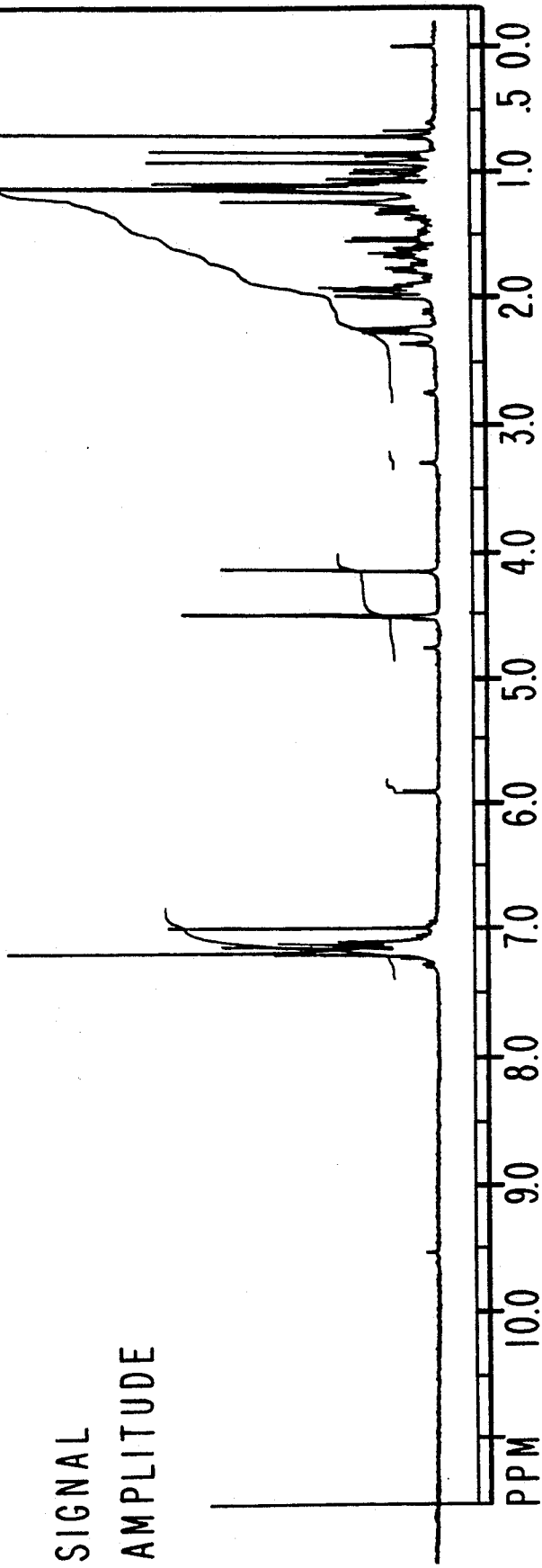

FIG. 30 is the NMR spectrum for the peak indicated by reference numeral 2802 of the GC spectrum of FIG. 28 for the compound having the structure:

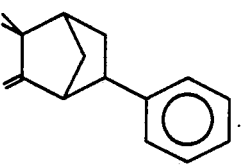

Figure 31:
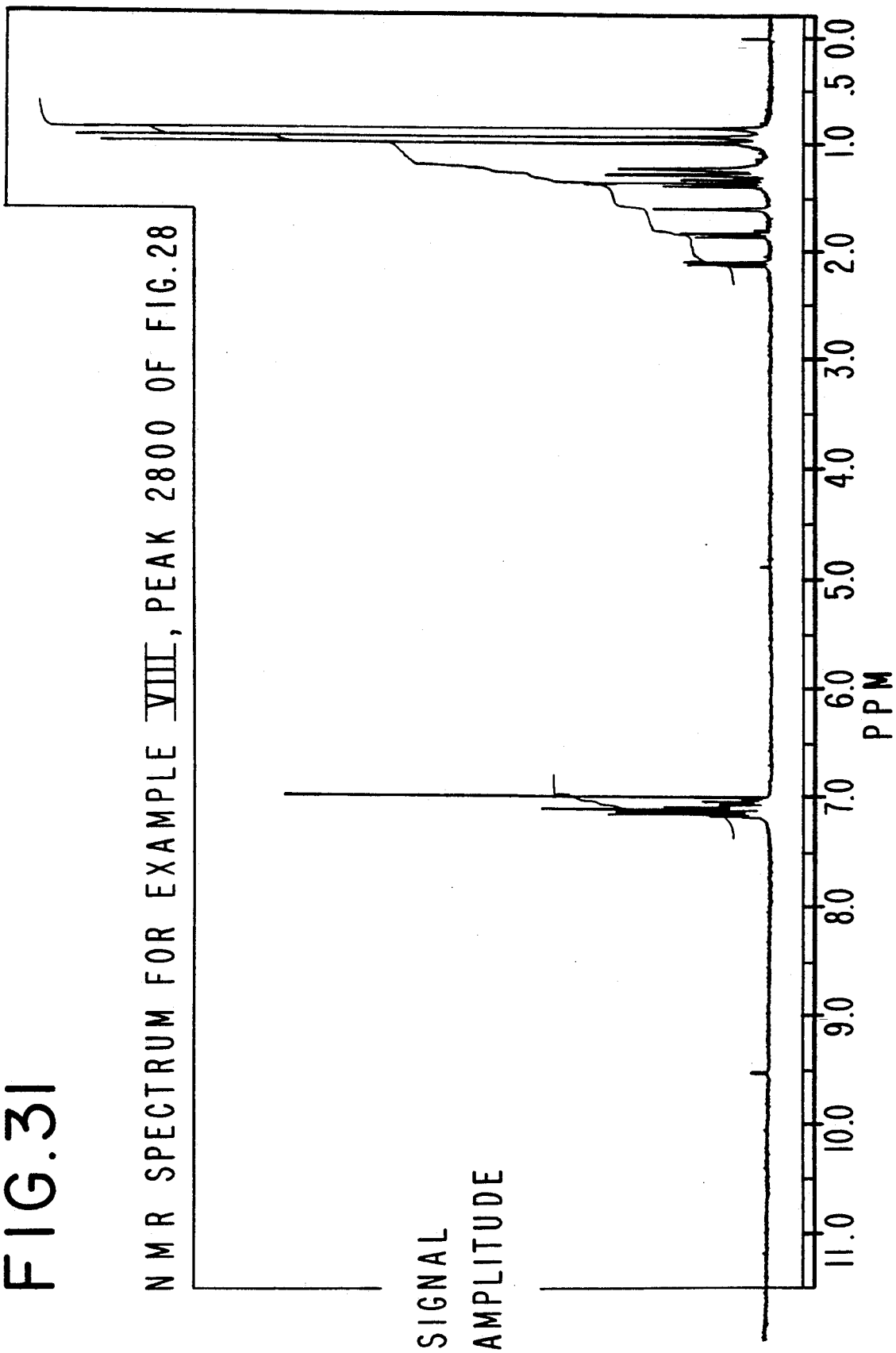

FIG. 31 is the NMR spectrum for the peak indicated by reference numeral 2800 of the GC spectrum of FIG. 28 for the compound having the structure:

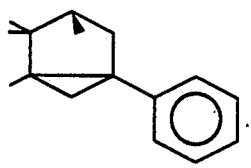

Figure 32:
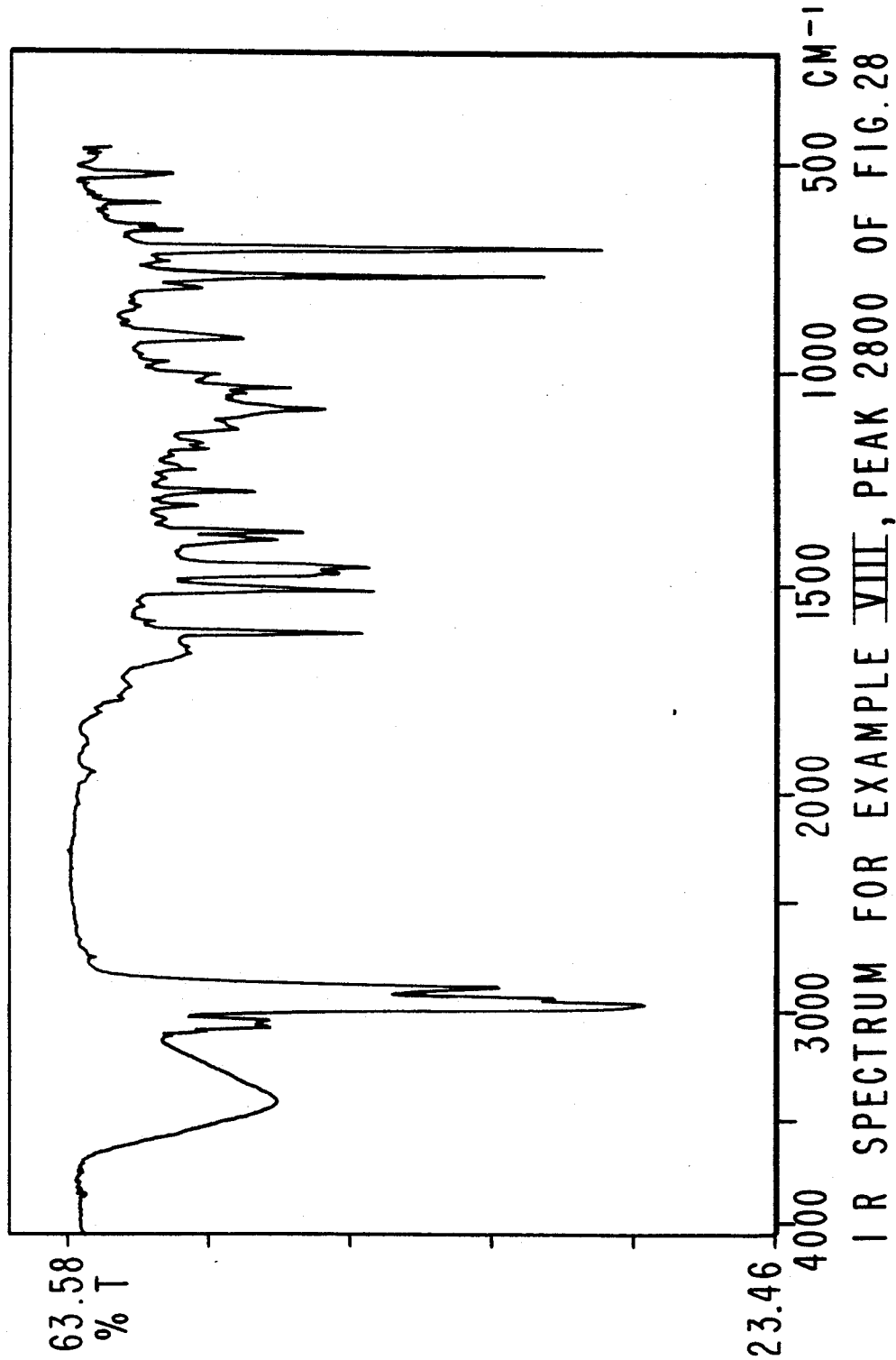

FIG. 32 is the infra-red spectrum for the peak indicated by reference numeral 2800 of the GC spectrum of FIG. 28 for the compound having the structure:

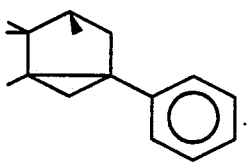

Figure 33:
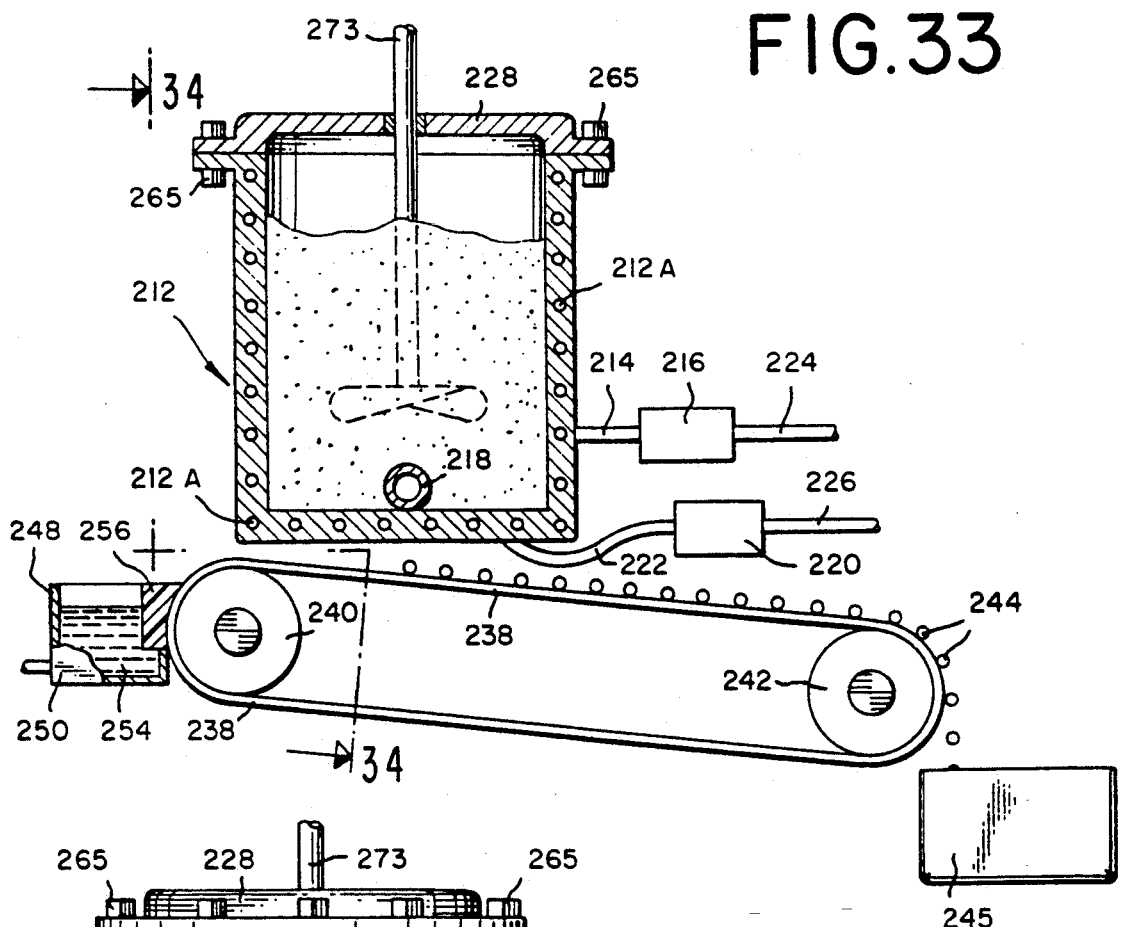

FIG. 33 is a partial side elevation and partial sectional view of an apparatus for forming polymer pellets scented with one of the perfume compositions or perfumery materials of our invention containing at least one of the aryl oxabicyclooctane derivatives ,and phenyl norbornane derivatives of our invention.

Figure 34:
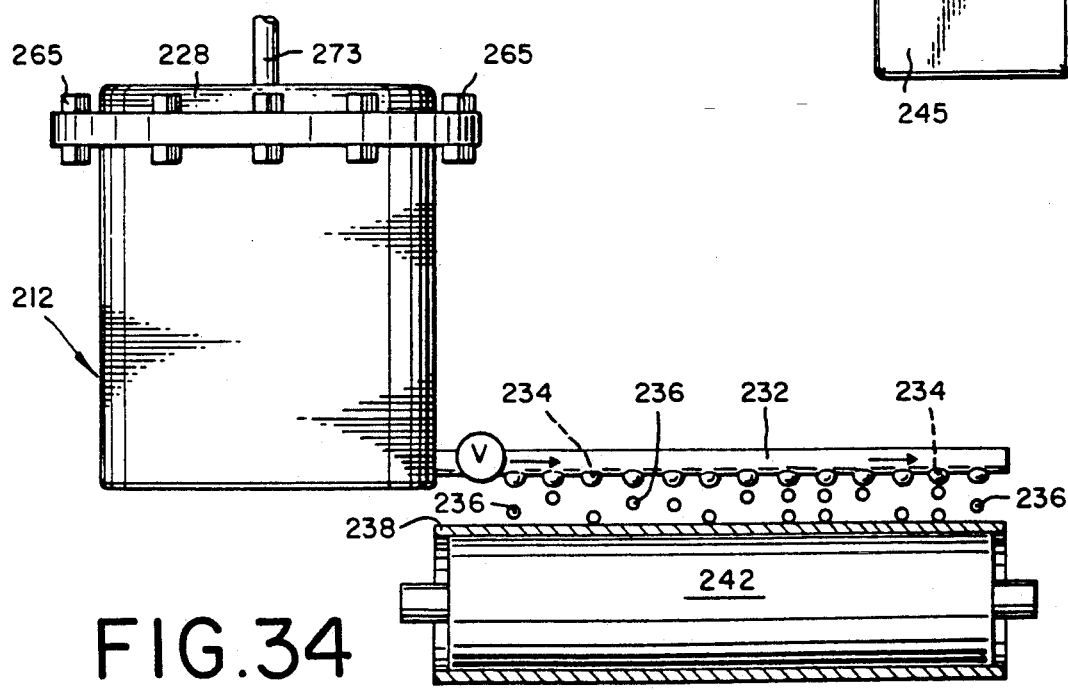

FIG. 34 is a section taken on line 34—34 of FIG. 33.

DETAILED DESCRIPTION OF THE DRAWINGS

Figure 1:
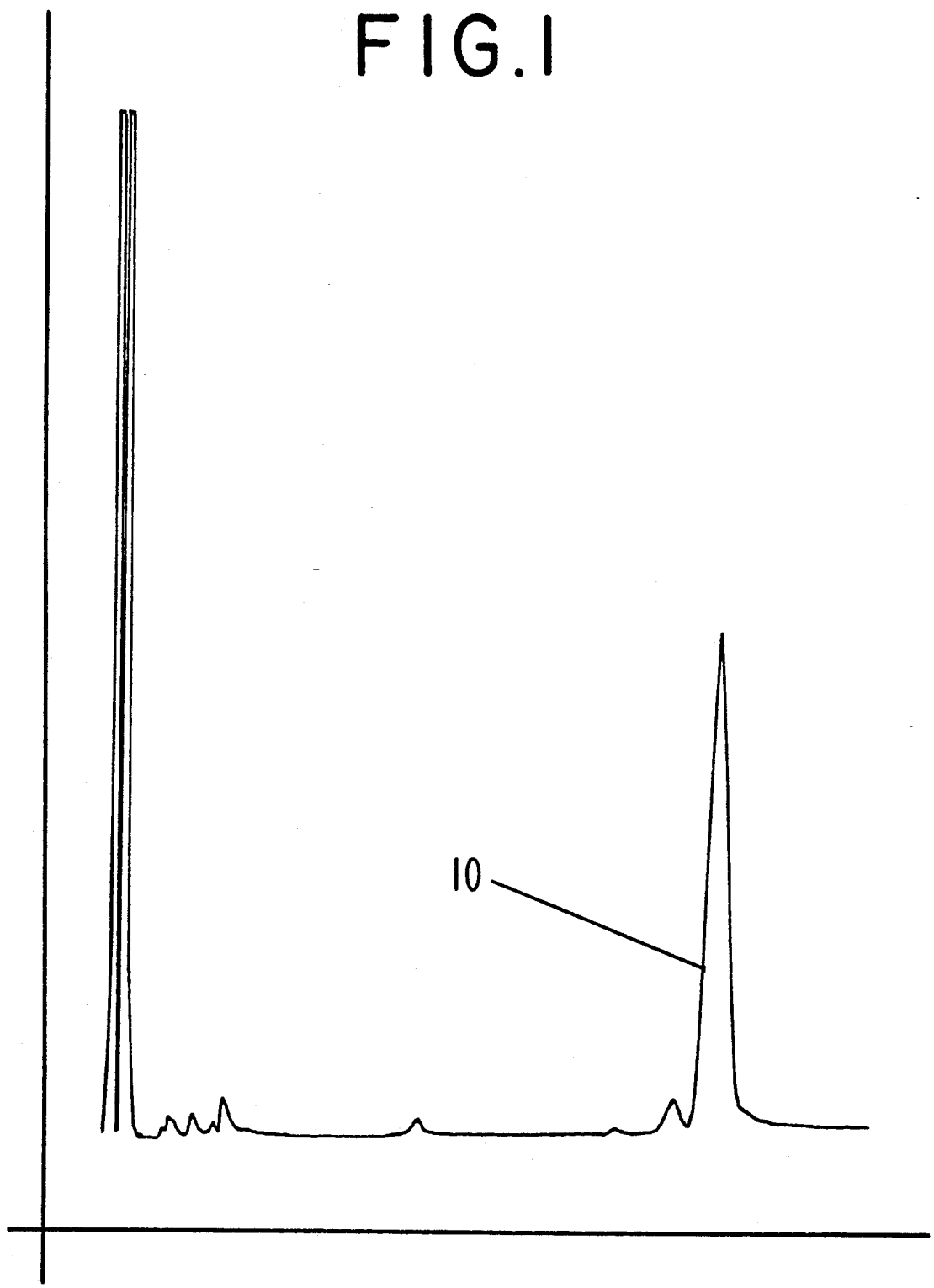
FIG. 1 is the GC profile for the reaction product of Example I containing the compound having the structure.

FIG. 1 is the GC profile for the reaction product of Example I containing the compound having the structure:

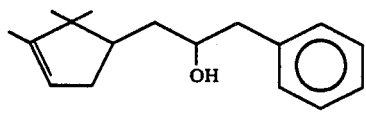

(Conditions: SE-30 column programmed at 150°–220° C. at 8° C. per minute). The peak indicated by reference numeral 10 is the peak for the compound having the structure:

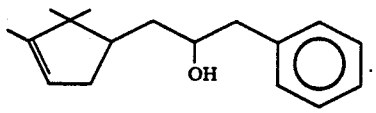

FIG. 4 is the GC profile for the reaction product of Example II containing the compounds having the structures:

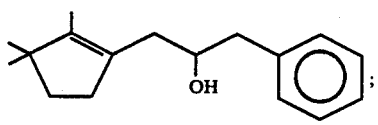

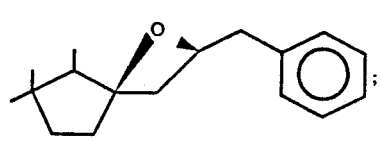

and

The peaks indicated by reference numerals 40A and 40B are for the compounds having the structures:

and

separately.

FIG. 9 is the GC profile for the reaction product of Example III containing the compound having the structure:

The peak indicated by reference numeral 90 is the peak for the by-product having the structure:

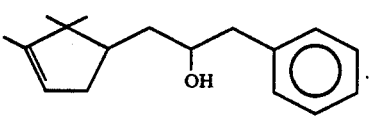

The peak indicated by reference numeral 92 is for the compound having the structure:

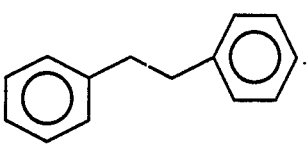

FIG. 12 is the GC profile for the reaction product of Example IV containing the compounds having the structures:

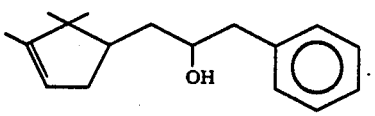

and

-continued

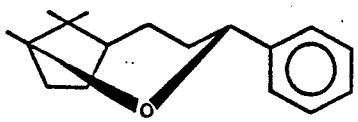

(Conditions: SE-30 column programmed at 150°-220° C. at 8° C. per minute.) The peaks indicated by reference numerals 120 and 122 are for the compounds having the structures:

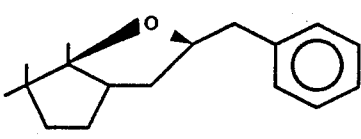

and

separately.

FIG. 15 is the GC spectrum for the reaction product of Example V containing the compounds having the structures:

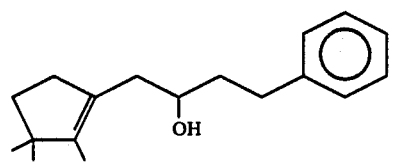

and

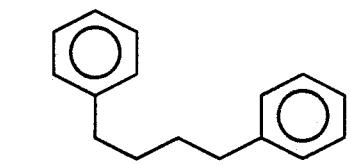

(Conditions: SE-30 column programmed at 180° C. isothermal). The peak indicated by reference numeral 150 is the peak for the compound having the structure:

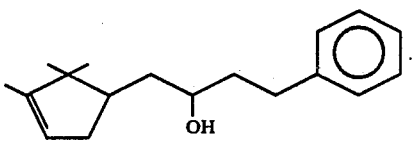

The peak indicated by reference numeral 152 is the peak for the compound having the structure:

FIG. 18 is the GC spectrum for the reaction product of Example VI containing the compounds having the structures:

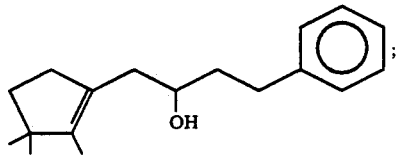

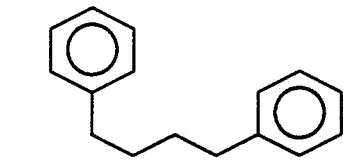

and

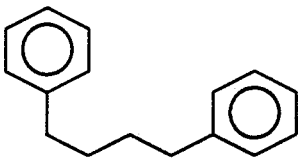

The peak indicated by reference numeral 180 is the peak for the compound having the structure:

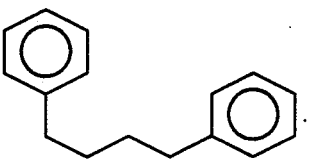

The peaks indicated by reference numerals 182 and 183 are the peaks for the compounds having the structures:

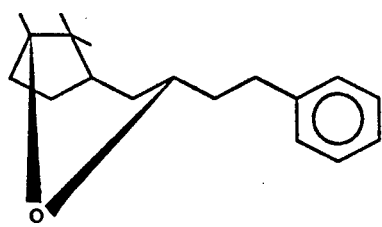

and

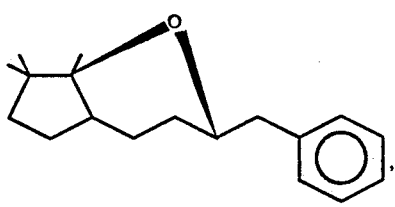

separately.

The peak indicated by reference numeral 186 is the peak for the compound having the structure:

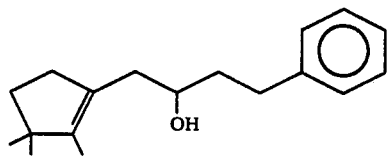

(Conditions: SE-30 column programmed at 180° C. isothermal).

FIG. 25 is the GC spectrum for the reaction product of Example VIII containing the compound having the structure:

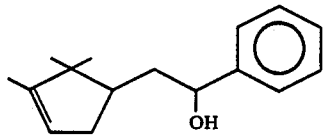

(Conditions: SE-30 column programmed at 150°-220° C. at 8° C. per minute). The peak indicated by reference numeral 2500 is the peak for the compound having the structure:

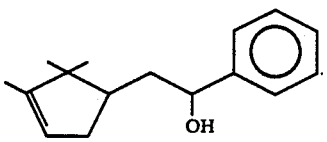

FIG. 28 is the GC spectrum for the reaction product of Example VIII containing the compounds having the structures:

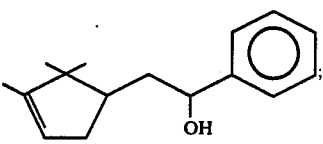

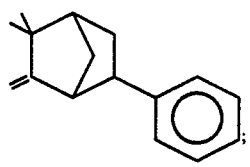;

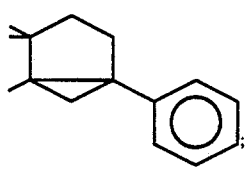;

and

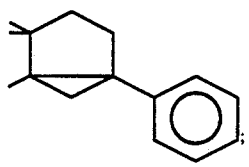

The peak indicated by reference numeral 2800 is the peak for the compound having the structure:

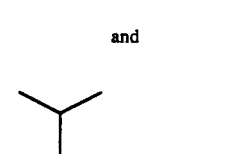

The peak indicated by reference numeral 2802 is the peak for the compound having the structure:

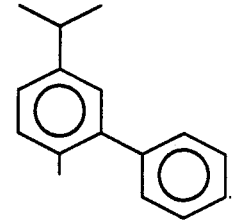

The peak indicated by reference numeral 2806 is the peak for the compound having the structure:

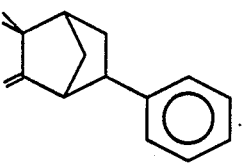

The peak indicated by reference numeral 2808 is the peak for the compound having the structure:

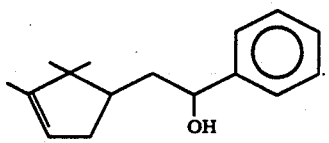

The peak indicated by reference numeral 2804 is for an isomer of the compound having the structure:

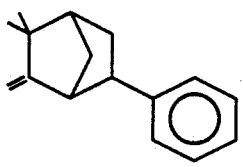

(Conditions: SE-30 column programmed at 150°-220° C. at 8° C. per minute).

Referring to FIGS. 33 and 34, the apparatus used in producing polymeric fragrances containing at least one of the aryl oxabicyclooctane derivatives and phenyl norbornane derivatives of our invention comprises a device for forming scented polyolefin (for example) pellets which comprises a vat or container 212 into which a mixture of polyolefins such as polyethylene or an aromatic substance or scented material containing or consisting of at least one of the aryl oxabicyclooctane derivatives and phenyl norbornane derivatives of our invention is placed. The container is closed by an airtight lid 228 and clamped to the container by bolts 265. A stirrer 273 traverses the lid or cover 228 in air tight manner and is rotated in a suitable manner. A surrounding cylinder 212 having heating coils which are supplied with electric current through cable 224 from a rheostat or control 216 is operated to maintain the temperature inside the container 212 such that polyethylene or other thermoplastic polymer in the container will be maintained in the molten or liquid state. It has been found advantageous to employ a colorless, odorless polymer (e.g., polyethylene) with a viscosity ranging between 180 and 220 Saybolt seconds and having a melting point in the range of 220°-280° F. The heater 212A is operated to maintain the upper portion of the container 212 within a temperature range of from 250°-350° F. The bottom portion of the container 212 is heated by means of heating coils 212A heated through a control 220 connected thereto through a connecting wire 226 to maintain the lower portion of the container 212 within a temperature range of from 250°-350° F.

Thus, polymer (e.g., polyolefin) added to the container 212 is heated from 10-12 hours whereafter a scent or aroma imparting material which contains or consists of at least one of the aryl oxabicyclooctane derivatives and phenyl norbornane derivatives of our invention is quickly added to the melt. The material must be compatible with the polyolefin and forms a homogeneous liquid melt therewith. The scented material containing or consisting of at least one of the aryl oxabicyclooctane derivatives and phenyl norbornane derivatives of our invention is of a type for the particular aroma desired and formulated specifically for the scenting purpose for which the polyolefin will be employed. The heat resisting coils and aromatic materials in some instances in solid or powdered form, may be employed or added to the polyolefin in the container 212. Generally about 10-30% by weight of the scenting material is added to the polyolefin.

After the scent imparting material containing or consisting of at least one of the aryl oxabicyclooctane derivatives and phenyl norbornane derivatives of our invention is added to the container 212, the mixture is stirred for a few minutes, for example, 5-15 minutes and maintained within the temperature ranges indicated previously by the heating coils 212A and 218, respectively. The controls 216 and 220 are connected through cables 224 and 226 to a suitable supply of electric current for supplying the power for heating purposes. The controls 216 and 220 are connected to the heating coils 212A respectively, through wires 214 and 222.

Thereafter, the valve "V" is opened permitting the mass to flow outwardly through conduit 232 having a multiplicity of orifices 234 adjacent to the lower side thereof. The outer end of the conduit 232 is closed so that the liquid polymer (e.g., polyolefin) an aroma imparting mixture (containing at least one of the aryl oxabicyclooctane derivatives and phenyl norbornane derivatives of our invention) will continuously drop through the orifices 234 downwardly from the conduit 232. During this time, the temperature of the polymer (e.g., polyolefin) and aroma mixture containing at least one of the aryl oxabicyclooctane derivatives and phenyl norbornane derivatives of our invention in the container 212 is accurately controlled so that a temperature in the range of from about 210°-275° F. will exist in the conduit 232. The regulation of the temperature through the control 216 and the control 220 is essential in order to insure temperature balance to provide for the continuous dropping or dripping of molten polymer (e.g., polyolefin) and scenting material containing or consisting of at least one of the aryl oxabicyclooctane derivatives and phenyl norbornane derivatives of our invention through the orifices 234 at a rate which will insure the formation of droplets 236 which will fall downwardly onto a moving conveyor belt 238 trained to run between conveyor wheels 240 and 242 beneath the conduit 232.

When the droplets 236 fall onto the conveyor 238, they form pellets 244 which harden almost instantaneously and fall off the end of the conveyor 238 into a container 245 which is advantageously filled with water or some other suitable cooling liquid in order to insure the rapid cooling of each of the pellets. The pellets 244 are then collected from the container 245 and utilized in a process as illustrated, infra.

A feature of this aspect of the process of our invention is in the provision for moistening the conveyor belt 238 to insure rapid formation of the solid polymer (e.g., polyolefin) scented pellets 244 without sticking to the belt. The belt 238 is advantageously of a material which will not normally stick to a melted plastic but the moistening means 248 insures a sufficiently cold temperature of the belt surface for the adequate formation of the pellets 244. The moistening means comprises a container 250 which is continuously fed with water 254 to maintain a level for moistening a sponge element 256 which bears against the exterior surface of the belt 238.

THE INVENTION

The instant invention provides aryl oxabicyclooctane derivatives and phenyl norbornane derivatives defined according to the generic structure:

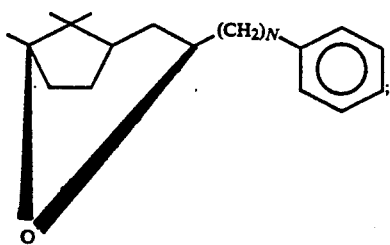

the generic structure:

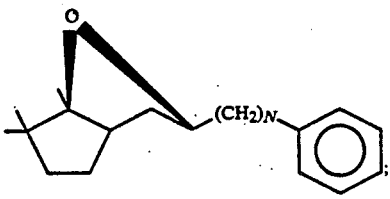

and the structures:

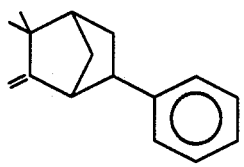

and

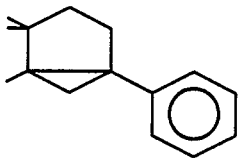

wherein N represents 1 or 2. The instant invention also defines the materials defined according to the generic structure:

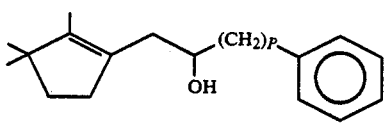

wherein P represents 1 or 2. The instant invention also defines the intermediates having the structures:

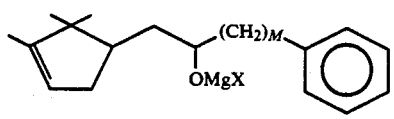

and

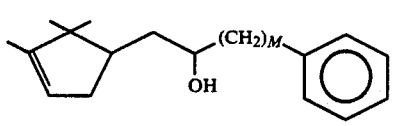

wherein M is 0, 1 or 2 and X represents chloro or bromo. The aryl oxabicyclooctane derivatives and phenyl norbornane derivatives of our invention and the compound defined according to the structure:

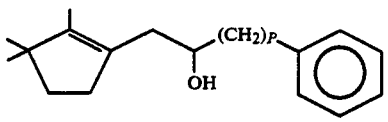

impart, augment and/or enhance sweaty, animalic, amber, musky, dry camphoraceous, woody-peppery aromas, with green, herbaceous, sweaty, animalic, cigar box-like and woody topnotes in or to perfume compositions, colognes and perfumed articles (e.g., solid or liquid, anionic, cationic, nonionic or zwitterionic detergents, perfumed polymers, fabric softener compositions, fabric softener articles, hair preparations, cosmetic powders and the like).

Briefly, the aryl oxabicyclooctane derivatives and phenyl norbornane derivatives of our invention and the compounds defined according to the generic structure:

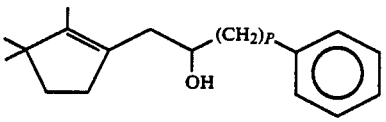

of our invention may be prepared by first reacting the compound having the structure:

with a phenyl or aralkyl magnesium halide defined according to the structure:

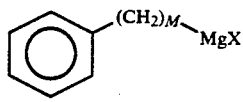

wherein M represents 0, 1 or 2 and X represents chloro or bromo thereby forming the intermediate having the structure:

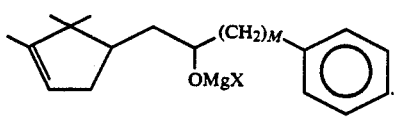

The intermediate having the structure:

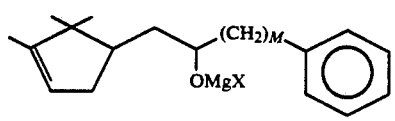

is then hydrolyzed (e.g., in weak acid) in order to form one of the compounds defined according to the generic structure:

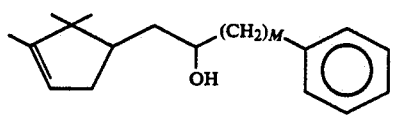

wherein M is 0, 1 or 2. The foregoing reaction sequence is illustrated, thusly:

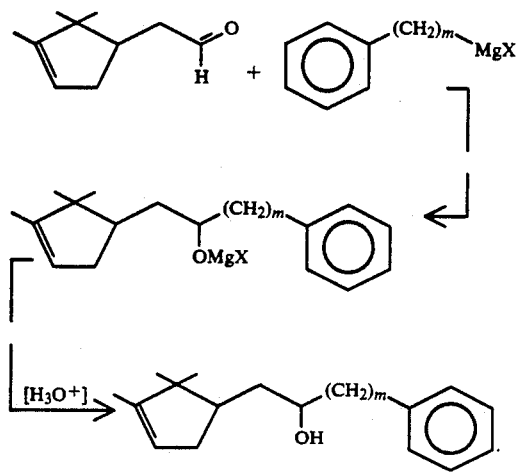

The resulting products defined according to the generic structure:

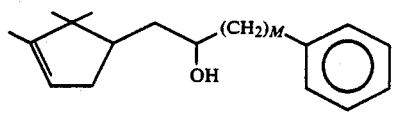

are then further reacted using a cyclization reagent, e.g., borontrifluoride etherate or paramethane sulfonic acid according to the reaction:

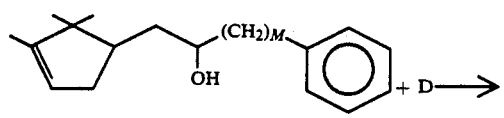

[$G_1$ OR $G_2$]

wherein M represents 0, 1 or 2; D represents a cyclizing reagent such as paramethane sulfonic acid or borontrifluoride etherate and $G_1$ and $G_2$ represent products created as a result of the cyclization reaction. Thus, when M is 0, the reaction product is a mixture of compounds defined according to the structures:

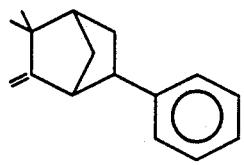

and

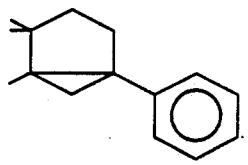

When M is 1 or 2, the reaction products are defined according to the structures:

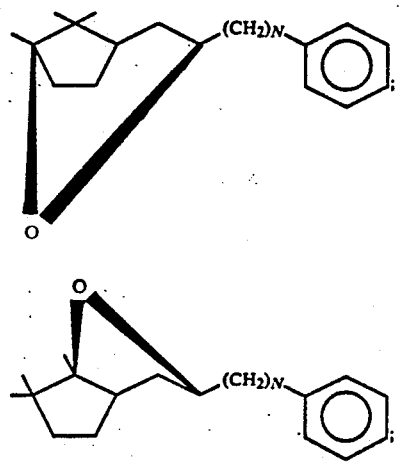

and

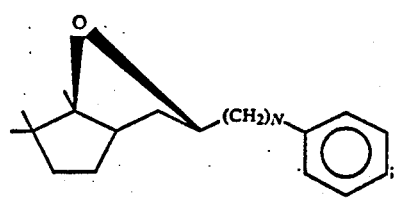

wherein N and P are the same and N is 1 or 2 and P is 1 or 2. The compounds having the structures:

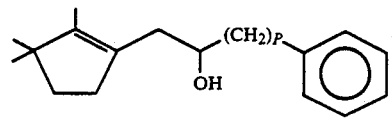

and

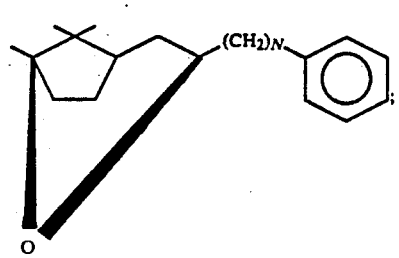

are separated by means of fractional distillation from the compounds having the structure:

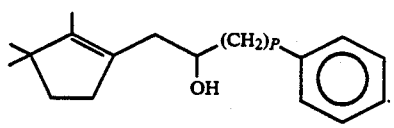

The compounds having the structures:

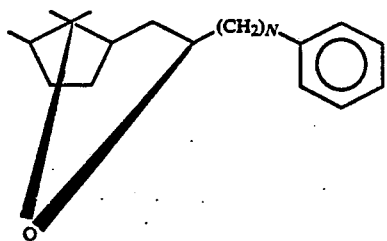

and

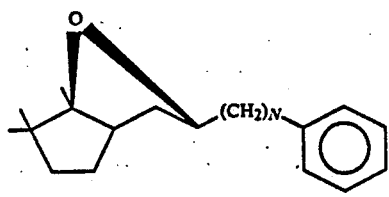

as well as the compounds having the structure:

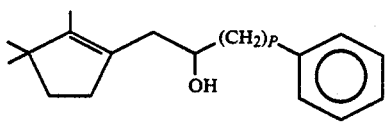

have useful perfumery properties as exemplified, infra.

The Grignard reaction is carried out in a solvent, e.g., tetrahydrofuran at a temperature of from about −5° C. up to about +5° C. The resulting organometallic compounds defined according to the structure:

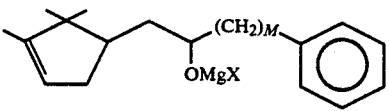

are then hydrolyzed in weak acid such as dilute hydrochloric acid.

The subsequent cyclization reaction is carried out using a cyclization reagent, preferably methane sulfonic acid and nitromethane. In the alternative, boron trifluroide diethyl etherate can be used as a cyclization reagent (together with nitromethane). In place of nitromethane, nitroethane can be used as the cyclization reagent. The cyclization reaction takes place at a temperature in the range of from about 60° C. up to about 90° C. for a period of time of from about three hours up to about ten hours.

The resulting products are then separated by means of fractional distillation as exemplified, infra, and as discussed, supra.

Surprisingly, with regard to the cyclization of the compounds defined according to the generic structure:

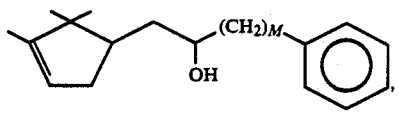

when M is 1 or 2, the cyclic ethers defined according to the generic structure:

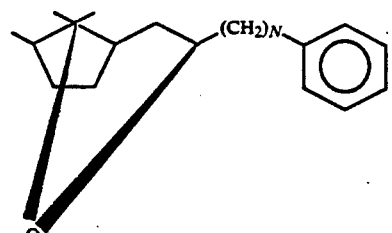

and

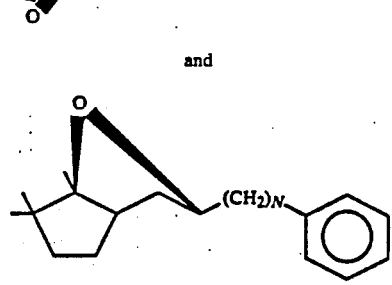

are formed together with the compounds defined according to the structure:

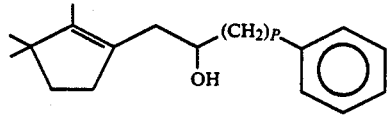

On the other hand, when M is 0, the compounds having the structures:

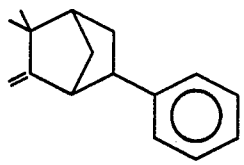

and

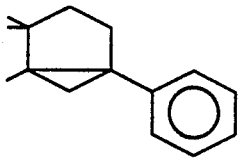

are formed. In view of the surprising reactions, the compounds defined according to the structures:

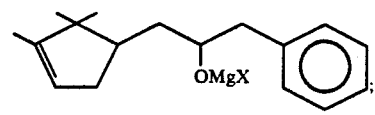

-continued

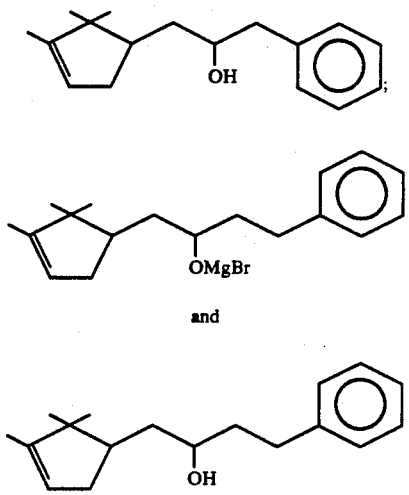

and have surprising and unexpected properties as chemical intermediates.

This genus of chemical intermediates may be defined, thusly:

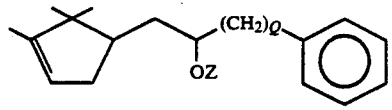

wherein Z represents H or MgX (with X being defined as chloro or bromo and Q being one of the integers 1 or 2.

The following Table I sets forth the specific products produced according to our invention which have organoleptic utilities and their perfumery properties.

TABLE I

| Product Identification | Perfumery Property |
| --- | --- |
| Mixture of compounds having the structures: | A sweaty, animalic, dry-camphoraceous, woody, peppery aroma, with green, herbaceous, sweaty, animalic and woody topnotes. |
| and | |
| prepared according to Example II. | |
| Mixtures of compounds having the structures: | An intense, woody, amber and musky aroma, with cigar box-like topnotes. |
| and | |
| prepared according to Example VIII. | |
| Mixture of compounds having the structures: | A sweaty, animalic, musky and amber aroma, with cigar box-like and green topnotes. |

TABLE I-continued

| Product Identification | Perfumery Property |
|---|---|
| 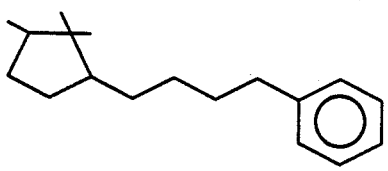 | |
| o and 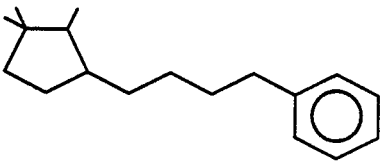 prepared according to Example VI. Compound having the structure: 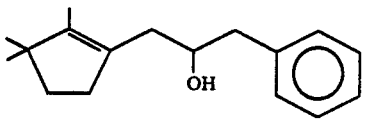 prepared according to Example III. Compound having the structure: 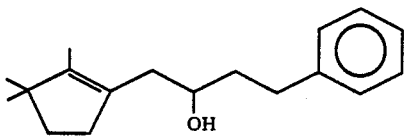 prepared according to Example VI. | An intense, civet/musky aroma, with green topnotes. An intense amber aroma, with green topnotes. |

At least one of the aryl oxabicyclooctane derivatives and phenyl norbornane derivatives of our invention or one of the compounds defined according to the structure:

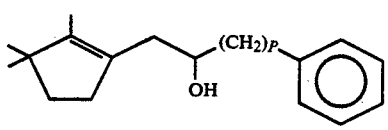

wherein P is 1 or 2 and one or more auxiliary perfume ingredients including, for example, alcohols (other than the alcohols of our invention), aldehydes, ketones, terpenic hydrocarbons, esters, lactones, ethers (other than the ethers of our invention), natural essential oils and synthetic essential oils may be admixed so that the combined odors of the individual components produce a pleasant and desired fragrance, particularly and preferably in the pine fragrance area. Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low boiling, fresh smelling materials.

In perfume compositions, it is the individual components which contribute to their particular olfactory characteristics, however, the over-all sensory effect of the perfume composition will be at least the sum total of the effects of each of the ingredients. Thus, at least one of the aryl oxabicyclooctane derivatives and phenyl norbornane derivatives of our invention or at least one of the compounds defined according to the structure:

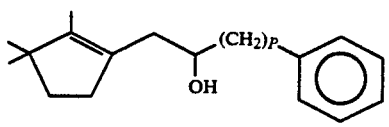

wherein P is 1 or 2 of our invention can be used to alter, modify or enhance the aroma characteristics of a perfume composition, for example, by utilizing or moderating the olfactory reaction contributed by another ingredient in the composition.

The amount of one or more of the aryl oxabicyclooctane derivatives and phenyl norbornane derivatives of our invention or one or more of the compounds defined according to the structure:

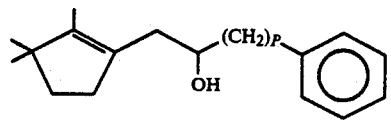

wherein P is 1 or 2 of our invention which will be effective in the perfume compositions as well as in the perfumed articles and colognes depends on many factors including the other ingredients, their amounts and the effects which are desired. It has been found that perfume compositions containing as little as 0.01% of at least one of the aryl oxabicyclooctane derivatives and phenyl norbornane derivatives of our invention or of at least one of the compounds having the structure:

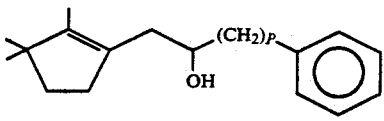

of our invention or even less (e.g., 0.005%) can be used to impart, augment or enhance sweaty, animalic, amber, musky, dry-camphoraceous, woody-peppery aromas, with green, herbaceous, sweaty, animalic, cigar box-like and woody topnotes in and to soaps, cosmetics, solid or liquid, anionic, cationic, nonionic or zwitterionic detergents, fabric softener compositions, fabric softener articles, hair preparations and perfumed polymers. The amount employed can range up to 70% of the fragrance components and will depend on considerations of cost, nature of the end product, the effect desired on the finished product and the particular fragrance sought.

One or more of the aryl oxabicyclooctane derivatives and phenyl norbornane derivatives of our invention and/or one or more of the compounds having the structure:

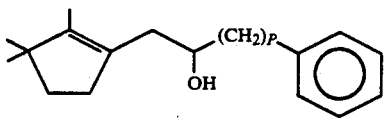

of our invention are useful (taken alone or together with other ingredients in the perfume compositions) as (an) olfactory component(s) in detergents and soaps, space odorants and deodorants, perfumes, colognes, toilet water, bath preparations such as creams, deodorants, hand lotions and sun screens; powders such as talcs, dusting powders, face powders and the like. When used as (an) olfactory component(s) as little as 1% of at least one of the aryl oxabicyclooctane derivatives and phenyl norbornane derivatives of our invention taken alone or further together with one of the compounds having the structure:

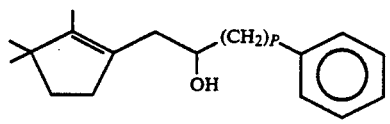

of our invention or even less will suffice to impart intense and substantive sweaty, animalic, amber, musky, dry-camphoraceous, and woody-peppery aromas, with green, herbaceous, sweaty, animalic, cigar box-like and woody topnotes to pine formulations. Generally, no more than 20% of at least one of the aryl oxabicyclooctane derivatives and phenyl norbornane derivatives of our invention taken alone or further together with one of the compounds having the structure:

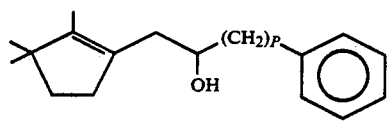

of our invention based on the ultimate end product is required in the perfume composition.

Accordingly, in perfume compositions and colognes from about 0.01% up to about 70% of the perfume composition may be at least one of the aryl oxabicyclooctane derivatives and phenyl norbornane derivatives of our invention or one of the compounds having the structure:

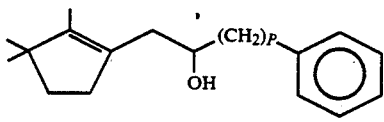

taken alone or taken together. In perfumed articles, the quantity of at least one of the aryl oxabicyclooctane derivatives and phenyl norbornane derivatives of our invention or one of the compounds having the structure:

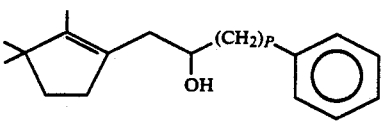

of our invention in a perfumed article may vary from about 0.005% up to about 25% of the perfumed article; and up to about 8% in the case of solid or liquid, anionic, cationic, nonionic or zwitterionic detergents, for example.

In addition, the perfume composition or fragrance composition of our invention can contain a vehicle or carrier for at least one of the aryl oxabicyclooctane derivatives and phenyl norbornane derivatives of our invention or for at least one of the compounds having the structure:

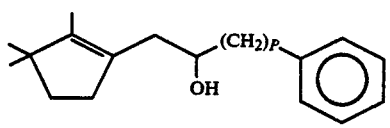

of our invention. The vehicle can be a liquid such as a non-toxic alcohol such as ethyl alcohol or a non-toxic glycol such as propylene glycol or the like. The carrier can also be an absorbent solid, such as a gum (e.g., gum arabic, xanthan gum, or guar gum or mixtures of same) or components for encapsulating the composition (such as gelatin as by means of coacervation or such as a urea-formaldehyde prepolymer when a polymeric wall is intended to be formed around a liquid perfume composition center).

The following Examples I–VIII serve to illustrate the processes for preparing the compounds of our invention and the compounds useful for their organoleptic properties. Examples following Example VIII (Examples IX, et seq.) illustrate organoleptic utilities of the aryl oxabicyclooctane derivatives and phenyl norbornane derivatives of our invention as well as the compounds having the structure:

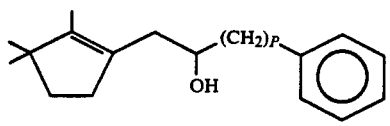

wherein P is 1 or 2 of our invention.

All parts and percentages given herein are by weight unless otherwise specified.

EXAMPLE I

Preparation of 1-Phenyl-2-Hydroxy-3(2',2'3'-Cyclopent-3'-Enyl) Propane

Reaction:

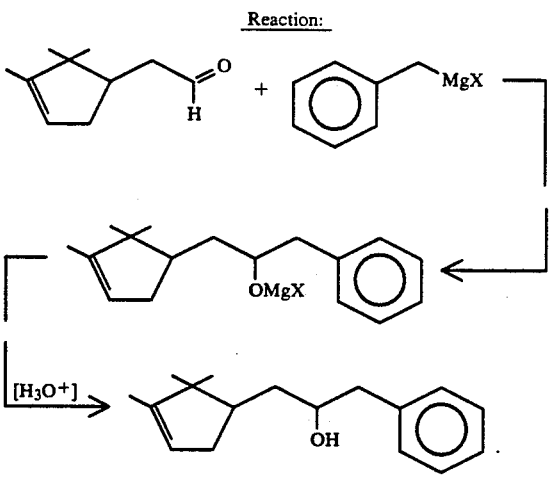

Into a 5 liter reaction vessel equipped with cooling bath, thermometer, addition funnel and reflux condenser with nitrogen blanket purge apparatus is placed 2.4 liters (4.8 moles) of benzylmangesiumchloride under a nitrogen blanket. The benzylmagnesiumchloride is cooled to 0° C., and over a 2.5 hour period while maintaining the temperature at 0° C., 653 grams (3.7 moles) of the compound having the structure:

is added to the reaction mass with stirring. The reaction mass is then permitted to warm to 15° C. and maintained at 15°–16° C. for a period of 1.5 hours.

The product in the reaction vessel now has the structure:

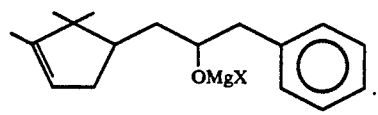

The reaction mass is then poured into 2 liters of 4.8 molar hydrochloric acid mixed with 2000 grams of ice.

The reaction mass now exists in two phases; an organic phase and an aqueous phase. The aqueous phase is washed with 400 ml toluene and the toluene extract is combined with the organic phase. The resulting organic phase is then washed with 400 ml of aqueous sodium bicarbonate (to a pH of 8 followed by 500 ml saturated sodium chloride). The resulting product is then fractionally distilled to yield the compound having the structure:

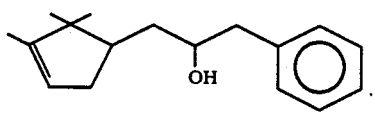

The distillation fractions are as follows:

| Fraction No. | Vapor Temp. (°C.) | Liquid Temp. (°C.) | Vacuum mm/Hg. Pressure |
|---|---|---|---|
| 1 | 32/120 | 48/148 | 1.35/1.68 |
| 2 | 155 | 164 | 2.32 |
| 3 | 90 | 200 | 1.75. |

FIG. 1 is the GC spectrum prior to distillation. The peak indicated by reference numeral 10 is the peak for the compound having the structure:

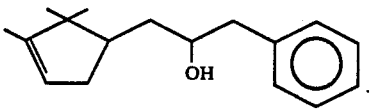

EXAMPLE II

Preparation of Benzyl Oxabicyclooctane Derivatives

Reaction:

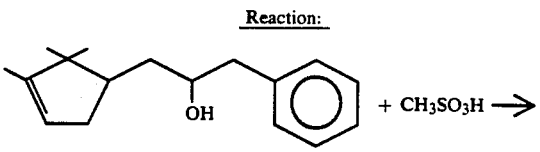

-continued
Reaction:

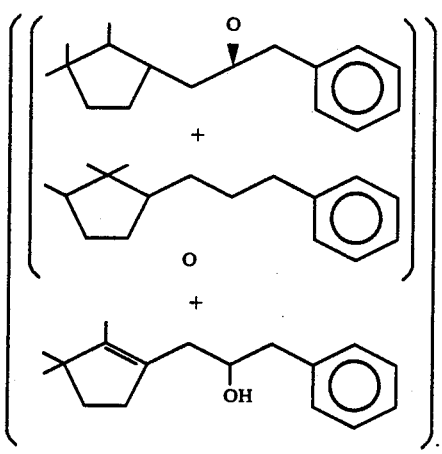

Into a 3 liter reaction vessel equipped with stirrer, thermometer and reflux condenser is placed a mixture of 710 grams of the compound having the structure:

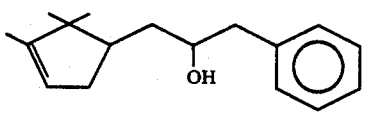

prepared according to Example I and 1 liter of nitromethane. The reaction mass is cooled to 18° C. and over a period of 5 minutes, 11.4 grams of methane sulfonic acid is added to the reaction mass.

The reaction mass is heated to 60° C. and maintained at 60° C. with stirring for a period of four hours. At the end of the four hour period, the reaction mass is heated to 80° C. and maintained at 80° C. for a period of five hours.

At the end of the five hour period, the reaction mass is washed with 300 ml of aqueous sodium bicarbonate. The reaction mass now exists in two phases; an aqueous phase and an organic phase. The aqueous phase is separated and washed with 400 ml toluene. The toluene extract is combined with the organic phase and the resulting material is washed with 500 ml saturated sodium chloride. The resulting product is then fractionally distilled to yield the following fractions:

| Fraction No. | Vapor Temp. (°C.) | Liquid Temp. (°C.) | Vacuum mm/Hg. Pressure |
|---|---|---|---|
| 1 | 50/45 | 52/78 | 13.5/7.84 |
| 2 | 133 | 141 | 5.50 |
| 3 | 139 | 144 | 5.65. |
| 4 | 154 | 176 | 6.25 |
| 5 | 155 | 184 | 6.15. |

The resulting product contains three compounds having the structures:

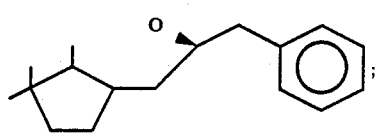

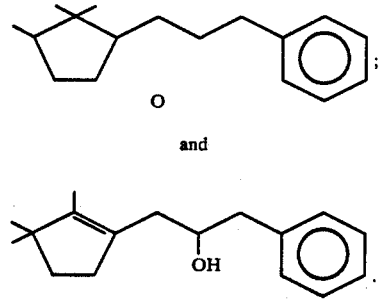

The fraction boiling at 133°-139° C. vapor temperature and 5.5-5.65 mm/Hg. pressure has the structure:

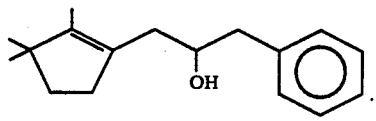

The substance boiling at 154°-155° C. at 6.15-6.25 mm/Hg. pressure is a mixture of compounds having the structures:

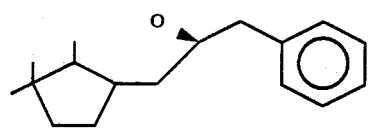

and

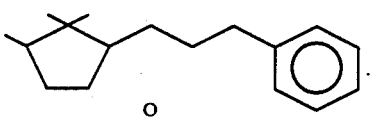

The compound having the structure:

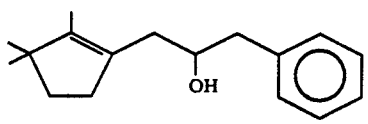

is identified as a result of interpretation of the NMR spectrum of FIG. 5 and the IR spectrum of FIG. 6. The mixture of compounds having the structures:

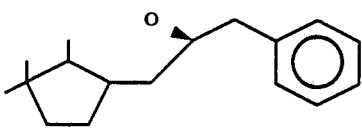

and

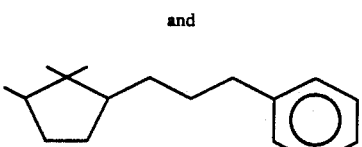

are identified as a result of the NMR spectrum set forth in FIG. 7 and the IR spectrum set forth in FIG. 8.

The compound having the structure:

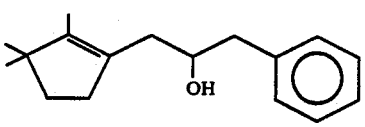

has an intense, civet/musky aroma with green topnotes. The mixture of compounds having the structures:

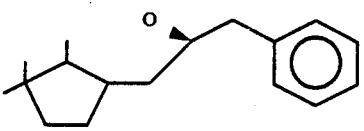

and

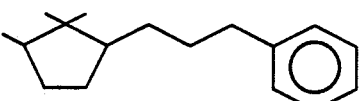

have a sweaty, animalic, dry-camphoraceous, woody-peppery aroma with green, herbaceous, sweaty, animalic and woody topnotes.

EXAMPLE III

Preparation of 1-Phenyl-2-Hydroxy-3(2',2'3'-Cyclopent-3'-Enyl) Propane

Reaction:

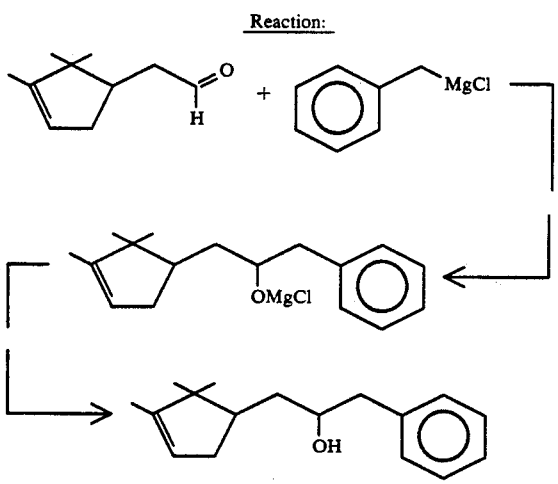

Into a 3 liter reaction vessel equipped with dry ice/isopropyl alcohol cooling bath is placed 1400 ml of a solution of 3.5 moles of benzylmagnesiumchloride in tetrahydrofuran under a nitrogen blanket. The solution of benzylmagnesiumchloride is cooled to 0° C. Over a 1.5 hour period, 300 grams of the compound having the structure:

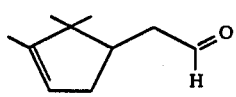

is added to the reaction mass while maintaining the reaction mass at 0° C. At the end of the addition of the compound having the structure:

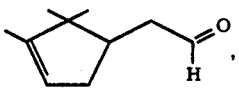

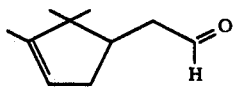

the temperature of the reaction mass is permitted to rise to 20° C. The reaction mass is maintained at 20° C. for a period of 3.5 hours with stirring.

The compound now contained in the reaction mass has the structure:

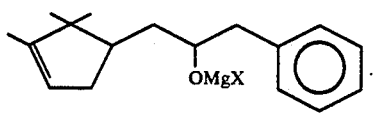

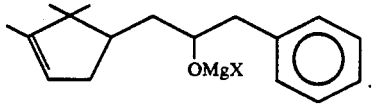

The reaction mass is then poured into a mixture of 1500 grams of ice and 3 liters of 4 molar hydrochloric acid.

The reaction mass now exists in two phases; an organic phase and an aqueous phase. The organic phase is then extracted with two 300 ml volumes of diethyl ether. The ether extract is combined with the organic phase and the resulting product is then washed with 400 ml of 10% sodium bicarbonate followed by 400 ml of saturated sodium chloride. The resulting product is filtered through anhydrous magnesium sulfate and distilled in a factional distillation column yielding the following fractions:

| Fraction No. | Vapor Temp. (°C.) | Liquid Temp. (°C.) | Vacuum mm/Hg. Pressure |
|---|---|---|---|
| 1 | 25/34 | 39/75 | 2.20/3.16 |
| 2 | 75 | 122 | 2.12 |
| 3 | 93 | 132 | 2.06 |
| 4 | 107 | 137 | 1.99 |
| 5 | 124 | 145 | 1.96 |
| 6 | 131 | 150 | 1.93 |
| 7 | 135 | 153 | 1.91 |
| 8 | 140 | 156 | 1.90 |
| 9 | 143 | 158 | 1.88 |
| 10 | 145 | 160 | 1.87 |
| 11 | 148 | 160 | 1.86 |
| 12 | 149 | 161 | 1.85 |

-continued

| Fraction No. | Vapor Temp. (°C.) | Liquid Temp. (°C.) | Vacuum mm/Hg. Pressure |
|---|---|---|---|
| 13 | | 200 | 1.68. |

Fractions 6–12 bulked and utilized in Example IV. The compound having the structure:

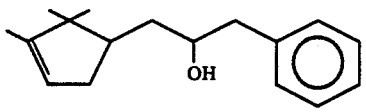

is identified using the NMR spectrum of FIG. 10 and the infra-red spectrum of FIG. 11.

EXAMPLE IV

Preparation of Benzyl Oxabicyclooctane Derivatives

Reaction:

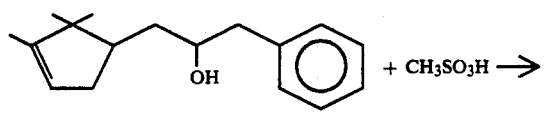 + CH$_3$SO$_3$H →

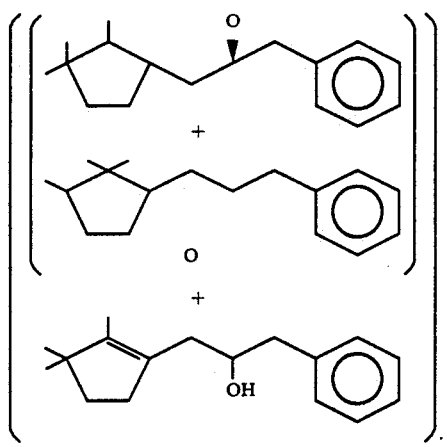

Into a 2 liter reaction vessel equipped with thermometer, heating mantle, reflux condenser and addition funnel is placed a mixture of 500 ml of nitroethane and 290 grams of the compound having the structure:

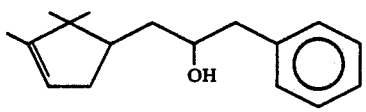

prepared according to Example III. Over a period of 0.25 hours while maintaining the reaction mass at 21°–23° C., 4.6 grams of methane sulfonic acid is added to the reaction mass.

With stirring, the reaction mass is heated to 70° C. and maintained at 70°–80° C. for a period of 5.5 hours.

At the end of the 5.5 hour period, 250 ml of 10% sodium bicarbonate is added to the reaction mass. The reaction mass now exists in two phases; an aqueous phase and an organic phase. The organic phase is separated from the aqueous phase and washed with 400 ml saturated sodium chloride. The resulting organic phase is then filtered through anhydrous magnesium sulfate and distilled through a fractional distillation column yielding the following fractions:

| Fraction No. | Vapor Temp. (°C.) | Liquid Temp. (°C.) | Vacuum mm/Hg. Pressure |
|---|---|---|---|
| 1 | 30/45 | 40/90 | 1.20/3.08 |
| 2 | 142 | 180 | 3.60 |
| 3 | 154/107 | 197 | 4.20. |

The mixture of compounds distilling at 142° C. and 3.60 mm/Hg. has the structures:

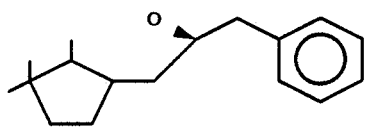

and

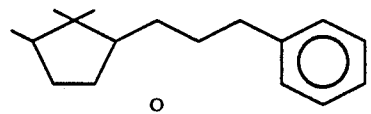

as identified in the NMR spectrum of FIG. 13 and the infra-red spectrum of FIG. 14. This product has a sweaty, animalic, dry-camphoraceous, woody-peppery aroma with green, herbaceous, sweaty, animalic and woody topnotes.

EXAMPLE V

Preparation of 1-Phenyl-3-Hydroxy-4(2',3',3'-Cyclopent-3'-Enyl) Butane

Reaction:

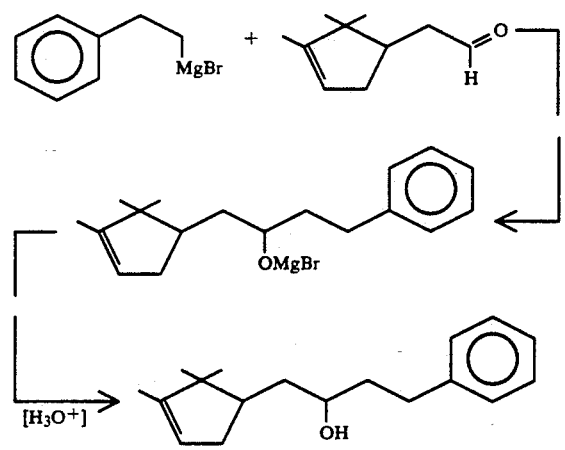

Into a 5 liter reaction vessel equipped with stirrer, thermometer, reflux condenser and heating mantle and provided with nitrogen blanket apparatus and cooling coil are added 72 grams (3 moles) of magnesium ribbon and 150 ml tetrahydrofuran. The resulting product is heated to reflux (68° C.). During refluxing with stirring 2 ml of bromine is added. The resulting product is refluxed for a period of one hour. The reaction mass is then heated to 134° C. and over a period of one hour, 400 grams (2.16 moles) of 1-phenyl-2-bromoethane is added to the reaction mass. The reaction mass is refluxed for an additional 15 minutes. The reaction mass is then aged for a period of two hours and then cooled to 0° C. Over a period of two hours while maintaining the reaction mass at 0°-5° C., 182 grams of the compound having the structure:

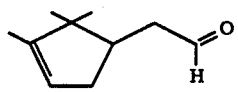

is added to the reaction mass. The reaction mass is then aged for a period of five hours allowing the temperature to rise to 10° C.

The reaction mass is then poured into 2 liters of saturated ammonium acetate solution.

The reaction mass is then combined with 1 liter of one molar hydrochloric acid followed by 100 ml concentrated hydrochloric acid. The reaction mass now exists in two phases; an organic phase and an aqueous phase. The organic phase is separated from the aqueous phase and the aqueous phase is extracted with 500 ml toluene. The toluene extract is combined with the organic phase and washed with 800 ml 10% aqueous sodium bicarbonate, followed by 1000 ml saturated sodium chloride. The resulting product is then fractionally distilled yielding the following fractions:

| Fraction No. | Vapor Temp. (°C.) | Liquid Temp. (°C.) | Vacuum mm/Hg. Pressure |
|---|---|---|---|
| 1 | 78/ | 142/ | 2.45 |
| 2 | 131 | 162 | 0.735 |
| 3 | 105 | 200 | 0.414. |

The resulting product has the structure:

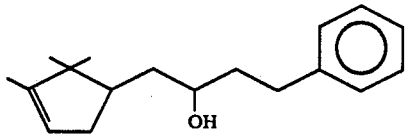

as confirmed by NMR and IR analysis, set forth in FIGS. 16 and 17.

EXAMPLE VI

Preparation of Phenylethyl Oxabicyclooctane derivatives

Reaction:

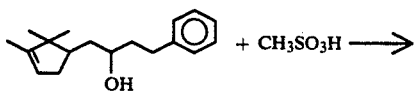 + CH$_3$SO$_3$H →

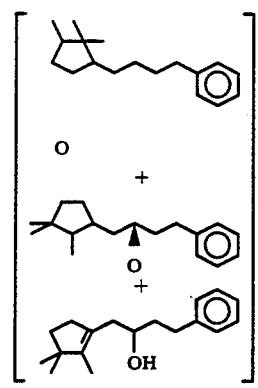

One gram of the compound having the structure:

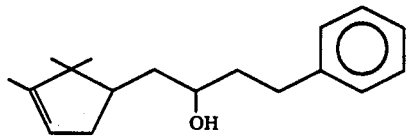

is heated with 1 ml nitromethane and 6 drops of methane sulfonic acid in a flask equipped with stirring bar and reflux condenser. The reaction takes place over a period of one hour. The resulting product is a mixture of the compounds having the structures:

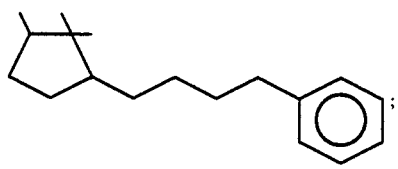;

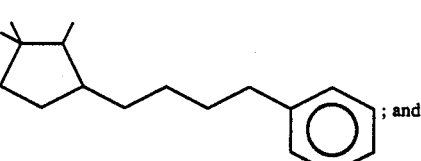; and

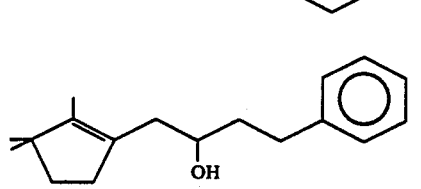

The compound having the structure:

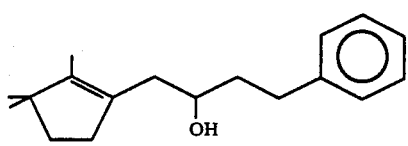

is separated from the mixture of compounds:

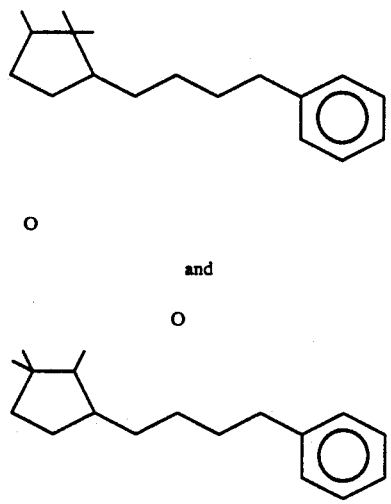

on a micro distillation column.
The compound having the structure:

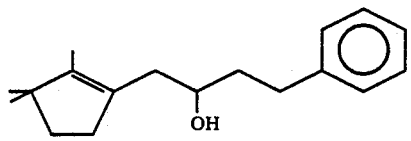

has an intense amber aroma with green topnotes. The mixture of compounds having the structures:

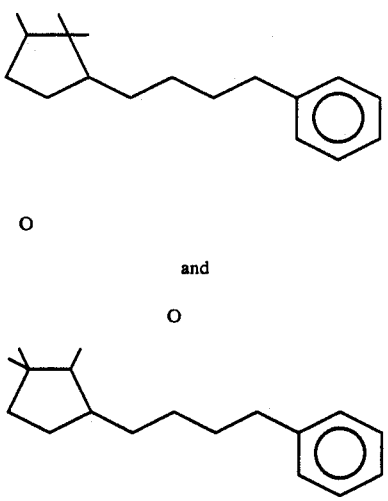

has a sweaty, animalic, musky and amber aroma with cigar box-like and green topnotes.

The foregoing structures are confirmed by NMR and IR analyses the spectra for which are set forth in FIGS. 19, 20, 21, 22, 23 and 24.

EXAMPLE VII

Preparation of
1-Phenyl-1-Hydroxy-2(2',2',3'-Trimethylcyclopent-3'-Enyl) Ethane

Reation:

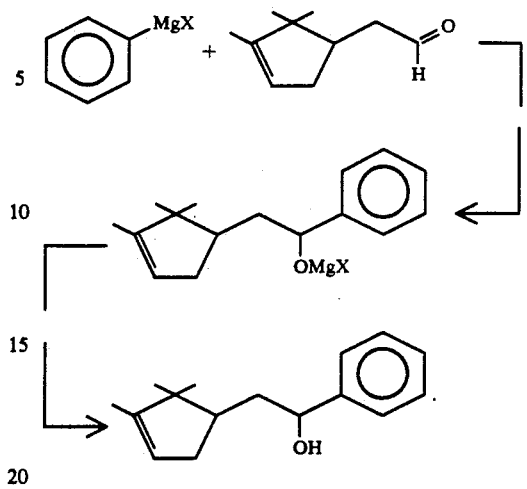

Into a 3 liter reaction vessel equipped with stirrer, thermometer and dry ice-isopropyl alcohol cooling bath is placed 1600 ml of a phenyl magnesium chloride solution (2.0 molar) in tetrahydrofuran under a nitrogen blanket. The phenyl magnesium chloride solution is cooled to 0° C. Over a period of one hour and 15 minutes while the maintaining the temperature at 0° C, 466 grams of the compound having the structure:

is fed into the reaction mass. The reaction mass is then aged for 15 minutes and the resulting product is poured onto 2.5 liters of 4 molar hydrochloric acid and 1500 grams of ice.

The resulting product now exists in two phases; an organic phase and an aqueous phase. The organic phase is separated from the aqueous phase. The aqueous phase is extracted with two 500 ml portions of diethyl ether. The ether extract is combined with the organic phase and the resulting product is washed with 300 ml 10% aqueous sodium bicarbonate solution followed by 600 ml saturated sodium chloride. The resulting product is then fractionally distilled on a distillation column yielding the following fractions:

| Fraction No. | Vapor Temp. (°C.) | Liquid Temp. (°C.) | Vacuum mm/Hg. Pressure |
|---|---|---|---|
| 1 | 57/83 | 134/143 | 3.64/3.58 |
| 2 | 117 | 155 | 3.64 |
| 3 | 154/ | 173 | 2.95 |
| 4 | 135 | 210 | 2.90. |

The resulting product has the structure:

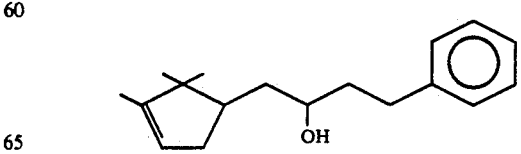

as confirmed by NMR and IR analyses the spectra for which are set forth in FIGS. 26 and 27, described supra.

EXAMPLE VIII

Preparation of Phenyl Norbornane Derivatives

Reaction:

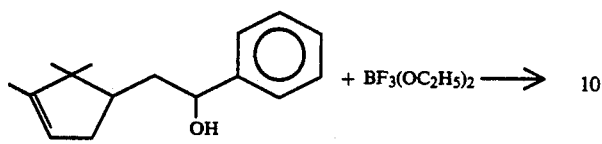

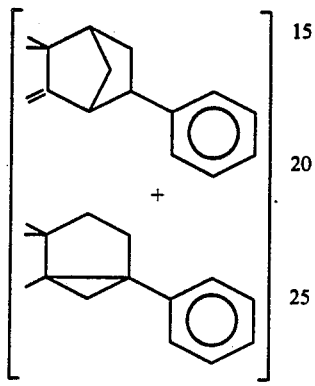

One gram of the compound having the structure:

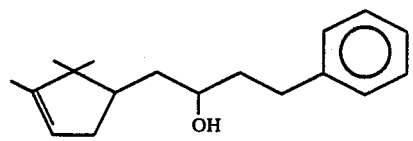

is admixed with 1 ml nitroethane and 4 drops of boron trifluoride diethyl etherate in a 10 cc reaction flask equipped with stirrer, thermometer and reflux condenser. The resulting product is heated on a steam bath for one hour resulting in formation of a mixture of compounds having the structures:

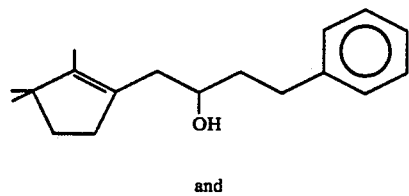

and

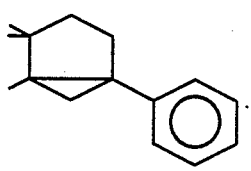

The structures are confirmed by NMR and IR analyses as set forth in FIGS. 29, 30, 31 and 32. The compounds having the structures:

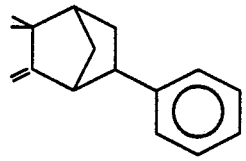

and

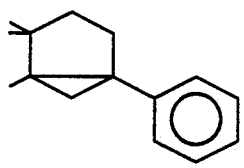

are separated from the remainder of the reaction mass (which also included the compound having the structure:

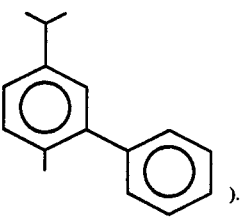

).

The mixture of compounds having the structures:

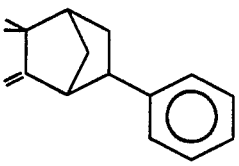

and

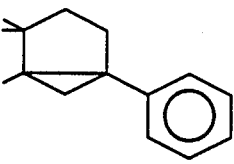

has an intense, woody, amber, musky aroma with cigar box-like topnotes.

EXAMPLE IX

The aryl oxabicyclooctane derivatives and phenyl norbornane derivatives of our invention produced according to Examples I–VIII have very long-lasting and intense, sweaty, animalic, amber, musky, dry-camphoraceous, woody-peppery aromas with green, herbaceous, sweaty, animalic, cigar box-like and woody topnotes which may be utilized to a great extent in inexpensive functional products. The following pine fragrance demonstrates the use of these materials in perfume compositions.

| Ingredients | Parts by Weight | | |
|---|---|---|---|
| | IX(A) | IX(B) | IX(C) |
| Isobornyl acetate | 100 | 100 | 100 |
| Camphor | 10 | 10 | 10 |
| Terpineol | 25 | 25 | 25 |
| Fir Balsam Absolute (50% in Diethyl Phthalate) | 20 | 20 | 20 |
| Coumarin | 4 | 4 | 4 |
| Linalool | 30 | 30 | 30 |
| Anethol | 2 | 2 | 2 |
| Fenchyl Alcohol | 10 | 10 | 10 |
| Lemon Terpenes Washed | 50 | 50 | 50 |
| Borneol | 5 | 5 | 5 |
| Galbanum Oil | 5 | 5 | 5 |
| Turpentine Russian | 150 | 150 | 150 |
| Pinus Pumilionus | 50 | 50 | 50 |
| Eucalyptol | 50 | 50 | 50 |
| 2,2,6-Trimethyl-1-cyclo-hexene-1-carboxaldehyde | 5 | 5 | 5 |
| Maltol (1% in Diethyl Phthalate) | 5 | 5 | 5 |
| Mixture of compounds having the structures: | 12 | 0 | 0 |

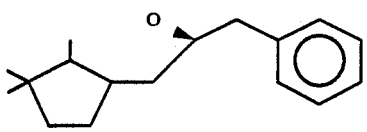

and

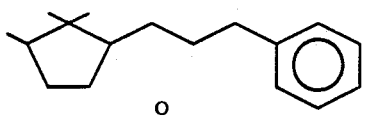

produced according to Example II.

Mixture of compounds having the structures:    0    12    0

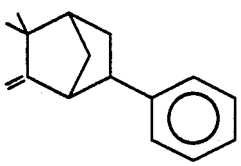

and

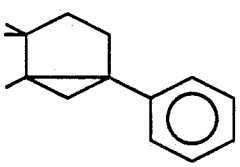

produced according to Example VIII.

Mixture of compounds having the structures:    0    0    12

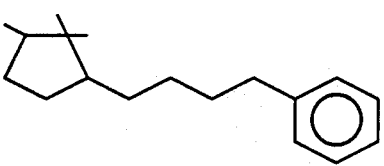

and

| Ingredients | Parts by Weight | | |
|---|---|---|---|
| | IX(A) | IX(B) | IX(C) |

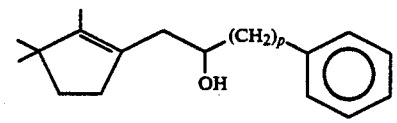

produced according to Example VI.

The mixture of compounds having the structures:

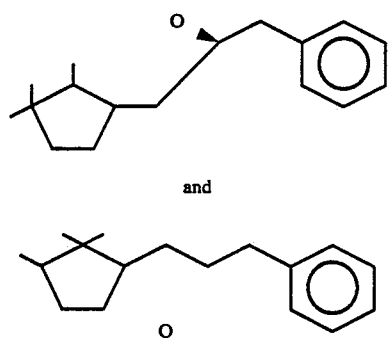

and prepared according to Example II adds to this pine fragrance sweaty, animalic, dry-camphoraceous and woody-peppery undertones with green, herbaceous, sweaty, animalic and woody topnotes. Accordingly, the perfume composition of Example IX(A) can be described as "piney, with sweaty, animalic, dry-camphoraceous and woody-peppery undertones with green, herbaceous, sweaty, animalic and woody topnotes".

The mixture of compounds having the structures:

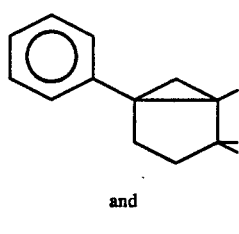

and

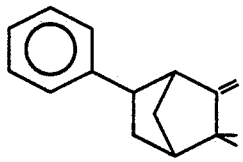

produced according to Example VIII imparts to this piney formulation, intense, woody, amber and musky undertones with cigar box-like topnotes. Accordingly, the perfume composition of Example IX(B) can be described as "piney with woody, amber and musky undertones and cigar box-like topnotes".

The mixture of compounds having the structures:

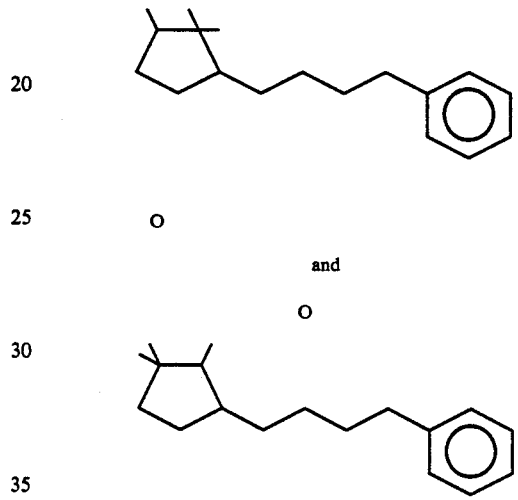

produced according to Example VI imparts to this piney perfume formulation sweaty, animalic, musky and amber undertones with cigar box-like and green topnotes. Accordingly, the perfume composition of Example IX(C.) can be described as "a piney aroma with sweaty, animalic, musky and amber undertones and cigar box-like and green topnotes".

EXAMPLE X

The compounds defined according to the generic structure:

wherein P is 1 or 2 of our invention have very long-lasting and intense civet/musky and amber aromas with green topnotes which may be utilized to a great extent in inexpensive functional products. The following pine fragrance demonstrates the use of these materials in perfume compositions:

| Ingredients | Parts by Weight | |
|---|---|---|
| | X(A) | X(B) |
| Isobornyl acetate | 100 | 100 |
| Camphor | 10 | 10 |
| Alpha-Terpineol | 25 | 25 |

-continued

| Ingredients | Parts by Weight | |
|---|---|---|
| | X(A) | X(B) |
| Fir Balsam Absolute (50% in Diethyl Phthalate) | 20 | 20 |
| Coumarin | 4 | 4 |
| Linalool | 30 | 30 |
| Anethol | 2 | 2 |
| Fenchyl Alcohol | 10 | 10 |
| Lemon Terpenes Washed | 50 | 50 |
| Borneol | 5 | 5 |
| Galbanum Oil | 5 | 5 |
| Turpentine Russian | 150 | 150 |
| Pinus Pumilionus | 50 | 50 |
| Eucalyptol | 50 | 50 |
| 2,2,6-Trimethyl-1-cyclohexene-1-carboxaldehyde | 5 | 5 |
| Maltol (1% in Diethyl Phthalate) | 5 | 5 |
| The compound having the structure: | 14 | 0 |

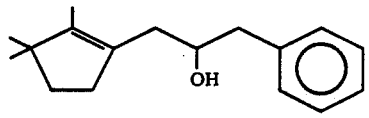

produced according to Example II.

| The compound having the structure: | 0 | 14 | produced according to Example VI.

The compound having the structure:

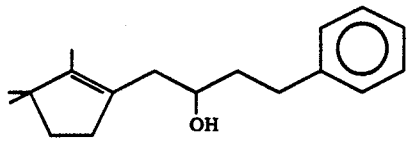

produced according to Example II adds to this pine fragrance intense, civet/musky undertones with green topnotes. Accordingly, the pine formulation of Example X(A) can be described as "a piney aroma with civet/musky undertones and green topnotes".

The compound having the structure:

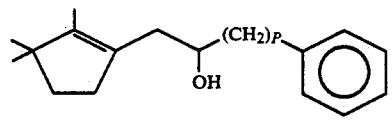

produced according to Example VI adds to this pine formulation an intense, amber undertone with green topnotes. Accordingly, the fragrance of Example X(B) can be described as "a piney aroma with intense, amber undertones and green topnotes".

EXAMPLE XI

Cosmetic Powder Preparation

A cosmetic powder is prepared by mixing in a ball mill 100 grams of talcum powder with 0.25 grams of one of the substances set forth in Table II below containing at least one of the aryl oxabicyclooctane derivatives and phenyl norbornane derivatives of our invention or one of the compounds defined according to the structure:

wherein P is 1 or 2 of our invention. Each of the cosmetic powders has an excellent aroma as described in Table II below:

TABLE II

| Perfumery Substance | Aroma Nuance |
|---|---|
| Mixture of compounds having the structures: and defined according to Example II. | A sweaty, animalic, dry-camphoraceous and woody-peppery aroma with green herbaceous, sweaty, animalic and woody topnotes. |
| Mixture of compounds having the structures: | An intense, woody, amber, musky aroma with cigar box-like topnotes. |

TABLE II-continued

| Perfumery Substance | Aroma Nuance |
|---|---|
| 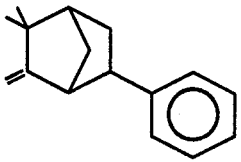 and 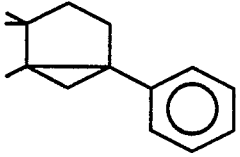 prepared according to Example VIII. | |
| Mixture of compounds having the structures: 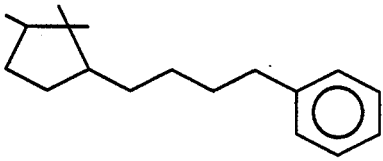 and 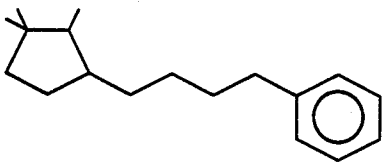 prepared according to Example VI. | A sweaty, animalic, musky and amber aroma with cigar box-like and green topnotes. |
| The compound having the structure: 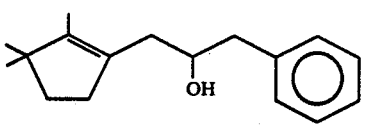 produced according to Example II. | An intense, civet/musky aroma with green topnotes. |
| The compound having the structure: 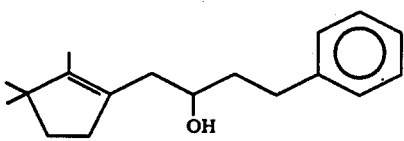 prepared according to Example VI. | An intense, amber aroma with green topnotes. |
| Perfume composition of Example IX(A). | Piney, with sweaty, animalic, dry-camphoraceous and woody-peppery undertones with green, herbaceous, sweaty, animalic and woody topnotes. |
| Perfume composition of Example IX(B). | Piney, with woody, amber and musky undertones and cigar box-like topnotes. |
| Perfume composition of Example IX(C). | A piney aroma, with sweaty, animalic, musky and amber undertones and cigar box- |

| Perfumery Substance | Aroma Nuance |
|---|---|
| | like and green topnotes. |
| Perfume composition of Example X(A). | A piney aroma, with civet/musky undertones and green topnotes. |
| Perfume composition of Example X(B). | A piney aroma with intense, amber undertones and green topnotes. |

EXAMPLE XII

Perfumed Liquid Detergent

Concentrated liquid detergents (Lysine salt of n-dodecylbenzene sulfonic acid as more specifically described in U.S. Pat. No. 3,948,818, issued on Apr. 6, 1976, the specification for which is incorporated herein) with aromas as set forth in Table II of Example XI, supra, are prepared containing 0.10%, 0.15%, 0.20%, 0.25%, 0.30% and 0.35% of each of the substances of Table II of Example XI. They are prepared by adding and homogeneously admixing the appropriate quantity of one of the substances of Table II of Example XI in the liquid detergent. The detergents all possess excellent aromas as set forth in Table II of Example XI.

EXAMPLE XIII

Preparation Of A Cologne And Handkerchief Perfume

The substances set forth in Table II of Example XI are incorporated separately into colognes at concentrations of 2.0%, 2.5%, 3.0%, 3.5%, 4.0%, 4.5% and 5.0% in 75%, 80%, 85% and 90% aqueous food grade ethanol solutions and into handkerchief perfumes at concentrations of 15%, 20%, 25% and 30%, in 80%, 85%, 90% and 95% aqueous food grade ethanol solutions. Distinctive aromas as set forth in Table II of Example XI, supra, are imparted to the colognes and to the handkerchief perfume compositions at all levels indicated.

EXAMPLE XIV

Preparation Of Soap Composition

One hundred grams of soap chips (IVORY ®, produced by the Procter & Gamble Company of Cincinnati, Ohio) are admixed with 1 gram of each of the substances of Table II of Example XI, supra, until homogeneous compositions are obtained. The homogeneous compositions are each separated then heated under 3 atmospheres pressure at 180° C. for a period of three hours and the resulting liquid samples are placed in soap molds. The resulting soap cake, on cooling, manifest excellent long-lasting aromas as set forth in Table II of Example XI.

EXAMPLE XV

Preparation Of Solid Detergent Compositions

Detergents are prepared from the following ingredients according to Example II of Canadian Letters Patent No. 1,007,948, the specification for which is incorporated by reference herein.

| Ingredients | Parts by Weight |
|---|---|
| NEODOL ® 45-11 (A $C_{14}$–$C_{15}$ alcohol ethoxylated with 11 moles of ethylene oxide | 12 |
| Sodium carbonate | 55 |
| Sodium citrate | 20 |
| Sodium sulfate, water brighteners | q.s. |

This detergent is a phosphate-free detergent. A total of 100 grams of said detergent is admixed separately with 0.10, 0.15, 0.20 and 0.25 grams of each of the substances of Table II of Example XI. Each of the detergent samples has excellent aromas as set forth in Table II of Example XI.

EXAMPLE XVI

Dryer-Added Fabric Softener Article

Utilizing the procedure of Example II at column 15 of U.S. Pat. No. 3,623,396, the specification for which is incorporated by reference herein, a non-woven cloth substrate useful as s dryer-added fabric softening article of manufacture is prepared wherein the substrate, the substrate coating and the outer coating and the perfuming material are as follows:

1. A water "dissolvable" paper ("Dissolvo Paper");
2. Adogen 448 (m.p. about 140° F.) as the substrate coating; and
3. An outer coating having the following formulation (m.p. about 150° F.):
   57%—$C_{20-22}$ HAPS;
   22%—isopropyl alcohol;
   20%—antistatic agent; and
   1%—of one of the substances of Table II of Example XI, supra.

Fabric softening compositions containing one of the substances of Table II of Example XI consist essentially of a substrate having a weight of about 3 grams per 100 square inches of substrate coating having a weight of about 1.85 grams per 100 square inches; and an outer coating having a weight of about 1.4 grams per 100 square inches thereby providing a total aromatized substrate and an outer coating weight ratio of about 1:1 by weight of the substrate.

Pleasant aromas as set forth in Table II of Example XI are imparted to the head space in the dryer on operation thereof using the said drier-added fabric softening non-woven fabric.

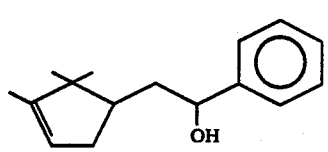 + BF$_3$(OC$_2$H$_5$)$_2$ → 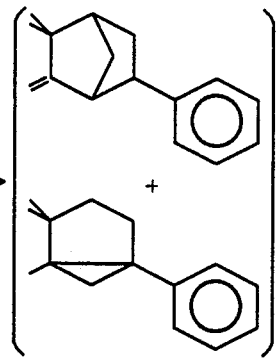
7. The process of claim 4 defined according to the reactions:
wherein X represents chloro or bromo.
* * * * *
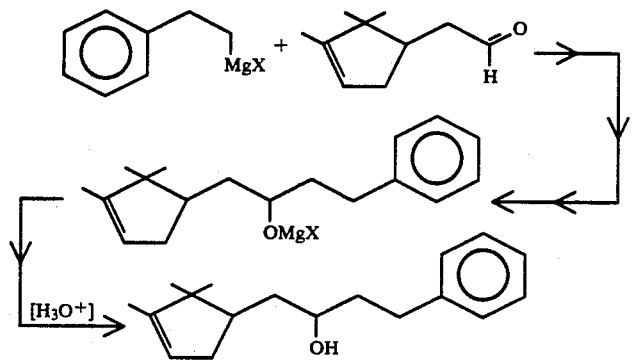
and
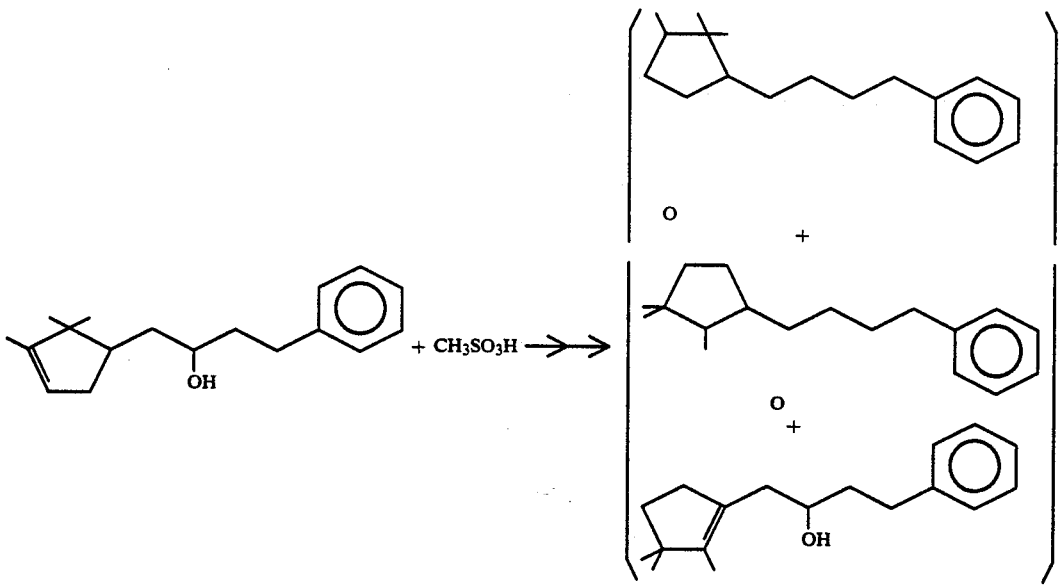

What is claimed is:

1. A composition of matter defined according to the structure:

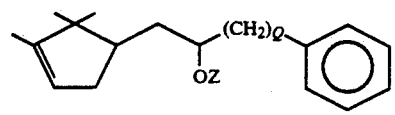

wherein Z represents H or MgX; X represents chloro or bromo; and Q represents 1 or 2.

2. The composition of matter of claim 1 wherein Z represents hydrogen.

3. The composition of matter of claim 1 wherein Z represents MgX.

4. A process for preparing an aryl oxabicyclooctane derivative or a phenyl norbornane derivative or a phenyl norbornane derivative comprising the steps of carrying out the reaction:

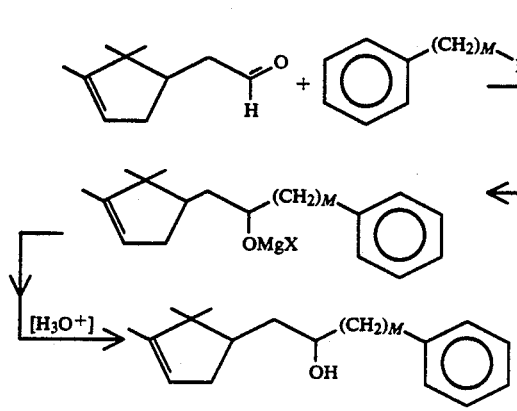

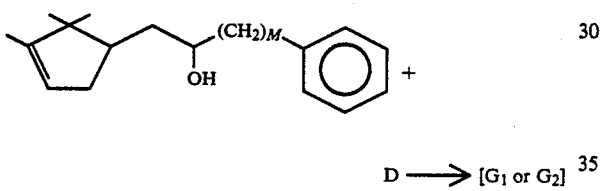

wherein X represents chloro or bromo followed by the reaction:

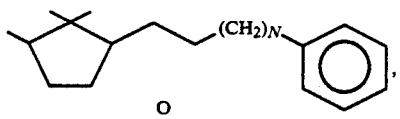

D ⟶ [G₁ or G₂]

wherein M represents 0, 1 or 2; D represents a cyclizing reagent selected from the group consisting of (i) mixtures of a $C_1$-$C_2$ nitroalkane and methane sulfonic acid and (ii) mixtures of borontrifluoride diethyl etherate and a $C_1$-$C_2$ nitroalkane; wherein $G_1$ represents a mixture of compounds having the structures:

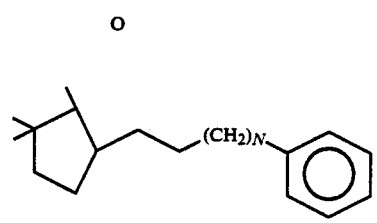

and

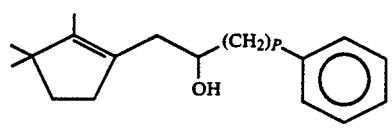

with N and P being the same and being 1 or 2; wherein $G_2$ represents a mixture of compounds having the structures:

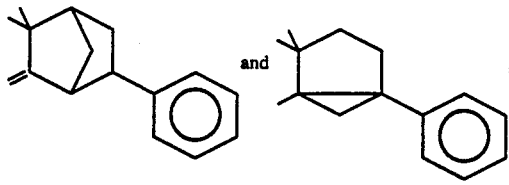

with the provisos that when M is 1 or 2, then the term [$G_1$ or $G_2$] represents a mixture of compounds defined according to the structures:

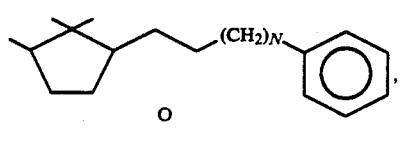

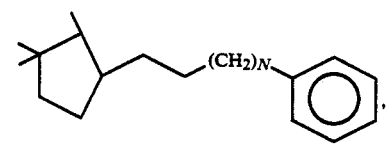

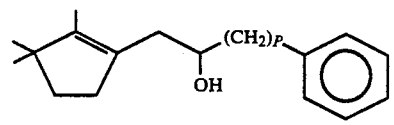

the cyclization agent D being a mixture of a $C_1$-$C_2$ nitroalkane and methane sulfonic acid; the reaction temperature being in the range of from about 60° C. up to about 90° C. for a period of time of from about three hours up to about ten hours and when M is 0 then the term [$G_1$ or $G_2$] is a mixture of compounds having the structures:

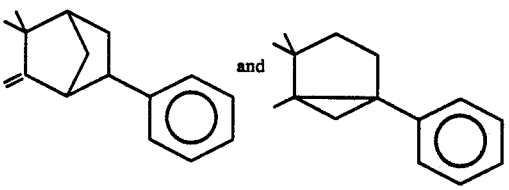

and the cyclization agent D is a mixture of boron trifluoride diethyl etherate, and a $C_1$-$C_2$ nitroalkane, the reaction temperature being in the range of from about 60° C. up to about 90° C. for a period of time of from about three hours up to about ten hours.

5. The process of claim 4 defined according to the reactions:

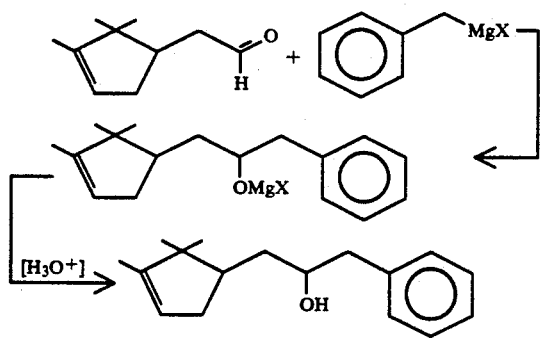
and
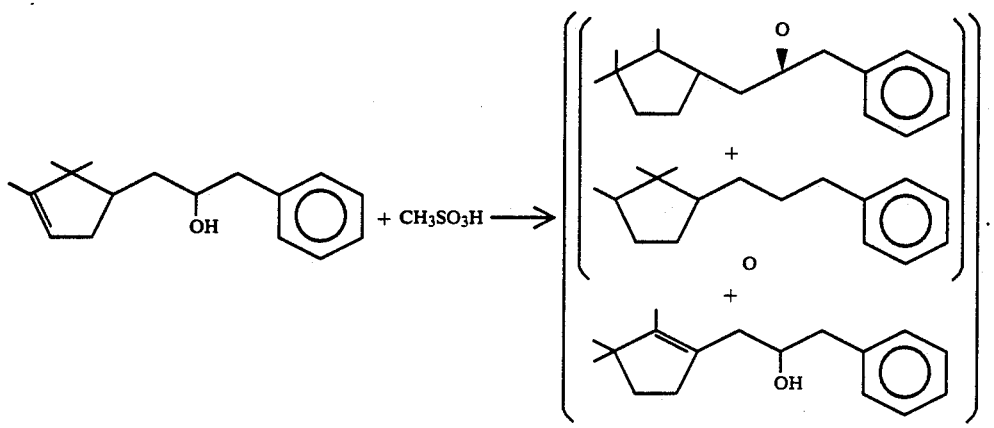
6. The process of claim 4 defined according to the reactions:
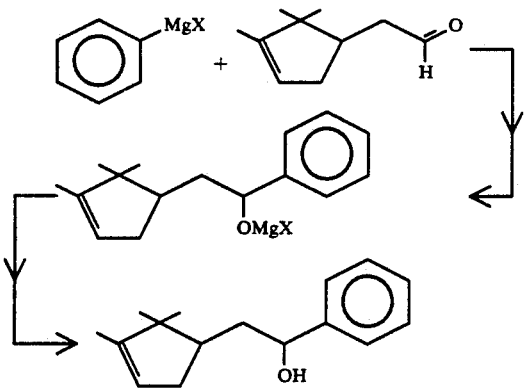
and